US011191812B2

(12) United States Patent
Chan et al.

(10) Patent No.: US 11,191,812 B2
(45) Date of Patent: Dec. 7, 2021

(54) COMPOSITIONS IN THE FORM OF AN INJECTABLE AQUEOUS SOLUTION COMPRISING HUMAN GLUCAGON AND A CO-POLYAMINO ACID

(71) Applicant: ADOCIA, Lyons (FR)

(72) Inventors: You-Ping Chan, Ternay (FR); Alexandre Geissler, Lyons (FR); Romain Noel, Villeurbanne (FR); Richard Charvet, Rillieux la Pape (FR); Nicolas Laurent, Miribel (FR)

(73) Assignee: ADOCIA, Lyons (FR)

( * ) Notice: Subject to any disclaimer, the term of this patent is extended or adjusted under 35 U.S.C. 154(b) by 38 days.

(21) Appl. No.: 16/213,836

(22) Filed: Dec. 7, 2018

(65) Prior Publication Data

US 2019/0275109 A1 Sep. 12, 2019

Related U.S. Application Data

(60) Provisional application No. 62/606,137, filed on Dec. 7, 2017.

(30) Foreign Application Priority Data

Dec. 7, 2017 (FR) ..................................... 17/61809
Jun. 29, 2018 (FR) ..................................... 18/55939

(51) Int. Cl.
| A61K 38/00 | (2006.01) |
| A61K 38/26 | (2006.01) |
| A61K 47/34 | (2017.01) |
| A61K 9/08 | (2006.01) |
| A61K 9/00 | (2006.01) |
| A61K 47/02 | (2006.01) |

(52) U.S. Cl.
CPC ............ *A61K 38/26* (2013.01); *A61K 9/0019* (2013.01); *A61K 9/08* (2013.01); *A61K 47/02* (2013.01); *A61K 47/34* (2013.01)

(58) Field of Classification Search
None
See application file for complete search history.

(56) References Cited

U.S. PATENT DOCUMENTS

| 6,384,016 B1 | 5/2002 | Kaarsholm |
| 10,383,918 B2 | 8/2019 | Geissler et al. |
| 10,485,851 B2 | 11/2019 | Geissler et al. |
| 2011/0082080 A1* | 4/2011 | Levetan .................... A61P 3/06 514/7.3 |
| 2011/0097386 A1 | 4/2011 | Steiner et al. |
| 2015/0291680 A1 | 10/2015 | Ward et al. |

FOREIGN PATENT DOCUMENTS

| FR | 2 801 226 A1 | 5/2001 |
| FR | 2 840 614 A1 | 12/2003 |
| FR | 3 052 071 A1 | 12/2017 |
| GB | 1 202 607 A | 8/1970 |
| WO | 2011/138802 A1 | 11/2011 |
| WO | 2012/059764 A1 | 5/2012 |
| WO | 2013/101749 A1 | 7/2013 |
| WO | 2013/104861 A1 | 7/2013 |
| WO | 2014/096440 A2 | 6/2014 |
| WO | 2015/095389 A1 | 6/2015 |
| WO | 2017/211918 A1 | 12/2017 |
| WO | 2017211917 A1 | 12/2017 |

OTHER PUBLICATIONS

Feb. 19, 2020 U.S. Office Action issued U.S. Appl. No. 16/213,707.
Dec. 13, 2019 Office Action issued in U.S. Appl. No. 16/213,929.
Deming; "Polypeptide and Polypeptide Hybrid Copolymer Synthesis via NCA Polymerization;" Adv. Polym. Sci; 2006; pp. 1-18; vol. 202.
Deming; "Facile synthesis of block copolypeptides of defined architecture;" Nature; 1997; pp. 386-389; vol. 390.
Onoue et al.; "Mishandling of the Therapeutic Peptide Glucagon Generates Cytotoxic Amyloidogenic Fibrils;" Pharmaceutical Research; Jul. 2004; vol. 21, No. 7.
Joshi et al., "The degradation pathways of glucagon in acidic solutions;" International Journal of Pharmaceutics 2000; pp. 115-125; vol. 203.
Jackson et al.; "Stable Liquid Glucagon Formulations for Rescue Treatment and Bi-Hormonal Closed-Loop Pancreas;" Curr. Diab. Rep.; 2012; pp. 705-710; vol. 12.
Matilainen et al.; "The Effect of Cyclodextrins on Chemical and Physical Stability of Glucagon and Characterization of Glucagon/g-CD Inclusion Complexes;" Journal of Pharmaceutical Sciences; 2008; pp. 2720-2729; vol. 97, No. 7.
Matilainen et al.; "The stability and dissolution properties of solid glucagon/g-cyclodextrin powder;" European Journal of Pharmaceutical Sciences; 2009; pp. 412-420; vol. 36.
Garay et al.; "Antibodies against polyethylene glycol in healthy subjects and in patients treated with PEG-conjugated agents;" Expert Opinion Drug Delivery; 2012; pp. 1319-1323; vol. 9.
Ganson et al.; "Pre-existing anti-poly-ethylene glycol antibody linked to first-exposure allergic reactions to pegnivacogin, a PEGylated RNA aptamer;" J Allergy Clin Immunol; 2016; pp. 1610-1613.e7.
Tan et al.; "Coadministration of Glucagon-Like Peptide-1 During Glucagon Infusion in Humans Results in Increased Energy Expenditure and Amelioration of Hyperglycemia;" Diabetes; 2013; pp. 1131-1138; vol. 62.
Lu et al.; "Hexamethyldisilazane-Mediated Controlled Polymerization of a-Amino Acid N-Carboxyanhydrides;" J. Am. Chem. Soc; 2007; pp. 14114-14115; vol. 129.
Lu et al.; "N-Trimethyisilyl Amines for Controlled Ring-Opening Polymerization of Amino Acid N-Carboxyanhydrides and Facile End Group Functionalization of Polypeptides;" J. Am. Chem. Soc.; 2008; pp. 12562-12563 and pp. S1-S8 vol. 130.

(Continued)

*Primary Examiner* — Jeanette M Lieb
(74) *Attorney, Agent, or Firm* — Oliff PLC

(57) ABSTRACT

Physically stable compositions in the form of an injectable aqueous solution, for which the pH is comprised from 6.0 to 8.0, having at least: human glucagon, and a co-polyamino acid bearing carboxylate charges and Hy hydrophobic radicals. In one embodiment, the compositions according to the invention also includes a gastro-intestinal hormone.

17 Claims, 1 Drawing Sheet

(56) References Cited

OTHER PUBLICATIONS

Naiki et al.; "Fluorometric Determination of Amyloid Fibrils in Vitro Using the Fluorescent Dye, Thioflavine T1;" Analytical Biochemistry; 1989; pp. 244-249; vol. 177.
Levine III.; "Quantification of b-Sheet Amyloid Fibril Structures with Thioflavin T;" Methods in Enzymology; 1999; pp. 274-284; vol. 309.
Apr. 10, 2019 Search Report issued in International Application No. PCT/EP2018/084066.
Apr. 3, 2019 Search Report issued in International Application No. PCT/EP2018/084064.
Apr. 10, 2019 Search Report issued in International Application No. PCT/EP2018/084065.
U.S. Appl. No. 16/213,707, filed Dec. 7, 2018 in the name of Chan et al.
U.S. Appl. No. 16/213,929, filed Dec. 7, 2018 in the name of Geissler et al.

* cited by examiner

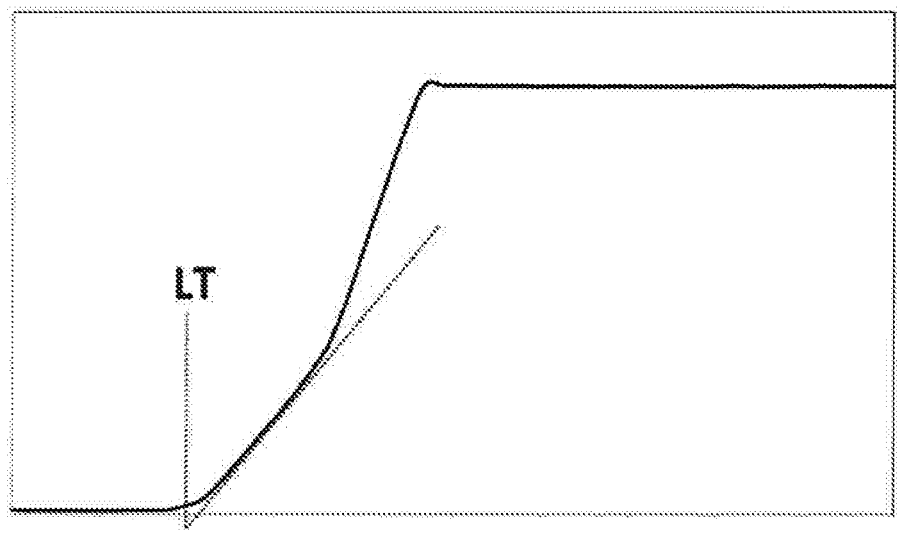

COMPOSITIONS IN THE FORM OF AN INJECTABLE AQUEOUS SOLUTION COMPRISING HUMAN GLUCAGON AND A CO-POLYAMINO ACID

Human glucagon is a short-acting hyperglycemic hormone which makes it possible to increase glycemia, thus correcting a hypoglycemic level that may result in excess insulin. It allows the release of glucose by stimulation of hepatic genoloysis, and it has the antagonist properties of insulin (hypoglycemic). Human glucagon is normally secreted by the alpha cells of the islets of Langerhans in the pancreas when hypoglycemia is detected.

Human glucagon is used for therapeutic purposes, such as the emergency treatment of severe hypoglycemia, also called "rescue", but also in a diagnostic framework during medical examinations, for example, to inhibit gastro-intestinal motility. Other applications are also contemplated for human glucagon, in particular, its use in a bi-hormonal system for the regulation of glycemia, also called artificial pancreas, and in congenital hyperinsulinism, which is a rare disease characterized by very high levels of insulin.

The clinical use of human glucagon has been limited due to some of its properties not being favorable to developing a stable pharmaceutical product intended for therapeutic use. In fact, human glucagon has very low solubility at physiological pH, high physical instability, due to its tendency to form fibrils over a broad pH range. It is for this reason that the only commercial products based on human glucagon (Glucagen®, NOVO NORDISK and Glucagon for injection, ELI LILLY) are in lyophilized forms for extemporaneous reconstitution.

The works of Onoue et al. (Pharm. Res. 2004, 21(7), 1274-83) demonstrated the potentially dangerous nature of these fibrils: since fibrillated human glucagon is cytotoxic to mammal cells in cultures.

Other than its physical instability, human glucagon undergoes various types of chemical deterioration. In aqueous solution, it deteriorates rapidly, forming several deterioration products. At least 16 deterioration products of human glucagon were identified by Kirsh et al. (International Journal of Pharmaceutics, 2000, 203, 115-125). The chemical deterioration of this human glucagon is therefore rapid and complex.

The poor chemical and physical stability of human glucagon in solution has led pharmaceutical companies such as NOVO NORDISK, ELI LILLY and, more recently, FRESENIUS KABI, to market this human glucagon in the form of a lyophilisate to bereconstituted at acidic pH (pH<3) just before injection. Human glucagon in the form of a lyophilisate is more stable, and the preparation of the formula at acidic pH just before use makes it possible to obtain a clear solution. However, once the product is reconstituted, it must be used quickly, because it undergoes an extremely rapid chemical and physical deterioration in the acidic reconstitution buffer, with the appearance of human glucagon fibrils within 24 hours following reconstitution, and/or a gelification of the composition. This presentation of the product is however unsatisfying because it requires a very rapid use of the formulation. This instability makes not only the use with a pump impossible, but it also involves the problem of resulting in significant losses of product in diagnostic use. In fact, since a composition of this type is only usable for a few hours after preparation, this causes waste.

Finally, even in the application of emergency treatment for sever hypoglycemic reactions, which may occur during insulin therapy in diabetic patients, the formulation to be reconstituted is not ideal, because it requires a lengthy and complicated preparation, for example, the patient information for GlucaGen® describes a 5 step process in order to prepare the recommended dose. Furthermore, a study by Locemia demonstrates that very few persons (about 10% of participants) who had to complete reconstitution in an emergency were able to deliver the appropriate dose. Finally, the pH of human glucagon solutions can cause pain upon injection into the patient.

Therefore, there is a need for a ready-to-use human glucagon solution. Today, the most advanced solutions, from the clinical point of view, which enable the delivery of human glucagon, circumvent the problem of stability of human glucagon in aqueous solution in different ways.

Locemia has perfected a spray of lyophilized human glucagon, currently being tested in a phase 3 clinical trial, which is intended to be administered intranasally. This spray is appropriate for a so-called "rescue" use, that is, in the case of severe hypoglycemia, because it is ready to use, and therefore easy to use, in contrast to solutions that must be prepared. However, this product is not suitable for use with a pump or for any use requiring precise control of the quantity of human glucagon delivered.

Xeris has developed a liquid formulation of human glucagon based on a polar, aprotic solvent, such as DMSO, currently being tested in clinical trials. However, if the injection of organic solvents solution for a "rescue" type use is envisaged, it is highly preferable to have an aqueous solution of human glucagon for chronic use. Compositions comprising an association with other peptides are contemplated, specifically amylin or a GLP-1 RA (Glucagon-like peptide-1 receptor agonist).

Finally, given the difficulties of human glucagon formulation, analogues of human glucagon are currently being developed by large pharmaceutical companies such as NOVO NORDISK, SANOFI OR ELI LILLY, in order to obtain formulations with stability that is compatible with pharmaceutical use. However, these peptides, for which the primary sequence was modified in comparison to the peptide of human origin may present a safety risk for patients.

Therefore, there is major interest in a solution making it possible to improve the solubilization and stability, both chemical and physical, of human glucagon in aqueous solution at a pH close to physiological pH, that is, from 6.0 to 8.0. This could make it possible to obtain a pharmaceutical product that is easier to use by the patient in the case of an emergency, but also to open the field to new therapeutic applications of human glucagon, such as, for example, its use in an artificial, bihormonal pancreas.

The prior art proposes solutions to attempt to solve this problem.

Certain documents propose to use basic pH. For example, US2015291680 teaches the solubilization of human glucagon at 1 mg/ml by using a pH from 8.8 to 9.4, and using ferrulic acid or tetrahydrocurcumin. However, in addition to the fact of using a basic pH, this solution presents the problem of leading to a very limited stability of human glucagon over time. The article by Jackson et al (Curr. Diab. Rep., 2012, 12, 705-710) proposes to formulate human glucagon at basic pH (about 10) in order to limit the formation of fibrils. However, this solution does not prevent a rapid chemical deterioration of human glucagon.

In contrast, application WO2014096440 (NOVOZYME) considers using a slightly acidic pH (about 5.5) in the presence of albumin and polysorbate, in order to improve stability by reducing the speed of fibrillation. However, this solution provides a limited improvement in stability. Most of the solutions described in the prior art making it possible to obtain a clear solution of human glucagon and to prevent the aggregation, gelification or precipitation of human glucagon involve the use of known tensioactives, detergents or solubilizing agents.

For example, Matilainen et al (J. Pharm. Sci, 2008, 97, 2720-2729 et Eur. J. Pharm. Sci., 2009, 36, 412-420) described the use of cyclodextrin in order to limit the rate of formation of human glucagon fibrils. However, the provided improvement seems insufficient for considering a use in a pump.

Among the proposed solutions are hydrophilic tensioactives:
- GB 1202607 (NOVO NORDISK) describes the use of anionic or cationic detergents;
- U.S. Pat. No. 6,384,016 (NOVO NORDISK) and US2011097386 (BIODEL) use lysophospholipids (or lysolecithins).
- WO2015095389 (AEGIS) describes non-ionic tensioactives, such as dodecyl maltoside, to improve the bioavailability of therapeutic agents, in the case of delivery by application to mucuses or epidermis, and in particular, in the case of ocular, nasal, oral or nasolacrymal delivery. This document describes that the presence of alkyl glycosides leads to an improvement in the absorption of human glucagon administered ocularly.
- the application WO2012059764 (ARECOR) describes cationic tensioactives, and more specifically, aromatic ammonium chlorides.

The tensioactives cited in the documents above may be too toxic or irritating for chronic subcutaneous use. For example, the lysophospholipids (or lysolecithins) are known to lyse red blood cells due to their hemolytic properties. At the time of subcutaneous injection, this may cause local damage to tissues and pain at the injection site. In the case of continuous injection by pump, this may lead to pain and/or irritation at the needle insertion site. International application WO2011138802 (Sun Pharma) describes a ready-to-use solution of human glucagon in aqueous micellar solution at a pH from 5 to 7.5 in the presence of a peglyated lipid (pegylated distearoyl-phosphotidylethanolamine). However, Garay et al. (Expert Opin Drug Deliv (2012) 9, 1319-1323) teach that Poly Ethylene Glycol is both immunogenic and antigenic. This could be harmful to patients with an anti-PEG antibody. Furthermore, Ganson et al. (J. Allergy Clin. Immunol. (2015) doi:10.1016/j.jaci.2015.10.034) describe that a clinical study regarding pegnivacogin coupled with methoxypolyethylene glycol (mPEG) of 40 kDa led to inflammatory response from the first dose of pegnivacogin in 3 of 640 patients. Of these three patients, two met the criteria for anaphylaxis and one had an isolated dermal reaction, each event was considered serious, and one was even considered life threatening to the patient. These adverse events caused the halting of the clinical trial and pose the problem of undesirable effects of pegyle compounds.

Document WO2013101749 (LATITUDE) describes nano-emulsions of human glucagon. However, it claims very modest yields in terms of chemical stability, that is, the composition comprises at least 75% of the initial concentration after 3-7 days at 37° C.

In addition, it must be noted that, to date, to the knowledge of the applicant, no pharmaceutical formulation comprising human glucagon in the form of an aqueous solution has been tested in clinical trials.

Therefore, there continues to be a need for a liquid, aqueous formulation at a pH close to physiological pH comprised from 6.0 to 8.0, making it possible to stabilize and obtain acceptable stability in human glucagon, both in terms of physical stability and of chemical stability. More specifically, there is a need for such a formulation which may be used in a bihormonal pump (insulin/human glucagon).

This need is even more obvious since Tan et al. (Diabetes, 2013, 62, 1131-138) demonstrated that combining human glucagon with a GLP-1 RA is an attractive proposal for the treatment of obesity and diabetes. However, being able to formulate human glucagon that is stable in aqueous solution at a pH close to physiological pH from 6.0 to 8.0 makes it possible, under the most favorable conditions, to be able to improve the stability of GLP-1 RAs that are sensitive to acid or basic conditions.

Co-polyamino acids bearing Hy carboxylate charges and hydrophobic radicals according to the invention have excellent resistance to hydrolysis. This may be specifically observed under accelerated conditions, for example, by hydrolysis testing at basic pH (pH 12).

In addition, forced oxidation tests, for example by Fenton oxidation process, show that co-polyamino acids bearing carboxylate charges and Hy hydrophobic radicals present adequate resistance to oxidation.

The invention also relates to physically stable compositions in the form of an injectable aqueous solution, for which the pH is comprised from 6.0 to 8.0, comprising at least:
a) human glucagon, and
b) a co-polyamino acid bearing carboxylate charges and hydrophobic radicals Hy, said co-polyamino acid being constituted of glutamic or aspartic units and said hydrophobic radicals Hy chosen among the radicals according to formula X as defined below:

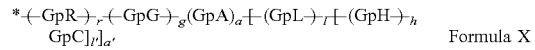

Formula X in which
GpR is chosen among the radicals according to formulas VII, VII' or VII":

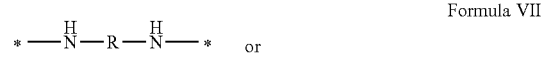

Formula VII

Formula VII'

Formula VII"

Identical or different GpG and GpH are chosen among the radicals according to formulas XI or XI';

Formula XI

Formula XI'

GpA is chosen among the radicals according to formula VIII

Formula VIII $$*\text{---NH---}A'\text{---[NH---]}_{s'}*$$
$$|$$
$$*$$

In which A' is chosen among the radicals according to formulas VIII', VIII" or VIII'''

$$\begin{array}{ccc} A_1 & & \\ \diagdown & & \\ & CO & A_1\text{---N---}A_2 \quad A_1\text{---N---}A_2\text{---N---}A_3 \\ \diagup & | & | \quad | \\ * & * & * \quad * \end{array}$$

Formula VIII' or Formula VIII" or Formula VIII'''

-GpL is chosen among the radicals according to formula XII

Formula XII $$\begin{array}{c} O \quad HN\text{---}* \\ \| \quad / \\ *\text{---}\!\!-\!\!A \\ \quad \backslash \\ \quad HN\text{---}* \end{array}$$

GpC is a radical according to formula IX;

Formula IX (structure shown)

* indicate the attachment sites of the different groups bound by amide functions;

a is an integer equal to 0 or to 1 and a'=1 if a=0 and a'=1, 2 or 3 if a=1;

a' is an integer equal to 1, to 2 or to 3;

b is an integer equal to 0 or to 1;

c is an integer equal to 0 or to 1, and if c is equal to 0, then d is equal to 1 or to 2;

d is an integer equal to 0, to 1 or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6;

l is an integer equal to 0 or to 1 and l'=1 if l=0 and l'=2 if l=1;

r is an integer equal to 0, 1 or to 2;

s' is an integer equal to 0 or to 1;

And if e is different from 0, then at least one of g, h or k is different from 0;

And if a=0, then l=0;

A, $A_1$, $A_2$ and $A_3$ identical or different, are linear or branched alkyl radicals comprising from 1 to 8 carbon atoms and, optionally, substituted by a radical from a saturated, unsaturated or aromatic ring;

B is a radical ether or polyether, unsubstituted, comprising from 4 to 14 carbon atoms and from 1 to 5 oxygen atoms, or a linear or branched alkyl radical, optionally comprising an aromatic ring, comprising from 1 to 9 carbon atoms;

$C_x$ is a linear or branched, alkyl radical optionally comprising a cyclic part, in which x indicates the number of carbon atoms, and:

When the hydrophobic radical -Hy bears 1 -GpC, then $9 \leq x \leq 25$,

When the hydrophobic radical -Hy bears 2 -GpC, then $9 \leq x \leq 15$,

When the hydrophobic radical -Hy bears 3 -GpC, then $7 \leq x \leq 13$,

When the hydrophobic radical -Hy bears 4 -GpC, then $7 \leq x \leq 11$,

When the hydrophobic radical -Hy bears at least 5 -GpC; $6 \leq x \leq 11$;

G is a branched alkyl radical of 1 to 8 carbon atoms, said alkyl radical bears one or more free carboxylic acid functions.

R is a radical chosen from the group constituted by a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and 1 to 5 oxygen atoms.

the hydrophobic radical(s)—Hy according to formula X being bound to the PLG:

via a covalent bond between a carbonyl of the hydrophobic radical -Hy and a nitrogen atom borne by the PLG, thus forming an amide function resulting from the reaction of an amine function borne by the PLG and an acid function borne by the precursor Hy' of the hydrophobic radical -Hy, and via a covalent bond between a nitrogen atom of the hydrophobic radical -Hy and a carbonyl borne by the PLG; thus forming an amide function resulting from the reaction of an amine function of the precursor -Hy' of the hydrophobic radical -Hy and an acid function borne by the PLG.

The ratio M between the number of hydrophobic radicals and the number of glutamic or aspartic unites being between $0 < M \leq 0.5$;

when several hydrophobic radicals are borne by a co-polyamino acid, then they are identical or different, The degree of DP polymerization in glutamic or aspartic units for the PLG chains is comprised from 5 to 250;

Free carboxylic acids being in the form of an alkaline cation salt chosen from the group constituted by $Na^+$ and $K^+$.

The invention also relates to a method for the preparation of stable, injectable compositions. By "soluble" is meant, suitable for the preparation of a clear solution, free of particles, at a concentration of less than 60 mg/ml in distilled water at 25° C.

By "solution" is meant a liquid composition free of visible particles, using the process according to EP 8.0 pharmacopoeia at point 2.9.20, and US pharmacopoeia <790>.

By "physically stable composition" is meant compositions which, after a certain period of storage at a certain temperature meet the visual inspection criteria described in the European, American and international pharmacopoeias, that is, compositions that are clear and that do not contain visible particles, but are also colorless.

By "chemically stable composition" is meant compositions which, after a certain period of storage at a certain temperature, show a minimum recovery of active ingredients and meet the applicable specifications for pharmaceutical products.

A classic method for measuring the stabilities of proteins or peptides consists of measuring the formation of fibrils using Thioflavin T, also called ThT. This method makes it possible to measure the lag time before the formation of fibrils by measuring the increase in fluorescence, and to do so under temperature and stirring conditions that make an acceleration of the phenomenon possible. Compositions according to the invention have a latency period before the formation of fibrils that is clearly greater than that of glucagon at the target pH.

By "injectable aqueous solution" is meant water-based solutions which meet the conditions of the EP and US pharmacopoeias, and which are sufficiently liquid to be injected.

By "co-polyamino acid being constituted of glutamic or aspartic units" non-cyclic linear chains of glutamic acid or aspartic acid units bound to each other by peptide bonds, said chains presenting a C-terminal part, corresponding to the carboxylate acid at one extremity, and an N-terminal part, corresponding to the amine at the other extremity of the chain.

By "alkyl radical" is meant a linear or branched carbon chain which does not comprise a heteroatom.

The co-polyamino acid is a statistical or bloc co-polyamino acid.

The co-polyamino acid is a statistical co-polyamino acid in the chain of glutamic and/or aspartic units.

All attachments between the different GpR, GpA, GpL, GpG and GpC groups are amide functions.

The Hy, GpR, GpA, GpL, GpG and GpC, and D radicals are each independently identical or different from one monomer to another.

When the co-polyamino acid comprises one or more aspartic units, the latter may undergo structural rearrangements.

By "alkyl radical" is meant a linear or branched carbon chain, which does not comprise a heteroatom.

The co-polyamino acid is a statistical co-polyamino acid in the chain of glutamic and/or aspartic units.

In the formulas the * indicate the binding sites of the different elements represented.

In one embodiment, the composition according to the invention is characterized in that Hy comprises from 15 to 100 carbon atoms.

In one embodiment, the composition according to the invention is characterized in that Hy comprises from 30 to 70 carbon atoms.

In one embodiment, the composition according to the invention is characterized in that Hy comprises from 40 to 60 carbon atoms.

In one embodiment, the composition according to the invention is characterized in that Hy comprises from 20 to 30 carbon atoms.

In one embodiment, said at least one hydrophobic radical -Hy is chosen among the radicals according to formula X as defined below:

*—[(GpR)—$_r$—(GpG)—$_g$(GpA)$_a$—[(GpL)—$_l$—[(GpH)—$_h$ GpC]$_r$]$_{a'}$  Formula X wherein GpC is a radical according to formula IX in which e=0 and GpC is a radical according to formula IXa:

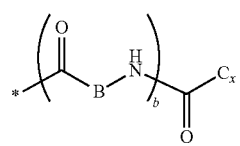

Formula IXa

In one embodiment, said at least one hydrophobic radical -Hy is chosen among the radicals according to formula X as defined below:

*—[(GpR)—$_r$—(GpG)—$_g$(GpA)$_a$—[(GpL)—$_l$—[(GpH)—$_h$ GpC]$_r$]$_{a'}$  Formula X wherein GpC is a radical according to formula IX in which e=1, b=0 and GpC is a radical according to formula IXd:

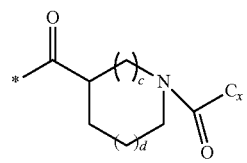

Formula IXd

In one embodiment, said at least one hydrophobic radical -Hy is chosen among the radicals according to formula X as defined below:

*—[(GpR)—$_r$—(GpG)—$_g$(GpA)$_a$—[(GpL)—$_l$—[(GpH)—$_h$GpC]$_r$]$_{a'}$  Formula X in which GpC is a radical according to formula IX in which e=1 and GpC is a radical according to formula IXb:

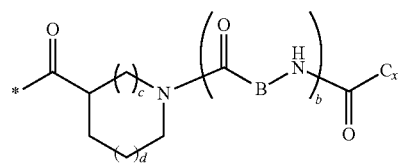

Formula IXb

In one embodiment, at least one of g, h or l is different from 0.

In one embodiment, when r=2, then the GpR group bound to the PLG is chosen among the GpR according to formula VII.

In one embodiment, when r=2, then the GpR group bound to the PLG is chosen among the GpR according to formula VII and the second GpR is chosen among the GpR according to formula VII".

In one embodiment, when r=2, then the GpR group bound to the PLG is chosen among the GpR according to formula VII".

In one embodiment, when r=2, then the GpR group bound to the PLG is chosen among the GpR according to formula VII" and the second GpR is chosen among the GpR according to formula VII.

In one embodiment, a=0.
In one embodiment, g+h≥2.
In one embodiment, g is greater than or equal to 2 (g≥2).
In one embodiment, h is greater than or equal to 2 (h≥2).
In one embodiment, g+h≥2 and l is equal to 0 (a=l=0).
In one embodiment, g+h≥2 and b is equal to 0 (b=0).

In one embodiment, g or h is greater than or equal to 2 (g≥2) and b is equal to 0.

In one embodiment, g+h≥2, b is equal to 0 (b=0) and e is equal to 1 (e=1).

In one embodiment, g or h is greater than or equal to 2 (g≥2) b is equal to 0 (b=0) and e is equal to 1 (e=1).

In one embodiment, at least one of g, h or l is different from 0.

In one embodiment, at most one of g, h or l is different from 0.

In one embodiment, at least one of g or h is equal to 1.

In one embodiment, a=1 and l=1.

In one embodiment, if l=0, at least one of g or h is equal to 0.

In one embodiment, if l=1, at least one of g and h is equal to 0.

In one embodiment, said at least one hydrophobic radical -Hy is chosen among the radicals according to formula X in which r=2 according to formula Xc', as defined below:

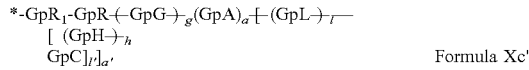

Formula Xc' in which GpR$_1$ is a radical according to formula according to formula VII.

Formula VII in which GpR, GpG, GpA, GpL, GpH, GpC, R, a, a', g, h, l and l' have the definitions given above.

In one embodiment, said at least one hydrophobic radical -Hy is chosen among the radicals according to formula X in which r=2 according to formula Xc', as defined below:

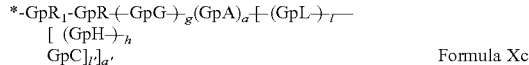

Formula Xc in which GpR$_1$ is a radical according to formula VII".

Formula VII"

in which GpR, GpG, GpA, GpL, GpH, GpC, R, a, a', g, h, l and l' have the definitions given above.

In one embodiment, said at least one hydrophobic radical -Hy is chosen among the radicals according to formula X in which:
l=0,
according to formula Xb' as defined below.

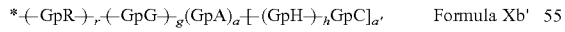

Formula Xb' in which
GpR is chosen among the radicals according to formulas VII, VII' or VII":

Formula VII or

Formula VII' or

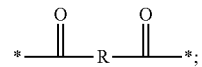

Formula VII"

GpG is chosen among the radicals according to formulas XI or XI':

Formula XI

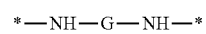

Formula XI'

GpA is chosen among the radicals according to formula VIII in which s'=1 represented by formula VIIIa or formula VIII in which s'=0 represented by formula VIIIb:

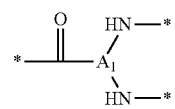

Formula VIIIa

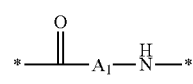

Formula VIIIb

GpC is a radical according to formula IX:

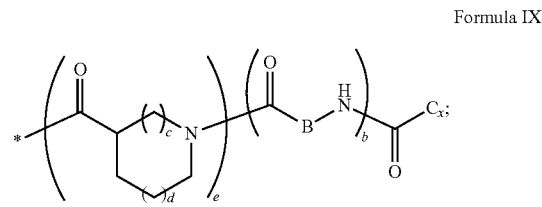

Formula IX

* indicate the attachment sites of the different groups linked by amide functions;
a is an integer equal to 0 or to 1 and a'=1 if a=0 and a'=1 or a'=2 if a=1;
a' is an integer equal to 1 or to 2 and;
  If a' is equal to 1 then a is equal to 0 or to 1 and GpA is a radical according to formula VIIIb and,
  If a' is equal to 2 then a is equal to 1 and GpA is a radical according to formula VIIIa;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 0, 5 or to 6, r is an integer equal to 0, 1 or to 2; and
s' is an integer equal to 0 or to 1;
And if e is different from 0, then at least one of g or h is different from 0;
A$_1$ is a linear or branched alkyl radical comprising from 1 to 8 carbon atoms and, optionally substituted by a radical from a saturated, unsaturated or aromatic ring;

B is a radical ether or polyether, unsubstituted, comprising 4 to 14 carbon atoms and 1 to 5 oxygen atoms, or a linear or branched alkyl radical, optionally comprising an aromatic ring, comprising from 1 to 9 carbon atoms;

$C_x$ is a linear or branched, monovalent alkyl radical optionally comprising a cyclic part, in which x indicates the number of carbon atoms, and:
when the hydrophobic radical -Hy bears 1 -GpC; $9 \leq x \leq 25$,
when the hydrophobic radical -Hy bears 2 -GpC; $9 \leq x \leq 15$,
when the hydrophobic radical -Hy bears 3 -GpC; $7 \leq x \leq 13$,
when the hydrophobic radical -Hy bears 4 -GpC; $7 \leq x \leq 11$,
when the hydrophobic radical -Hy bears at least 5 -GpC; $6 \leq x \leq 11$;

G is a branched alkyl radical of 1 to 8 carbon atoms, said alkyl radical bears one or more free carboxylic acid functions.

R is a radical chosen from the group constituted by a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising 4 to 14 carbon atoms and 1 to 5 oxygen atoms.

the hydrophobic radical(s) Hy according to formula X being bound to the PLG:
via a covalent bond between a carbonyl of the hydrophobic radical and a nitrogen atom borne by the PLG, thus forming an amide function resulting from the reaction of an amine function borne by the PLG and an acid function borne by the precursor of the hydrophobic radical, and
via a covalent bond between a nitrogen atom of the hydrophobic radical and a carbonyl borne by the PLG. thus forming an amide function resulting from the reaction of an amine function of the precursor -Hy' of the hydrophobic radical and an acid function borne by the PLG.

The ratio M between the number of hydrophobic radicals and the number of glutamic or aspartic unites being between $0 < M \leq 0.5$;

When several hydrophobic radicals are borne by a copolyamino acid, then they are identical or different, The degree of polymerization DP in glutamic or aspartic units for the PLG chains is comprised from 5 to 250;

Free carboxylic acids being in the form of an alkaline cation salt chosen from the group consisting of $Na^+$ and $K^+$.

In one embodiment said at least one hydrophobe -Hy is chosen among the radicals according to formula X, as defined below, in which l=0,
GpA is chosen among the radicals according to formula VIII in which s'=1 and A' is chosen among the radicals according to formulas VIII" or VIII'";

*—(GpR)$_r$—(GpG)$_g$(GpA)$_a$—(GpH)$_h$GpC]$_{a'}$   Formula Xd' in which
GpR is chosen among the radicals according to formula VII, VII' or VII":

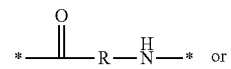

Formula VII

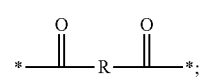

Formula VII'

Formula VII"

GpG is chosen among the radicals according to formula XI or XI':

Formula XI

*—NH—G—NH—*   Formula XI'

GpA is chosen among the radicals according to formula VIIIc or VIIId:

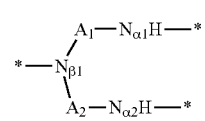

Formula VIIIc

Formula VIIId

GpC is a radical according to formula IX:

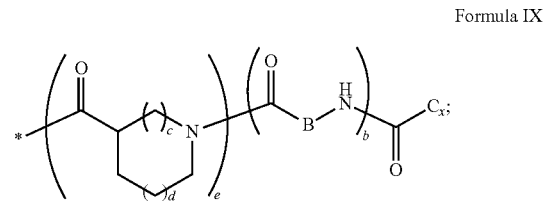

Formula IX

* indicate the attachment sites of the different groups bound by amide functions;
a is an integer equal to 0 or to 1 and a'=1 if a=0 and a'=2 or 3, if a=1;
a' is an integer equal to 2 or to 3 and;
if a' is equal to 1 then a is equal to 0 and
if a' is equal to 2 or 3, then a is equal to 1 and GpA is a radical according to formula VIIIc or VIIId;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6;

r is an integer equal to 0, 1 or to 2, and
s' is an integer equal to 1;
And if e is different from 0, then at least one of g or h is different from 0;
$A_1$, $A_2$, $A_3$, identical or different, are linear or branched alkyl radicals comprising 1 to 8 carbon atoms and, possibly, substituted by a radical from a saturated, unsaturated or aromatic ring;
B is a radical ether or polyether, unsubstituted, comprising 4 to 14 carbon atoms and 1 to 5 oxygen atoms, optionally comprising an aromatic ring, comprising 1 to 9 carbon atoms;
$C_x$ is a linear or branched, alkyl radical optionally comprising a cyclic part, in which x indicates the number of carbon atoms, and:
when the hydrophobic radical -Hy bears 1 -GpC; $9 \leq x \leq 25$,
when the hydrophobic radical -Hy bears 2 -GpC; $9 \leq x \leq 15$,
when the hydrophobic radical -Hy bears 3 -GpC; $7 \leq x \leq 13$,
when the hydrophobic radical -Hy bears 4 -GpC; $7 \leq x \leq 11$,
when the hydrophobic radical -Hy bears at least 5 -GpC, then $6 \leq x \leq 11$.
the hydrophobic radical(s) Hy according to formula X being bound to the PLG:
via a covalent bond between a carbonyl of the hydrophobic radical and a nitrogen atom borne by the PLG, thus forming an amide function resulting from the reaction of an amine function borne by the PLG and an acid function borne by the precursor Hy' of the hydrophobic radical -Hy, and
via a covalent bond between a nitrogen atom of the hydrophobic radical and a carbonyl borne by the PLG. thus forming an amide function resulting from the reaction of an amine function of the precursor -Hy' of the hydrophobic radical and an acid function borne by the PLG.
G is an alkyl radical from 1 to 8 carbon atoms, which alkyl radical bears one or more free carboxylic acid functions.
R is a radical chosen from the group constituted by a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and from 1 to 5 oxygen atoms.
the ratio M between the number of hydrophobic radicals and the number of glutamic or aspartic unites being between $0 < M \leq 0.5$;
When several hydrophobic radicals are borne by a co-polyamino acid, then they are identical or different,
The degree of polymerization DP in glutamic or aspartic units for the PLG chains is comprised from 5 to 250;
Free carboxylic acids being in the form of an alkaline cation salt chosen from the group consisting of $Na^+$ and $K^+$.

In one embodiment, when a'=1, x is comprised from 11 to 25 ($11 \leq x \leq 25$). Specifically, when x is comprised from 15 to 16 (x=15 or 16), then r=1 and R is an ether or polyether radical and when x is greater than 17 ($x \geq 17$), then r=1 and R is an ether or polyether radical.

In one embodiment, when a'=2, x is comprised from 9 to 15 ($9 \leq x \leq 15$).

In one embodiment, said at least one hydrophobic radical -Hy is chosen among the radicals according to formula X in which a=1 and a'=1 according to formula Xa, as defined below:

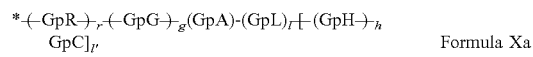

Formula Xa in which GpA is a radical according to formula VIII and A' is chosen among the radicals according to formula VIII' with s'=0 and GpA is a radical according to formula VIIIb.

Formula VIIIb and GpR, GpG, GpL, GpH, GpC, $A_1$, r, g, h, l and l' have the definitions given above.

In one embodiment, said at least one hydrophobic radical -Hy is chosen among the radicals according to formula X in which a=1 according to formula Xb, as defined below:

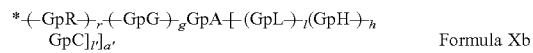

Formula Xb in which GpA is a radical according to formula VIII and A' is chosen among the radicals according to formula VIII' with s'=1 and GpA is a radical according to formula VIIIa.

Formula VIIIa

And GpR, GpG, GpL, GpH, GpC, $A_1$, a', r, g, h, l and l' have the definitions given above.

In one embodiment, said at least one hydrophobic radical -Hy is chosen among the radicals according to formula X in which a=1 as defined below:

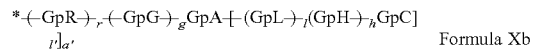

Formula Xb in which GpA is a radical according to formula VIII and A is chosen among the radicals according to formula VIII" with s'=1 and GpA is a radical according to formula VIIIc.

Formula VIIIc

And GpR, GpG, GpL, GpH, GpC, $A_1$, $A_2$, r, g, h, a', l and l' have the definitions given above.

In one embodiment, said at least one hydrophobic radical -Hy is chosen among the radicals according to formula X in which a=1 as defined below:

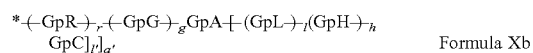

Formula Xb in which GpA is a radical according to formula VIII and A is chosen among the radicals according to formula VIII''' with s'=1, and GpA is a radical according to formula VIIId.

Formula VIIId

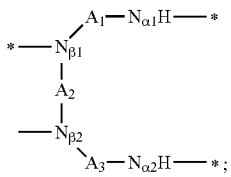

And GpR, GpG, GpL, GpH, GpC, $A_1$, $A_2$, $A_3$, a', r, g, h, l and l' have the definitions given above.

In one embodiment, said at least one hydrophobic radical -Hy is chosen among the radicals according to formula X in which r=1 according to formula Xc, as defined below:

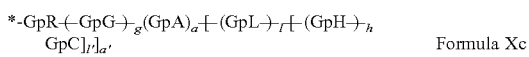

Formula Xc in which GpR is a radical according to formula VII:

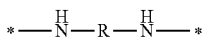

Formula VII

And GpR, GpA, GpL, GpH, GpC, R, a, g, h, l, a' and l' have the definitions given above.

In one embodiment, said at least one hydrophobic radical -Hy is chosen among the radicals according to formula X in which r=1 according to formula Xc, as defined below:

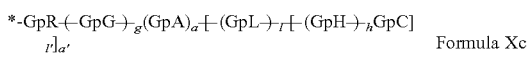

Formula Xc in which GpR is a radical according to formula VII':

Formula VII'

And GpR, GpA, GpL, GpH, GpC, R, a, g, h, l, a' and l' have the definitions given above.

In one embodiment, said at least one hydrophobic radical -Hy is chosen among the radicals according to formula X in which r=1 according to formula Xc, as defined below:

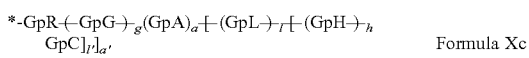

Formula Xc in which GpR is a radical according to formula VII'':

Formula VII''

And GpR, GpA, GpL, GpH, GpC, R, a, g, h, l, a' and l' have the definitions given above.

In one embodiment, said at least one hydrophobic radical -Hy is chosen among the radicals according to formula X in which r, g, a, l, h are equal to 0, according to formula Xd as defined below:

*-GpC      Formula Xd in which GpC is a radical according to formula IX in which e=0, b=0 and GpC is a radical according to formula IXc:

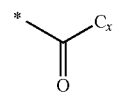

IXc

In one embodiment, the composition according to the invention is characterized in that said hydrophobic radicals are chosen among the hydrophobic radicals according to formula X in which GpA is a radical according to formula VIIIb, a'=1 and l=0 represented by formula Xe below.

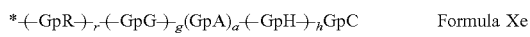 Formula Xe

GpR, GpG, GpA, GpH, GpC, r, g, h, l and l' have the definitions given above.

In one embodiment, the composition according to the invention is characterized in that said hydrophobic radicals are chosen among the hydrophobic radicals according to formula X in which a'=2 and a=1 and l=0 represented by formula Xf below:

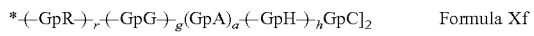 Formula Xf

GpR, GpG, GpA, GpH, GpC, r, g and h have the definitions given above.

In one embodiment, the composition according to the invention is characterized in that said hydrophobic radicals are chosen among the hydrophobic radicals according to formula X in which h=0, l=0 and l'=1 represented by formula Xg below:

 Formula Xg

GpR, GpG, GpA, GpC, r, g, a and a have the definitions given above.

In one embodiment, the composition according to the invention is characterized in that said hydrophobic radicals are chosen among the hydrophobic radicals according to formula X in which h=0, a'=1 represented by formula Xh below:

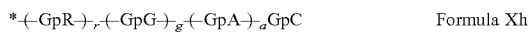 Formula Xh

GpR, GpG, GpA, GpC, r, a and g have the definitions given above.

In one embodiment, the composition according to the invention is characterized in that said hydrophobic radicals are chosen among the hydrophobic radicals according to formula X in which h=0, a'=2 and a=1 represented by formula Xg below:

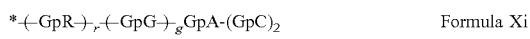 Formula Xi

GpR, GpG, GpA, GpC, r and g have the definitions given above.

In one embodiment, a=0,
In one embodiment, h=1 and g=0,
In one embodiment, h=0 and g=1,
In one embodiment, r=0, g=1 and h=0.
In one embodiment, r=1 and GpR is chosen among the radicals according to formula VII' or VII'' and h=0.
In one embodiment, r=1, g=0 and GpR is a radical according to formula VII' and h=0.

In one embodiment, r=1, g=0 and GpR is a radical according to formula VII' and h=1.

In one embodiment, r=1, g=0, GpR is a radical according to formula VII', GpA is chosen among the radicals according to formula VIIIa or VIIIb, and h=0.

In one embodiment, r=1, g=0, GpR is a radical according to formula VII', GpA is chosen among the radicals according to formula VIIIa or VIIIb and h=1.

In one embodiment, r=1, g=0 and GpR is a radical according to formula VII', GpA is a radical according to formula VIIIa and h=0.

In one embodiment, r=1, g=0, GpR is a radical according to formula VII', GpA is a radical according to formula VIIIa and h=1.

In one embodiment, r=1, g=0, GpR is a radical according to formula VII', GpA is a radical according to formula VIIIb and h=0.

In one embodiment, r=1, g=0, GpR is a radical according to formula VII', GpA is a radical according to formula VIIIb and h=1.

In one embodiment, r=0 and GpA is chosen among the radicals according to formulas VIIIa and VIIIb.

In one embodiment, r=0, g=0 and GpA is chosen among the radicals according to formulas VIIIa and VIIIb.

In one embodiment, r=0, GpA is chosen among the radicals according to formula VIIIa or VIIIb and h=0.

In one embodiment, the composition is characterized in that the hydrophobic radical according to formulas X, Xc', Xa, Xb, Xb', Xc, Xd', Xe, Xf, Xg, Xh and Xi is a radical in which R is a divalent, linear alkyl radical comprising from 2 to 12 carbon atoms.

In one embodiment, the composition is characterized in that the hydrophobic radical according to formulas X, Xc', Xa, Xb, Xb', Xc, Xd', Xe, Xf, Xg, Xh and Xi is a radical in which R is a divalent, linear alkyl radical comprising from 2 to 6 carbon atoms.

In one embodiment, the composition is characterized in that the hydrophobic radical according to formulas X, Xc', Xa, Xb, Xb', Xc, Xd', Xe Xf, Xg, Xh and Xi is a radical in which R is a linear divalent alkyl radical comprising from 2 to 6 carbon atoms.

In one embodiment, the composition is characterized in that the hydrophobic radical according to formulas X, Xc', Xa, Xb, Xb', Xc, Xd', Xe, Xf, Xg, Xh and Xi is a radical in which R is a divalent, linear alkyl radical comprising from 2 to 4 carbon atoms.

In one embodiment, the composition is characterized in that the hydrophobic radical according to formulas X, Xc', Xa, Xb, Xb', Xc, Xd', Xe, Xf, Xg, Xh and Xi is a radical in which R is a divalent, linear alkyl radical comprising from 2 to 4 carbon atoms.

In one embodiment, the composition is characterized in that the hydrophobic radical according to formulas X, Xc', Xa, Xb, Xb', Xc, Xd', Xe, Xf, Xg, Xh and Xi is a radical in which R is a divalent, linear alkyl radical comprising 2 carbon atoms.

In one embodiment, the composition is characterized in that the hydrophobic radical according to formulas X, Xc', Xa, Xb, Xb', Xc, Xd', Xe, Xf, Xg, Xh and Xi is a radical in which R is a divalent, linear alkyl radical comprising from 1 to 11 carbon atoms.

In one embodiment, the composition is characterized in that the hydrophobic radical according to formulas X, Xc', Xa, Xb, Xb', Xc, Xd', Xe, Xf, Xg, Xh and Xi is a radical in which R is a linear divalent alkyl radical comprising from 1 to 6 carbon atoms.

In one embodiment, the composition is characterized in that the hydrophobic radical according to formulas X, Xc', Xa, Xb, Xb', Xc, Xd', Xe, Xf, Xg, Xh and Xi is a radical in which R is a divalent, linear alkyl radical comprising from 2 to 5 carbon atoms and bearing one or more amide functions (—$CONH_2$).

In one embodiment, the composition is characterized in that the hydrophobic radical according to formulas X, Xc', Xa, Xb, Xb', Xc, Xd', Xe, Xf, Xg, Xh and Xi is a radical in which R is a divalent, linear alkyl radical comprising from 2 to 5 carbon atoms and bearing one or more amide functions (—$CONH_2$).

In one embodiment, the composition is characterized in that the hydrophobic radical according to formulas X, Xc', Xa, Xb, Xb', Xc, Xd', Xe, Xf, Xg, Xh and Xi is a radical in which R is a is a radical chosen from the group consisting of the radicals represented by the formulas below:

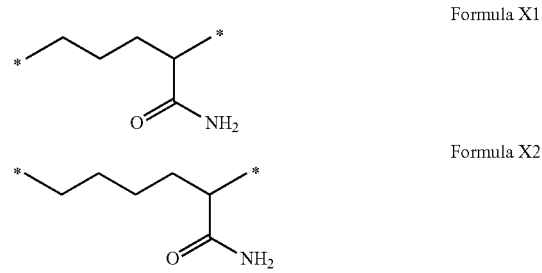

Formula X1

Formula X2

In one embodiment, the composition is characterized in that the hydrophobic radical according to formulas X, Xc', Xa, Xb, Xb', Xc, Xd', Xe, Xf, Xg, Xh and Xi is a radical in which R is a radical according to formula X1.

In one embodiment, the composition is characterized in that the hydrophobic radical according to formulas X, Xc', Xa, Xb, Xb', Xc, Xd', Xe, Xf, Xg, Xh and Xi is a radical in which R is a radical according to formula X2.

In one embodiment, the composition is characterized in that the hydrophobic radical according to formula X is a radical in which R is bound to the co-polyamino acid via an amide function borne by the carbon in delta or epsilon position (or in position 4 or 5) with respect to the amide function (—CONH2).

In one embodiment, the composition is characterized in that the hydrophobic radical according to formulas X, Xc', Xa, Xb, Xb', Xc, Xd', Xe, Xf, Xg, Xh and Xi is a radical in which R is an unsubstituted linear ether or polyether radical comprising from 4 to 14 carbon atoms and from 1 to 5 oxygen atoms.

In one embodiment, the composition is characterized in that the hydrophobic radical according to formulas X, Xc', Xa, Xb, Xb', Xc, Xd', Xe, Xf, Xg, Xh and Xi is a radical in which R is an ether radical.

In one embodiment, the composition is characterized in that the hydrophobic radical according to formulas X, Xc', Xa, Xb, Xb', Xc, Xd', Xe, Xf, Xg, Xh and Xi is a radical in which R is an ether radical represented by formula

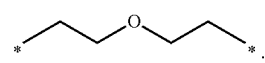

In one embodiment, the composition is characterized in that the hydrophobic radical according to formulas X, Xc', Xa, Xb, Xb', Xc, Xd', Xe, Xf, Xg, Xh et Xi is a radical in which R is an ether radical.

In one embodiment, the composition is characterized in that the hydrophobic radical according to formulas X, Xc', Xa, Xb, Xb', Xc, Xd', Xe, Xf, Xg, Xh and Xi is a radical in which R is a linear polyether radical comprising from 6 to 10 carbon atoms and from 2 to 3 oxygen atoms.

In one embodiment, the composition is characterized in that the hydrophobic radical according to formulas X, Xc', Xa, Xb, Xb', Xc, Xd', Xe, Xf, Xg, Xh et Xi is a radical in which R is a is a radical chosen from the group consisting of the radicals represented by the formulas below:

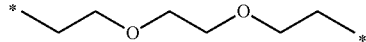

Formula X3

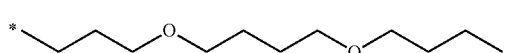

Formula X4

Formula X5

Formula X6

In one embodiment, the composition is characterized in that the hydrophobic radical according to formulas X, Xc', Xa, Xb, Xb', Xc, Xd', Xe, Xf, Xg, Xh and Xi is a radical in which R is a radical according to formula X3.

In one embodiment, the composition is characterized in that the hydrophobic radical according to formulas X, Xc', Xa, Xb, Xb', Xc, Xd', Xe, Xf, Xg, Xh and Xi is a radical in which R is a radical according to formula X4.

In one embodiment, the composition is characterized in that the hydrophobic radical according to formulas X, Xc', Xa, Xb, Xb', Xc, Xd', Xe, Xf, Xg, Xh and Xi is a radical in which R is a is a polyether radical chosen from the group consisting of the radicals represented by the formulas X5 and X6 below:

In one embodiment, the composition is characterized in that the hydrophobic radical according to formulas X, Xc', Xa, Xb, Xb', Xc, Xd', Xe, Xf, Xg, Xh and Xi is a radical in which R is a polyether radical according to formula X5.

In one embodiment, the composition is characterized in that the hydrophobic radical according to formulas X, Xc', Xa, Xb, Xb', Xc, Xd', Xe, Xf, Xg, Xh and Xi is a radical in which R is a polyether radical according to formula X6.

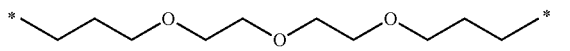

Formula X5

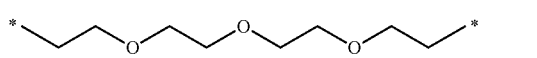

Formula X6

In one embodiment, the composition is characterized in that the hydrophobic radical according to formulas X, Xc', Xa, Xb, Xb', Xc, Xd', Xe, Xf, Xg, Xh and Xi is a radical in which the GpG and/or GpH radical is according to formula XI' in which G is an alkyl radical comprising 6 carbon atoms represented by formula Z below:

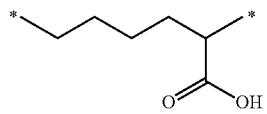

Formula Z

In one embodiment, the composition is characterized in that the hydrophobic radical according to formulas X, Xc', Xa, Xb, Xb', Xc, Xd', Xe, Xf, Xg, Xh and Xi is a radical in which the GpG and/or GpH radical is according to formula XI in which G is an alkyl radical comprising 4 carbon atoms represented by formula Z below:

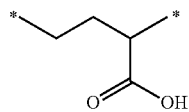

Formula Z'

In one embodiment, the composition is characterized in that the hydrophobic radical according to formulas X, Xc', Xa, Xb, Xb', Xc, Xd', Xe, Xf, Xg, Xh and Xi is a radical in which the GpG and/or GpH radical is according to formula XI in which G is an alkyl radical comprising 4 carbon atoms represented by —$(CH_2)_2$—$CH(COOH)$—.

In one embodiment, the composition is characterized in that the hydrophobic radical according to formulas X, Xc', Xa, Xb, Xb', Xc, Xd', Xe, Xf, Xg, Xh and Xi is a radical in which the GpG and/or GpH is according to formula XI in which G is an alkyl radical comprising 4 carbon atoms represented by —$CH((CH_2)_2COOH)$—.

In one embodiment, the composition is characterized in that the hydrophobic radical according to formulas X, Xc', Xa, Xb, Xb', Xc, Xd', Xe, Xf, Xg, Xh and Xi is a radical in which the GpG and/or GpH radical is according to formula XI in which G is an alkyl radical comprising 3 carbon atoms represented by formula —$CH_2$—$CH$—$(COOH)$.

In one embodiment, the composition is characterized in that the hydrophobic radical according to formulas X, Xc', Xa, Xb, Xb', Xc, Xd', Xe, Xf, Xg, Xh and Xii is a radical in which the GpG and/or GpH radical is according to formula XI in which G is an alkyl radical comprising 3 carbon atoms represented —$CH(CH_2)COOH$—.

In one embodiment, the composition is characterized in that the hydrophobic radical according to formulas X, Xc', Xa, Xb, Xb', Xc, Xd', Xe, Xf, Xg, Xh and Xi is a radical in which GpA radical is according to formula VIII and in which, $A_1$ is chosen from the group consisting of the radicals represented by the formulas below:

Formula Y1

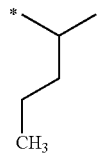

Formula Y2

-continued

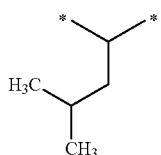
Formula Y3

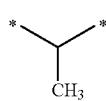
Formula Y4

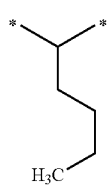
Formula Y5

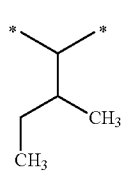
Formula Y6

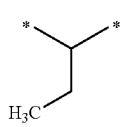
Formula Y7

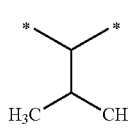
Formula Y8

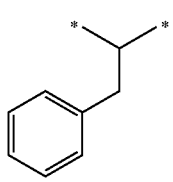
Formula Y9

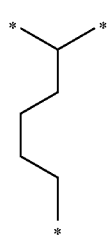
Formula Y10

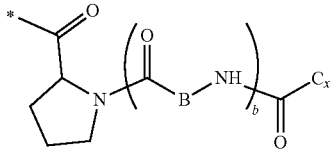
Formula IXe

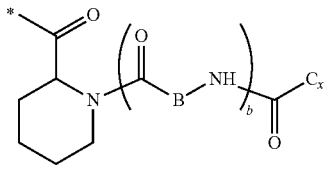
Formula IXf

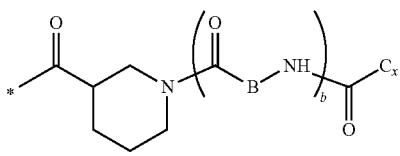
Formula IXg

In one embodiment, the composition is characterized in that the hydrophobic radical according to formulas X, Xc', Xd, Xa, Xb, Xb', Xc, Xd', Xe, Xf, Xg, Xh and Xi is a radical in which the radical GpC according to formula IX is chosen from the group consisting of the radicals according to formulas IXe, IXf or IXg, in which b is equal to 0, responding respectively to formulas IXh, IXi and IXj represented below:

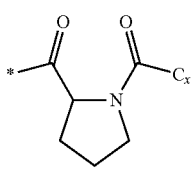
Formula IXh

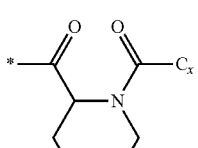
Formula IXi

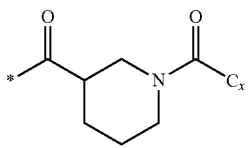
Formula IXj

In one embodiment, the composition is characterized in that the hydrophobic radical according to formulas X, Xc', Xd, Xa, Xb, Xb', Xc, Xd', Xe, Xf, Xg, Xh and Xi is a radical in which the GpC radical responds to the formula IX or IXe, in which b=0 and responds to the formula IXh.

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the linear alkyl radicals.

In one embodiment, the composition is characterized in that the hydrophobic radical according to formulas X, Xc', In one embodiment, the composition is characterized in that the hydrophobic radical according to formulas X, Xc', Xd, Xa, Xb, Xb', Xc, Xd', Xe, Xf, Xg, Xh and Xi is a radical in which the radical GpC according to formula IX is chosen from the group consisting of the radicals according to formulas according to formulas IXe, IXf or IXg represented below:

Xd, Xa, Xb, Xb', Xc, Xd', Xe, Xf, Xg, Xh and Xi is a radical in which Cx is chosen from the group consisting of the branched alkyl radicals.

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the alkyl radicals comprising from 19 to 14 carbon atoms.

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the radicals represented by the formulas below:

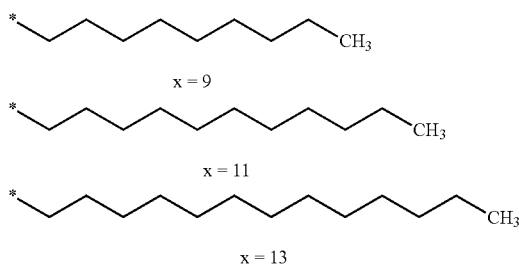

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the alkyl radicals comprising from 15 to 16 carbon atoms.

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the radicals represented by the formulas below:

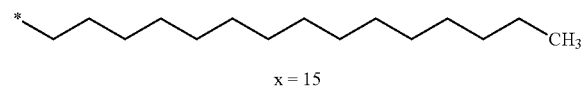 [SMILES: *CCCCCCCCCCCCCCC]

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the radicals represented by the formulas below:

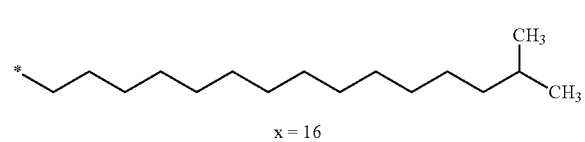 [SMILES: *CCCCCCCCCCCCCC(C)C]

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the alkyl radicals comprising from 17 to 25 carbon atoms.

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the alkyl radicals comprising from 17 to 18 carbon atoms.

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the radicals represented by the formulas below:

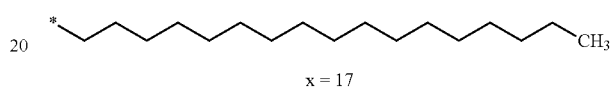

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the alkyl radicals comprising from 18 to 25 carbon atoms.

In one embodiment, the composition is characterized in that the hydrophobic radical according to formulas X, Xc', Xd, Xa, Xb, Xb', Xc, Xd', Xe, Xf, Xg, Xh and Xi is a radical in which Cx is chosen from the group consisting of the radicals represented by the formulas below:

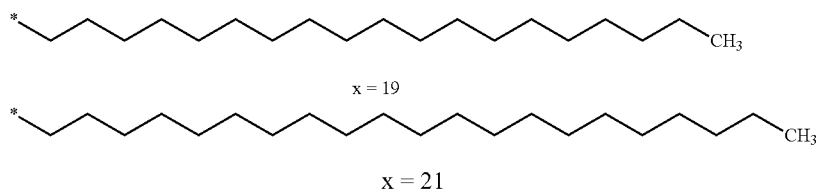

In one embodiment, the composition is characterized in that the hydrophobic radical according to formulas X, Xc', Xd, Xa, Xb, Xb', Xc, Xd', Xe, Xf, Xg, Xh and Xi is a radical in which the GpC radical according to formula IX is chosen from the group consisting of the alkyl radicals comprising from 14 to 15 carbon atoms.

In one embodiment, the composition is characterized in that the hydrophobic radical according to formulas X, Xc', Xd, Xa, Xb, Xb', Xc, Xd', Xe, Xf, Xg, Xh and Xi is a radical in which GpC radical according to formula IX is chosen from the group consisting of the radicals in which Cx is chosen from the group consisting of the radicals represented by the formulas below:

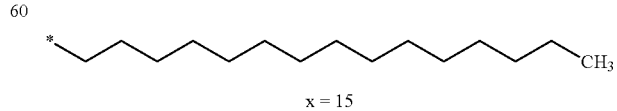

In one embodiment, r=0 and the hydrophobic radical according to formula X is bound to the PLG via a covalent bond between a carbonyl of the hydrophobic radical and a nitrogen atom borne by the PLG, thus forming an amide function resulting from the reaction of an amine function borne by the PLG precursor and an acid function borne by the precursor Hy' of the hydrophobic radical.

In one embodiment, r=1 or 2 and the hydrophobic radical according to formula X is bound to the PLG:
- via a covalent bond between a nitrogen atom of the hydrophobic radical and a carbonyl borne by the PLG, thus forming an amide function resulting from the reaction of an amine function of the precursor Hy' of the hydrophobic radical and an acid function borne by the PLG, or
- via a covalent bond between a carbonyl of the hydrophobic radical and a nitrogen atom borne by the PLG. thus forming an amide function resulting from the reaction of an acid function of the precursor -Hy' of the hydrophobic radical -Hy and an amine function borne by the PLG.

In one embodiment, if GpA is a radical according to formula VIIIc and r=1 or 2, then:
- the GpC are bound, directly or indirectly, to $N_{ll}$ and $N_{ll}$ and the PLG is bound, directly or indirectly, via GpR to $N_{ll}$, or
- the GpC are bound, directly or indirectly, to $N_{ll}$ and $N_{ll}$ and the PLG is bound, directly or indirectly, via GpR to $N_{ll}$, or
- the GpC are bound, directly or indirectly, to $N_{ll}$ and $N_{ff}$ and the PLG is bound, directly or indirectly, via GpR to $N_{ll}$.

In one embodiment, if GpA is a radical according to formula VIIIc and r=0, then:
- the GpC are bound, directly or indirectly, to $N_{ll}$ and $N_{ll}$ and the PLG is bound, directly or indirectly, to $N_{ff}$; or
- the GpC are bound, directly or indirectly, to $N_{ll}$ and $N_{ff}$ and the PLG is bound, directly or indirectly, to $N_{ll}$; or
- the GpC are bound, directly or indirectly, to $N_{ll}$ and $N_{ll}$, and the PLG is bound, directly or indirectly, to $N_{ff}$.

In one embodiment, if GpA is a radical according to formula VIIId and r=1 or 2, then
- the GpC are bound, directly or indirectly, to $N_{ff}$, $N_{ff}$ and N-- and the PLG is bound directly or indirectly, via GpR to $N_{ll}$; or
- the GpC are bound, directly or indirectly, to $N_{ll}$, $N_{ll}$ and N__ and the PLG is bound directly or indirectly, via GpR to $N_{ll}$; or
- the GpC are bound, directly or indirectly, to $N_{ll}$, $N_{ll}$ and N-- and the PLG is bound directly or indirectly, via GpR to $N_{ll}$; or
- the GpC are bound, directly or indirectly, to $N_{ll}$, $N_{ll}$ and N__ and the PLG is bound directly or indirectly, via GpR to $N_{ll}\square$.

In one embodiment, if GpA is a radical according to formula VIIId and r=0, then
- the GpC are bound, directly or indirectly, to $N_{ff}$, $N_{ll}$ and N-- and PLG is bound directly or indirectly, to $N_{ll}$; or
- the GpC are bound, directly or indirectly, to $N_{ff}$, $N_{ll}$ and N-- and PLG is bound directly or indirectly, to $N_{ll}$; or
- the GpC are bound, directly or indirectly, to $N_{ll}\square$, $N_{ll}$ and N and the PLG is bound, directly or indirectly, to $N_{ll}$; or
- The GpC are bound directly or indirectly to $N_{ff}$, $N_{ff}$ and N□ □ and the PLG is bound directly or indirectly to $N_{lll}$ In the formulas, the * indicate the attachment sites of the hydrophobic radicals to the PLG or between the different GpR, GpG, GpA, GpL and GpC to form amide functions.

The Hy radicals are attached to the PLG via amide functions.

In formulas VII, VII' and VII'', the * indicate, from left to right respectively, the GpR attachment sites:
- to the PLG and
- to GpR if r=2 or to GpG if g=1 or to GpA if g=0.

In formulas VIIIa, VIIIb, VIIIc and VIIId, the * indicate, from left to right respectively, the GpA attachment sites:
- to GpR if g=1 or to GpR if r=1 or 2, and g=0 or to the PLG if g=r=0 and
- To GpL if l=1 or to GpH if h=1 and l=0 or to GpC if l=h=0

In formula IX, the * indicates the attachment site of GpC:
- To GpH if h=1,
- To GpL if l=1 and h=0,
- To GpA if a=1 and h=l=0,
- To GpG if g=1 and h=l=a=0.

The Hy, GpR, GpG, GpA, GpH, GpL and GpC radicals are each independently identical or different from one residue to another.

In one embodiment, the composition is characterized in that the M ratio between the number of hydrophobic radicals and the number of glutamic or aspartic units is comprised from 0.02 to 0.2.

In one embodiment, the composition is characterized in that the pH is comprised from 6.6 to 7.8.

In one embodiment, the composition is characterized in that the pH is comprised from 7.0 to 7.8.

In one embodiment, the composition is characterized in that the pH is comprised from 6.8 to 7.4.

In one embodiment, the composition is characterized in that the co-polyamino acid bearing carboxylate charges and hydrophobic radicals is chosen among the co-polyamino acids according to formula XXX below:

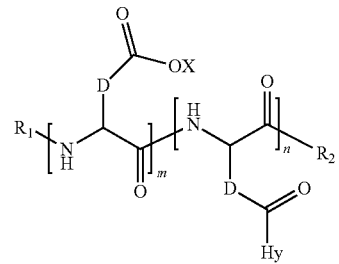

Formula XXX in which,
- D represents, independently, either a —CH$_2$— group (aspartic unit) of a —CH$_2$—CH$_2$— group (glutamic unit),
- Hy is a hydrophobic radical chosen among the hydrophobic radicals according to formula X, in which r=1 and GpR is a radical according to formula VII.
- $R_1$ is a hydrophobic radical chosen among the hydrophobic radicals according to formula X in which r=0 or r=1 and GpR is a radical according to formula VII', or a radical chosen from the group consisting of a H, a linear acyl group in C2 to C10, a branched acyl group in C3 to C10, a benzyl, a terminal "amino acid" unit and a pyroglutamate,
- $R_2$ is a hydrophobic radical chosen among the hydrophobic radicals according to formula X in which r=1 and GpR is a radical according to formula VII or an —NR'R'', R' and R'' radical, identical or different, being chosen from the group consisting of H, the linear or branched or cyclic alkyls in C2 to C10, the benzyl and said R' and R" alkyls which may form together one or more saturated, unsaturated and/or aromatic rings and/or may comprise heteroatoms, chosen from the group consisting of O, N and S, X represents a H or a cationic entity chosen from the group comprising the metallic cations;

n+m represents the degree of polymerization DP of the co-polyamino acid, that is the average number of monomeric units per co-polyamino acid chain and $5 \leq n+m \leq 250$;

The co-polyamino acid bearing carboxylate charges and at least one hydrophobic radical according to formula X may also be called "co-polyamino acid" in this description.

In one embodiment, the composition according to the invention is characterized in that the co-polyamino acid bearing carboxylate charges and hydrophobic radicals is chosen among the co-polyamino acids according to formula XXX in which $R_1$ is a hydrophobic radical according to formula X and $R_2$ is a —NR'R" radical, R' and R" being as defined above.

In one embodiment, the composition according to the invention is characterized in that the co-polyamino acid bearing carboxylate charges and hydrophobic radicals is chosen among the co-polyamino acids according to formulas XXX, in which $R_1$ is a hydrophobic radical according to formula X and $R_2$ is a —NR'R" radical, R' and R" being as defined above and Hy is a radical according to formula X in which $r=1$.

In one embodiment, the composition according to the invention is characterized in that the co-polyamino acid bearing carboxylate charges and hydrophobic radicals is chosen among the co-polyamino acids according to formulas XXX, in which $R_1$ is a hydrophobic radical according to formula X and $R_2$ is a —NR'R" radical, R' and R" being as defined above, and Hy is a radical according to formula X, in which $r=1$, and for GpC, $b=0$.

In one embodiment, the composition according to the invention is characterized in that the co-polyamino acid bearing carboxylate charges and hydrophobic radicals is chosen among the co-polyamino acids according to formula XXX, in which $R_2$ is a hydrophobic radical according to formula X.

In one embodiment, the composition according to the invention is characterized in that the co-polyamino acid bearing carboxylate charges and hydrophobic radicals is chosen among the co-polyamino acids according to formula XXX, in which $R_2$ is a hydrophobic radical according to formula X.

In one embodiment, the composition according to the invention is characterized in that the co-polyamino acid bearing carboxylate charges and hydrophobic radicals is chosen among the co-polyamino acids according to formula XXX in which $R_2$ is a hydrophobic radical according to formula X and $R_1$ is a —NR'R" radical, R' and R" being as defined above.

In one embodiment, the composition according to the invention is characterized in that the co-polyamino acid bearing carboxylate charges and hydrophobic radicals is chosen among the co-polyamino acids according to formulas XXX, in which $R_2$ is a hydrophobic radical according to formula X and $R_1$ is a —NR'R" radical, R' and R" being as defined above and Hy is a radical according to formula X in which $r=1$.

In one embodiment, the composition according to the invention is characterized in that the co-polyamino acid bearing carboxylate charges and hydrophobic radicals is chosen among the co-polyamino acids according to formulas XXX, in which $R_2$ is a hydrophobic radical according to formula X and $R_1$ is a —NR'R" radical, R' and R" being as defined above, and Hy is a radical according to formula X, in which $r=1$, and for GpC, $b=0$.

In one embodiment, the composition according to the invention is characterized in that the co-polyamino acid bearing carboxylate charges and hydrophobic radicals is chosen among the co-polyamino acids according to formula XXX, in which $R_1$ and $R_2$ are hydrophobic radicals according to formula X.

In one embodiment, the composition according to the invention is characterized in that the co-polyamino acid bearing carboxylate charges and hydrophobic radicals is chosen among the co-polyamino acids according to formula XXX, in which $R_1$ and $R_2$ are hydrophobic radicals according to formula X.

In one embodiment, the composition according to the invention is characterized in that the co-polyamino acid bearing carboxylate charges and hydrophobic radicals is chosen among the co-polyamino acids according to formula XXX in which $R_1$ and $R_2$ are hydrophobic radicals according to formula X, and Hy is a radical according to formula X, in which $r=1$.

In one embodiment, the composition according to the invention is characterized in that the co-polyamino acid bearing carboxylate charges and hydrophobic radicals is chosen among the co-polyamino acids according to formula XXX in which $R_1$ and $R_2$ are hydrophobic radicals according to formula X and Hy is a radical according to formula X, in which $r=1$, and for GpC, $b=0$.

In one embodiment, the composition is characterized in that the co-polyamino acid bearing carboxylate charges and hydrophobic radicals is chosen among the co-polyamino acids according to formula XXX, in which $R_2$ is a hydrophobic radical according to formula X in which $r=1$ and GpR is according to formula VII.

In one embodiment, the composition is characterized in that the co-polyamino acid bearing carboxylate charges and hydrophobic radicals is chosen among the co-polyamino acids according to formulas XXX, in which $R_2$ is a hydrophobic radical according to formula X in which $r=1$ and GpR is according to formula VII.

In one embodiment, the composition is characterized in that the co-polyamino acid bearing carboxylate charges and hydrophobic radicals is chosen among the co-polyamino acids according to formula XXX, in which $R_2$ is a hydrophobic radical according to formula X in which $r=1$ and GpR is according to formula VII and GpC is according to formula IX in which $b=0$, $c=0$ and $d=1$.

In one embodiment, the composition is characterized in that the co-polyamino acid bearing carboxylate charges and hydrophobic radicals is chosen among the co-polyamino acids according to formula XXX, in which $R_2$ is a hydrophobic radical according to formula X in which $r=1$ and GpR is according to formula VII and GpC is according to formula IX in which $b=0$, $c=0$, $d=1$ and $x=13$.

We call "statistical co-polyamino acid" a co-polyamino acid bearing carboxylate charges and at least one hydrophobic radical, a co-polyamino acid according to formula XXXa.

In one embodiment, the composition is characterized in that the co-polyamino acid bearing carboxylate charges and hydrophobic radicals is chosen among the co-polyamino acids according to formulas XXX, in which $R_1=R'_1$ and $R_2=R'_2$, according to formula XXXa below:

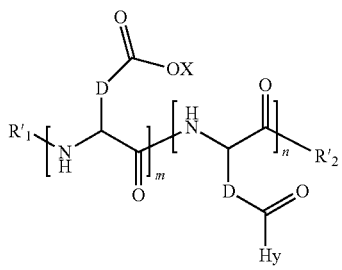

Formula XXXa in which, m, n, X, D and Hy have the definitions given above,

R'₁ is a radical chosen from the group consisting of a H, a linear acyl group in C2 to C10, a branched acyl group in C3 to C10, a benzyl, a terminal "amino acid" unit and a pyroglutamate, R'₂ is a hydrophobic radical chosen from the group consisting of H, the linear or branched or cyclic alkyls in C2 to C10, the benzyl and said R' and R" alkyls may form together one or more saturated, unsaturated and/or aromatic rings and/or may comprise heteroatoms, chosen from the group consisting of O, N and S, In one embodiment, the composition according to the invention is characterized in that the co-polyamino acid bearing carboxylate charges and hydrophobic radicals is chosen among the co-polyamino acids according to formula XXXa, in which Hy is a radical according to formula X.

In one embodiment, the composition according to the invention is characterized in that the co-polyamino acid bearing carboxylate charges and hydrophobic radicals is chosen among the co-polyamino acids according to formula XXXa, in which Hy is a radical according to formula X, in which r=1.

In one embodiment, the composition according to the invention is characterized in that the co-polyamino acid bearing carboxylate charges and hydrophobic radicals is chosen among the co-polyamino acids according to formula XXXa, in which Hy is a radical according to formula X in which r=1 and for GpR, b=0.

In one embodiment, the composition according to the invention is characterized in that the co-polyamino acid bearing carboxylate charges and hydrophobic radicals is chosen among the co-polyamino acids according to formula XXXa, in which Hy is a radical according to formula X, and in which GpC is a radical according to formula IX.

In one embodiment, the composition according to the invention is characterized in that the co-polyamino acid bearing carboxylate charges and hydrophobic radicals is chosen among the co-polyamino acids according to formula XXXa, in which Hy is a radical according to formula X, and in which GpC is a radical according to formula XI and r=1.

We call "defined co-polyamino acid" a co-polyamino acid bearing carboxylate charges and at least one hydrophobic radical, a co-polyamino acid according to formula XXXb.

In one embodiment, the composition is characterized in that the co-polyamino acid bearing carboxylate charges and hydrophobic radicals is chosen among the co-polyamino acids according to formula XXX, in which n=0, according to formula XXXb below:

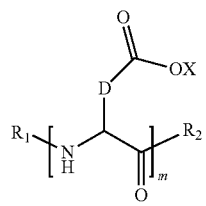

Formula XXXb in which m, X, D, R₁ and R₂ have the definitions given above and at least R₁ or R₂ is a hydrophobic radical according to formula X.

In one embodiment, the composition according to the invention is characterized in that the co-polyamino acid bearing carboxylate charges and hydrophobic radicals is chosen among the co-polyamino acids according to formula XXXb, in which R₁ or R₂ is a hydrophobic radical according to formula X.

In one embodiment, the composition according to the invention is characterized in that the co-polyamino acid bearing carboxylate charges and hydrophobic radicals is chosen among the co-polyamino acids according to formula XXXb in which R₁ is a hydrophobic radical according to formula X. In one embodiment, the composition according to the invention is characterized in that the co-polyamino acid bearing carboxylate charges and hydrophobic radicals is chosen among the co-polyamino acids according to formula XXXb in which R₂ is a hydrophobic radical according to formula X.

In one embodiment, the composition according to the invention is characterized in that the co-polyamino acid bearing carboxylate charges and hydrophobic radicals is chosen among the co-polyamino acids according to formula XXXb, in which R₂ is a hydrophobic radical according to formula X.

In one embodiment, the composition according to the invention is characterized in that the co-polyamino acid bearing carboxylate charges and hydrophobic radicals is chosen among the co-polyamino acids according to formula XXXb, in which R₂ is a hydrophobic radical according to formula X, in which r=0 and R₁ is a radical chosen from the group consisting of a H, a linear acyl group in C2 to C10, a branched acyl group in C3 to C10, a benzyl, a terminal "amino acid" unit and a pyroglutamate, In one embodiment, the composition according to the invention is characterized in that the co-polyamino acid bearing carboxylate charges and hydrophobic radicals is chosen among the co-polyamino acids according to formula XXXb, in which R₂ and Hy are hydrophobic radicals according to formula X, in which r=0 and for GpC, b=0 and R₁ is a radical chosen from the group consisting of a H, a linear acyl group in C2 to C10, a branched acyl group in C3 to C10, a benzyl, a terminal "amino acid" unit and a pyroglutamate, In one embodiment, the composition according to the invention is characterized in that when the co-polyamino acid comprises aspartate unites, then the co-polyamino acid may also comprise monomeric units according to formula XXXI and/or XXXI':

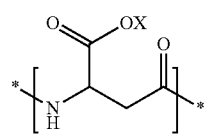

Formula XXXI

-continued

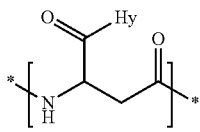

Formula XXXI'

In one embodiment, the composition is characterized in that the co-polyamino acid bearing carboxylate charges and hydrophobic radicals is chosen among the co-polyamino acids according to formula XXX below:

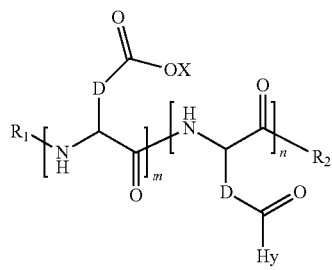

Formula XXX in which,
D represents, independently, either a —CH$_2$— group (aspartic unit) of a —CH$_2$—CH$_2$— group (glutamic unit),
Hy is a hydrophobic radical chosen among the hydrophobic radicals according to formula X, in which r=1 and GpR is a radical according to formula VII.
$R_1$ is a hydrophobic radical chosen among the hydrophobic radicals according to formula X in which r=0 or r=1 and GpR is a radical according to formula VII', or a radical chosen from the group consisting of a H, a linear acyl group in C2 to C10, a branched acyl group in C3 to C10, a benzyl, a terminal "amino acid" unit and a pyroglutamate,
$R_2$ is a hydrophobic radical chosen among the hydrophobic radicals according to formula X in which r=1 and GpR is a radical according to formula VII or an —NR'R", R' and R" radical, identical or different, being chosen from the group consisting of H, the linear, branched or cyclic alkyls in C2 to C10, the benzyl and said R' and R" alkyls may form together one or more saturated, unsaturated and/or aromatic rings and/or may comprise heteroatoms, chosen from the group consisting of O, N and S,
at least one of $R_1$ or $R_2$ is a hydrophobic radical as defined above.
X represents a cationic entity chosen from the group comprising the alkaline cations;
n≥1 and n+m represents the degree of polymerization DP of the co-polyamino acid, that is the average number of monomeric units per co-polyamino acid chain and 5≤n+m≤250;

In one embodiment, the co-polyamino acid is chosen from the co-polyamino acids of formula XXXb in which the hydrophobic radical -Hy is chosen from the group of hydrophobic radicals according to formula X, in which a'=1 and l'=1 and GpC is a radical according to formula IXe.

In one embodiment, the co-polyamino acid is chosen from the co-polyamino acids of formula XXXb in which the hydrophobic radical -Hy is chosen from the group of hydrophobic radicals according to formula X, in which a'=1 and l'=1 and GpC is a radical according to formula IX in which e=0.

In one embodiment, the co-polyamino acid is chosen from the co-polyamino acids of formula XXXb in which the hydrophobic radical -Hy is chosen from the group of hydrophobic radicals according to formula X in which a'=2 or l'=2 and GpC is a radical according to formula IXe.

In one embodiment, the co-polyamino acid is chosen from the co-polyamino acids of formula XXXb in which the hydrophobic radical -Hy is chosen from the group of hydrophobic radicals according to formula X, in which a'=2 and l'=2 and GpC is a radical according to formula IX in which e=0.

In one embodiment, the co-polyamino acid is chosen from the co-polyamino acids of formula XXXa in which the hydrophobic radical -Hy is chosen from the group of hydrophobic radicals according to formula X, in which a'=1 and l'=1 and GpC is a radical according to formula IXe.

In one embodiment, the co-polyamino acid is chosen from the co-polyamino acids of formula XXXa in which the hydrophobic radical -Hy is chosen from the group of hydrophobic radicals according to formula X in which a'=2 or l'=2 and GpC is a radical according to formula IXe.

The co-polyamino acid bearing carboxylate charges and at least one hydrophobic radical according to formula I may also be called "co-polyamino acid" in this description.

In one embodiment, the composition according to the invention is characterized in that the co-polyamino acid bearing carboxylate charges and hydrophobic radicals is chosen among the co-polyamino acids according to formula XXX in which n≥1 and at least one of $R_1$ or $R_2$ is a hydrophobic radical according to formula X.

In one embodiment, the composition according to the invention is characterized in that the co-polyamino acid bearing carboxylate charges and hydrophobic radicals is chosen among the co-polyamino acids according to formula XXX, in which n≥ and $R_1$ is a hydrophobic radical according to formula X.

In one embodiment, the composition according to the invention is characterized in that the co-polyamino acid bearing carboxylate charges and hydrophobic radicals is chosen among the co-polyamino acids according to formula XXX, in which n≥1 and $R_2$ is a hydrophobic radical according to formula X.

In one embodiment, the composition according to the invention is characterized in that the co-polyamino acid bearing carboxylate charges and hydrophobic radicals is chosen among the co-polyamino acids according to formula XXX, in which n≥1, $R_1$ is a hydrophobic radical according to formula X, in which r=0.

In one embodiment, the composition according to the invention is characterized in that the co-polyamino acid bearing carboxylate charges and hydrophobic radicals is chosen among the co-polyamino acids according to formula XXX, in which n≥1, $R_2$ is a hydrophobic radical according to formula X, in which r=1.

In one embodiment, the composition according to the invention is characterized in that the co-polyamino acid bearing carboxylate charges and hydrophobic radicals is chosen among the co-polyamino acids according to formula XXX in which $R_1$ is a hydrophobic radical according to formula X in which r=1, and for GpC, b=0 and $R_2$ is a —NR'R" radical, R' and R" being as defined above.

In one embodiment, the composition according to the invention is characterized in that the co-polyamino acid bearing carboxylate charges and hydrophobic radicals is chosen among the co-polyamino acids according to formula XXX, in which $R_2$ is a hydrophobic radical according to formula X, and $R_1$ is a radical chosen from the group consisting of a H, a linear acyl group in C2 to C10, a branched acyl group in C3 to C10, a benzyl, a terminal "amino acid" unit and a pyroglutamate, In one embodiment, the composition is characterized in that the co-polyamino acid bearing carboxylate charges and hydrophobic radicals is chosen among the co-polyamino acids according to formula XXX, in which at least one of $R_1$ or $R_2$ is a hydrophobic radical, specifically with n≥1, or XXXb in which the D group is a —$CH_2$— group (aspartic unit).

In one embodiment, the composition is characterized in that the co-polyamino acid bearing carboxylate charges and hydrophobic radicals is chosen among the co-polyamino acids according to formula XXX, in which at least one of $R_1$ or $R_2$ is a hydrophobic radical, specifically with n≥1, or XXXb in which the D group is a —$CH_2$—$CH_2$— group (glutamic unit).

In one embodiment, the composition is characterized in that the co-polyamino acid bearing carboxylate charges and hydrophobic radicals is chosen among the co-polyamino acids according to formula XXX, XXXa or XXXb, in which the D group is a —$CH_2$— group (aspartic unit).

In one embodiment, the composition is characterized in that the co-polyamino acid bearing carboxylate charges and hydrophobic radicals is chosen among the co-polyamino acids according to formula XXX, XXXa and XXXb, in which the D group is a —$CH_2$—$CH_2$— group (glutamic unit).

In one embodiment, the composition is characterized in that the M ratio between the number of hydrophobic radicals and the number of glutamic or aspartic units is comprised from 0.007 to 0.3.

In one embodiment, the composition is characterized in that the M ratio between the number of hydrophobic radicals and the number of glutamic or aspartic units is comprised from 0.01 to 0.3.

In one embodiment, the composition is characterized in that the M ratio between the number of hydrophobic radicals and the number of glutamic or aspartic units is comprised from 0.03 to 0.3.

In one embodiment, the composition is characterized in that the M ratio between the number of hydrophobic radicals and the number of glutamic or aspartic units is comprised from 0.02 to 0.2.

In one embodiment, the composition according to the invention is characterized in that n+m is comprised from 10 to 250.

In one embodiment, the composition is characterized in that n+m is comprised from 10 to 200.

In one embodiment, the composition is characterized in that n+m is comprised from 10 to 100.

In one embodiment, the composition is characterized in that n+m is comprised from 10 to 50.

In one embodiment, the composition is characterized in that n+m is comprised from 15 to 150.

In one embodiment, the composition is characterized in that n+m is comprised from 15 to 100.

In one embodiment, the composition is characterized in that n+m is comprised from 15 to 80.

In one embodiment, the composition is characterized in that n+m is comprised from 15 to 65.

In one embodiment, the composition is characterized in that n+m is comprised from 20 to 60.

In one embodiment, the composition is characterized in that n+m is comprised from 20 to 50.

In one embodiment, the composition is characterized in that n+m is comprised from 20 to 40.

The invention also relates to said co-polyamino acids bearing carboxylate charges and hydrophobic radicals according to formula I and the precursors of said hydrophobic radicals.

The co-polyamino acid bearing carboxylate charges and hydrophobic radicals according to formula X are soluble in distilled water at a pH from 6 to 8, at a temperature of 25° C. and at a concentration of less than 60 mg/ml.

In one embodiment, the invention also relates to the precursors of said hydrophobic radicals according to formula X.

The invention also relates to a co-polyamino acid bearing carboxylate charges and hydrophobic radicals Hy, chosen among the radicals according to formula X as defined below:

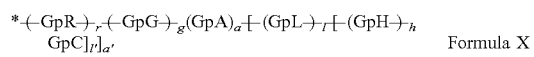

Formula X in which

GpR is chosen among the radicals according to formulas VII, VII' or VII":

Formula VII

Formula VII'

Formula VII"

Identical or different GpG and GpH are chosen among the radicals according to formulas XI or XI';

Formula XI

Formula XI'

GpA is chosen among the radicals according to formulas VIII

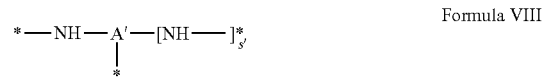

Formula VIII

In which A' is chosen among the radicals according to formulas VIII', VIII" or VIII'"

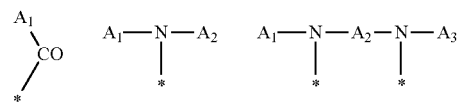

Formula VIII' or Formula VIII" or Formula VIII'"
-GpL is chosen among the radicals according to formula XII

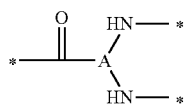

Formula XII

GpC is a radical according to formula IX:

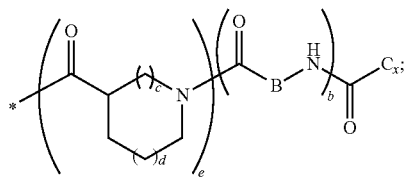

Formula IX

* indicate the attachment sites of the different groups bound by amide functions;

a is an integer equal to 0 or to 1 and a'=1 if a=0 and a'=1, 2 or 3 if a=1;

a' is an integer equal to 1, to 2 or to 3;

b is an integer equal to 0 or to 1;

c is an integer equal to 0 or to 1, and if c is equal to 0, then d is equal to 1 or to 2;

d is an integer equal to 0, to 1 or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6;

l is an integer equal to 0 or to 1 and l'=1 if l=0 and l'=2 if l=1;

r is an integer equal to 0, 1 or to 2;

s' is an integer equal to 0 or to 1;

And if e is different from 0, then at least one of g, h or l is different from 0;

And if a=0, then l=0;

A, $A_1$, $A_2$ and $A_3$ identical or different, are linear or branched alkyl radicals comprising 1 to 8 carbon atoms and, optionally, substituted by a radical from a saturated, unsaturated or aromatic ring;

B is a radical ether or polyether, unsubstituted, comprising from 4 to 14 carbon atoms and from 1 to 5 oxygen atoms, or a linear or branched alkyl radical, optionally comprising an aromatic ring, comprising from 1 to 9 carbon atoms;

$C_x$ is a linear or branched, monovalent alkyl radical optionally comprising a cyclic part, in which x indicates the number of carbon atoms, and:

When the hydrophobic radical -Hy bears 1 -GpC, then $9 \leq x \leq 25$,

When the hydrophobic radical -Hy bears 2 -GpC, then $9 \leq x \leq 15$,

When the hydrophobic radical -Hy bears 3 -GpC, then $7 \leq x \leq 13$,

When the hydrophobic radical -Hy bears 4 -GpC, then $7 \leq x \leq 11$,

When the hydrophobic radical -Hy bears at least 5 -GpC; $6 \leq x \leq 11$;

G is a branched alkyl radical of 1 to 8 carbon atoms, said alkyl radical bears one or more free carboxylic acid functions.

R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and from 1 to 5 oxygen atoms.

the hydrophobic radical(s)—Hy according to formula X being bound to the PLG:

via a covalent bond between a carbonyl of the hydrophobic radical -Hy and a nitrogen atom borne by the PLG, thus forming an amide function resulting from the reaction of an amine function borne by the PLG and an acid function borne by the precursor Hy' of the hydrophobic radical -Hy, and via a covalent bond between a nitrogen atom of the hydrophobic radical -Hy and a carbonyl borne by the PLG; thus forming an amide function resulting from the reaction of an amine function of the precursor -Hy' of the hydrophobic radical -Hy and an acid function borne by the PLG.

The ratio M between the number of hydrophobic radicals and the number of glutamic or aspartic unites being comprised from $0 < M \leq 0.5$;

when several hydrophobic radicals are borne by a co-polyamino acid, then they are identical or different, The degree of polymerization DP in glutamic or aspartic units for the PLG chains is comprised from 5 to 250;

Free carboxylic acids being in the form of an alkaline cation salt chosen from the group consisting of $Na^+$ and $K^+$.

The invention also relates to the precursor Hy' of the hydrophobic radical -Hy according to formula X'.

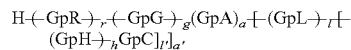

Formula X' in which

GpR is chosen among the radicals according to formulas VII, VII' or VII":

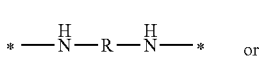

Formula VII

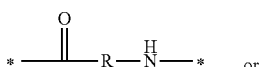

Formula VII'

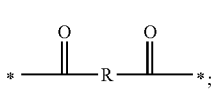

Formula VII"

Identical or different GpG and GpH are chosen among the radicals according to formulas XI or XI';

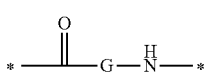

Formula XI

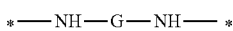

Formula XI'

-GpA is chosen among the radicals according to formula VIII

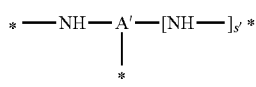

Formula VIII

In which A' is chosen among the radicals according to formulas VIII', VIII" or VIII'''

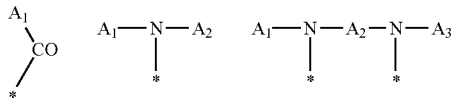

Formula VIII' or Formula VIII" or Formula VIII'"

-GpL is chosen among the radicals according to formula XII

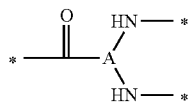

Formula XII

GpC is a radical according to formula IX:

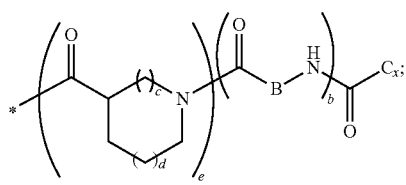

Formula IX

* indicate the attachment sites of the different groups linked by amide functions;
a is an integer equal to 0 or to 1 and a'=1 if a=0 and a'=1, 2 or 3 if a=1;
a' is an integer equal to 1, to 2 or to 3;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6;
l is an integer equal to 0 or to 1 and l'=1 if l=0 and l'=2 if l=1;
r is an integer equal to 0, 1 or to 2;
s' is an integer equal to 0 or to 1;
And if e is different from 0, then at least one of g, h or k is different from 0;
And if a=0, then l=0;
A, $A_1$, $A_2$ and $A_3$ identical or different, are linear or branched alkyl radicals comprising from 1 to 8 carbon atoms and, optionally, substituted by a radical from a saturated, unsaturated or aromatic ring;
B is a radical ether or polyether, unsubstituted, comprising from 4 to 14 carbon atoms and from 1 to 5 oxygen atoms, or a linear or branched alkyl radical, optionally comprising an aromatic ring, comprising from 1 to 9 carbon atoms;
$C_x$ is a linear or branched, monovalent alkyl radical optionally comprising a cyclic part, in which x indicates the number of carbon atoms, and:
When the hydrophobic radical -Hy bears 1 -GpC, then $9 \leq x \leq 25$,
When the hydrophobic radical -Hy bears 2 -GpC, then $9 \leq x \leq 15$,
When the hydrophobic radical -Hy bears 3 -GpC, then $7 \leq x \leq 13$,
When the hydrophobic radical -Hy bears 4 -GpC, then $7 \leq x \leq 11$,
When the hydrophobic radical -Hy bears at least 5 -GpC; $6 \leq x \leq 11$;
G is a branched alkyl radical of 1 to 8 carbon atoms, said alkyl radical bears one or more free carboxylic acid functions.
R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and from 1 to 5 oxygen atoms.
the hydrophobic radical(s)—Hy according to formula X being bound to the PLG:
via a covalent bond between a carbonyl of the hydrophobic radical -Hy and a nitrogen atom borne by the PLG, thus forming an amide function resulting from the reaction of an amine function borne by the PLG and an acid function borne by the precursor Hy' of the hydrophobic radical -Hy, and
via a covalent bond between a nitrogen atom of the hydrophobic radical -Hy and a carbonyl borne by the PLG; thus forming an amide function resulting from the reaction of an amine function of the precursor Hy' of the hydrophobic radical -Hy and an acid function borne by the PLG.
The ratio M between the number of hydrophobic radicals and the number of glutamic or aspartic unites being between $0 < M \leq 0.5$;
when several hydrophobic radicals are borne by a co-polyamino acid, then they are identical or different,
The degree of polymerization DP in glutamic or aspartic units for the PLG chains is comprised from 5 to 250;
Free carboxylic acids being in the form of an alkaline cation salt chosen from the group consisting of $Na^+$ and $K^+$.

In one embodiment, the composition according to the invention is characterized in that the co-polyamino acid is the result of a polyamino acid obtained by polymerization.

In one embodiment, the composition according to the invention is characterized in that the co-polyamino acid is the result of a polyamino acid obtained by polymerization by opening of a ring of a glutamic acid N-carboxyanhydride derivative or of an aspartic acid N-carboxyanhydride derivative.

In one embodiment, the composition according to the invention is characterized in that the co-polyamino acid is the result of a polyamino acid of a glutamic acid N-carboxyanhydride derivative or of an aspartic acid N-carboxyanhydride derivative, as described in Adv. Polym. Sci. 2006, 202, 1-18 (Deming, T. J.).

In one embodiment, the composition according to the invention is characterized in that the co-polyamino acid is the result of a polyamino acid obtained by polymerization f a glutamic acid N-carboxyanhydride derivative.

In one embodiment, the composition according to the invention is characterized in that the co-polyamino acid is the result of a polyamino acid of a glutamic acid N-carboxyanhydride derivative chosen from the group consisting of methyl glutamate N-carboxyanhydride (GluOMe-NCA), benzyl glutamate N-carboxyanhydride (GluOBzl-NCA) and t-butyl N-carboxyanhydride glutamate (GluOtBu-NCA).

In one embodiment, the glutamic acid N-carboxyanhydride derivative is methyl glutamate N-carboxyanhydride (L-GluOMe-NCA).

In one embodiment, the glutamic acid N-carboxyanhydride derivative is benzyl glutamate N-carboxyanhydride (L-GluOMe-NCA).

In one embodiment, the composition according to the invention is characterized in that the co-polyamino acid is the result of a polyamino acid obtained by polymerization of a glutamic acid N-carboxyanhydride derivative or of an aspartic acid N-carboxyanhydride derivative, using an organometallic complex of a transition metal as initiator as described in Nature 1997, 390, 386-389 (Deming, T. J.).

In one embodiment, the composition according to the invention is characterized in that the co-polyamino acid is the result of a polyamino acid obtained by polymerization of a glutamic acid N-carboxyanhydride derivative or of an aspartic acid N-carboxyanhydride derivative, by using the ammonia or a primary amine as initiator as described in patent FR 2.801.226 (Touraud, F.; et al.) and the references cited by this patent.

In one embodiment, the composition according to the invention is characterized in that the co-polyamino acid is the result of a polyamino acid obtained by polymerization of a glutamic acid N-carboxyanhydride derivative or of an aspartic acid N-carboxyanhydride derivative, using hexamethyldisilazane as initiator, as described in publication J. Am. Chem. Soc. 2007, 129, 14114-14115 (Lu H.; et al.) or a sylil amine as described in the publication J. Am. Chem. Soc. 2008, 130, 12562-12563 (Lu H.; et al.).

In one embodiment, the composition according to the invention is characterized in that process for the synthesis of the co-polyamino acid obtained by polymerization of glutamic acid N-carboxyanhydride derivative or of an aspartic acid N-carboxyanhydride derivative, from which results the co-polyamino acid, comprises an ester functions hydrolysis step.

In one embodiment, this ester functions hydrolysis step may consist of a hydrolysis in an acidic medium or a hydrolysis in a basic medium or be carried out by hydrogenation.

In one embodiment, this ester groups hydrolysis step is a hydrolysis in an acidic medium.

In one embodiment, this ester groups hydrolysis step is carried out by hydrogenation.

In one embodiment, the composition according to the invention is characterized in that the co-polyamino acid is the result of a polyamino acid obtained by polymerization of a polyamino acid of a higher molecular weight.

In one embodiment, the composition according to the invention is characterized in that the co-polyamino acid is the result of a polyamino acid obtained by enzymatic polymerization of a polyamino acid of a higher molecular weight.

In one embodiment, the composition according to the invention is characterized in that the co-polyamino acid is the result of a polyamino acid obtained by depolymerization of a polyamino acid of a higher molecular weight.

In one embodiment, the composition according to the invention is characterized in that the co-polyamino acid is the result of a polyamino acid obtained by depolymerization of a polyamino acid of a higher molecular weight.

In one embodiment, the composition according to the invention is characterized in that the co-polyamino acid is obtained by depolymerization of a polyamino acid of a higher molecular weight, chosen from the group consisting of sodium polyglutamate and sodium polyaspartate.

In one embodiment, the composition according to the invention is characterized in that the co-polyamino acid is the result of a polyamino acid obtained by polymerization of a sodium polyglutamate of a higher molecular weight.

In one embodiment, the composition according to the invention is characterized in that the co-polyamino acid is the result of a polyamino acid obtained by polymerization of a sodium polyaspartate. of the highest molecular weight.

In one embodiment, the composition according to the invention is characterized in that the co-polyamino acid is obtained by grafting a hydrophobic group onto a poly-L-glutamic acid or a poly-L-aspartic acid using the amide bond formation process well-known to the person versed in the art.

In one embodiment, the composition according to the invention is characterized in that the co-polyamino acid is obtained by grafting a hydrophobic group onto a poly-L-glutamic acid or a poly-L-aspartic acid using the amide bond formation process used for peptide synthesis.

In one embodiment, the composition according to the invention is characterized in that the co-polyamino acid is obtained by grafting a hydrophobic group onto a poly-L-glutamic acid or a poly-L-aspartic acid as described in patent FR 2,840,614 (Chan, Y. P.; et al.).

In one embodiment, the concentration of co-polyamino acid bearing carboxylate charges and hydrophobic radicals is at most of 40 mg/mL.

In one embodiment, the concentration of co-polyamino acid bearing carboxylate charges and hydrophobic radicals is at most of 30 mg/mL.

In one embodiment, the concentration of co-polyamino acid bearing carboxylate charges and hydrophobic radicals is at most of 20 mg/mL.

In one embodiment, the concentration of co-polyamino acid bearing carboxylate charges and hydrophobic radicals is at most of 10 mg/mL.

In one embodiment, the concentration of co-polyamino acid bearing carboxylate charges and hydrophobic radicals is at most of 5 mg/mL.

In one embodiment, the concentration of co-polyamino acid bearing carboxylate charges and hydrophobic radicals is at most of 2.5 mg/mL.

In one embodiment, the concentration of co-polyamino acid bearing carboxylate charges and hydrophobic radicals is at most of 1 mg/mL.

In one embodiment, the concentration of co-polyamino acid bearing carboxylate charges and hydrophobic radicals is at most of 0.5 mg/mL.

Human glucagon is a highly preserved polypeptide comprising a simple chain of 29 amino acid residues with the following sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH.

It can be obtained in different ways, by peptide synthesis or by recombination.

Human glucagon is available from numerous sources. For example, it may be a human glucagon produced by Bachem via peptide synthesis, specifically under reference 407473.

Human glucagon is used in posologies that vary as a function of applications.

In the emergency treatment of hypoglycemias, the recommended posology is 1 mg by intravenous or intramuscular route (0.5 mg if the body mass is less than 25 kg). This is administered with a solution of human glucagon at a concentration of 1 mg/ml.

In pumps, the daily dose that is considered is about 0.5 mg, the solutions thus can comprise from 0.25 mg/ml to 5 mg/ml of human glucagon.

According to one embodiment, the solutions can comprise from 0.5 mg/ml to 3 mg/ml of human glucagon.

In the treatment of obesity, the daily dose that is considered is about 0.5 mg, the solutions thus can comprise from 0.25 mg/ml to 5 mg/ml of human glucagon.

In one embodiment, the concentration of human glucagon is comprised from 0.25 to 5 mg/mL.

In one embodiment, the concentration of human glucagon is comprised from 0.5 to 4 mg/mL.

In one embodiment, the concentration of human glucagon is comprised from 0.75 to 3 mg/mL.

In one embodiment, the concentration of human glucagon is comprised from 0.75 to 2.5 mg/mL.

In one embodiment, the concentration of human glucagon is comprised from 0.75 to 2 mg/mL.

In one embodiment, the concentration of human glucagon is comprised from 1 to 2 mg/mL.

In one embodiment, the [hydrophobic radical]/[human glucagon] molar ratio is less than 20.

In one embodiment, the [hydrophobic radical]]/[human glucagon] molar ratio is less than 15.

In one embodiment, the [hydrophobic radical]/[human glucagon] molar ratio is less than 10.

In one embodiment, the [hydrophobic radical]/[human glucagon] molar ratio is less than 5.

In one embodiment, the [hydrophobic radical]/[human glucagon] molar ratio is less than 2.5.

In one embodiment, the [hydrophobic radical]/[human glucagon] molar ratio is less than 1.5.

In one embodiment, the [co-polyamino acid bearing carboxylate charges and Hy hydrophobic radicals]/[human glucagon] molar ratio is less than 20.

In one embodiment, the [co-polyamino acid bearing carboxylate charges and Hy hydrophobic radicals]/[human glucagon] molar ratio is less than 15.

In one embodiment, the [co-polyamino acid bearing carboxylate charges and Hy hydrophobic radicals]/[human glucagon] molar ratio is less than 10.

In one embodiment, the [co-polyamino acid bearing carboxylate charges and Hy hydrophobic radicals]/[human glucagon] molar ratio is less than 5.

In one embodiment, the [co-polyamino acid bearing carboxylate charges and Hy hydrophobic radicals]/[human glucagon] molar ratio is less than 2.5.

In one embodiment, the [co-polyamino acid bearing carboxylate charges and Hy hydrophobic radicals]/[human glucagon] molar ratio is less than 1.5.

In one embodiment, the co-polyamino acid bearing carboxylate charges and Hy hydrophobic radicals to glucagon] mass ratio is comprised from 1.5 to 25.

In one embodiment, the co-polyamino acid bearing carboxylate charges and Hy hydrophobic radicals to glucagon] mass ratio is comprised from 2 to 20.

In one embodiment, the co-polyamino acid bearing carboxylate charges and Hy hydrophobic radicals to glucagon] mass ratio is comprised from 2.5 to 15.

In one embodiment, the co-polyamino acid bearing carboxylate charges and Hy hydrophobic radicals to glucagon] mass ratio is comprised from 2 to 10.

In one embodiment, the co-polyamino acid bearing carboxylate charges and Hy hydrophobic radicals to glucagon] mass ratio is comprised from 2 to 7.

In one embodiment, the composition also comprises a nicotinic compound or one of its derivatives.

In one embodiment, the composition comprises nicotinamide.

In one embodiment, the concentration of nicotinamide is comprised from 10 to 160 mM.

In one embodiment, the concentration of nicotinamide is comprised from 20 to 150 mM.

In one embodiment, the concentration of nicotinamide is comprised from 40 to 120 mM.

In one embodiment, the concentration of nicotinamide is comprised from 60 to 100 mM.

The invention also relates to compositions which also comprise ionic species, said ionic species making it possible to improve the stability of the compositions.

The invention also relates to the use of ionic species chosen from the group of anions, cations and/or zwitterions to improve the physical-chemical stability of the compositions.

In one embodiment, the ionic species comprise more than 10 carbon atoms.

Said ionic species are chosen from the group of anions, cations and/or zwitterions. By zwitterion is meant a species bearing at least one positive charge and at least one negative charge on two non-adjacent atoms.

Said ionic species are used alone or in mixture and preferably in mixture.

In one embodiment, the anions are chosen among organic anions.

In one embodiment, the organic anions comprise less than 10 carbon atoms.

In one embodiment, the organic anions are chosen from the group consisting of acetate, citrate and succinate.

In one embodiment, the anions are chosen among anions of mineral origin.

In one embodiment, the anions of mineral origin are chosen from the group consisting of sulfates, phosphates and halides, specifically the chlorides.

In one embodiment, the cations are chosen among organic cations.

In one embodiment, the organic cations comprise less than 10 carbon atoms.

In one embodiment, the organic cations are chosen from the group consisting of ammoniums, for example, 2-Amino-2-(hydroxymethyl)propane-1,3-diol, where the amine is in the form of ammonium.

In one embodiment, the cations are chosen among cations of mineral origin.

In one embodiment, the cations of mineral origin are chosen from the group consisting of zinc, in particular $Zn^{2+}$ and the alkaline metals, in particular $Na^+$ et $K^+$.

In one embodiment, the zwitterions are chosen among zwitterions of organic origin.

In one embodiment, the zwitterions are chosen among the amino acids.

In one embodiment, the amino acids are chosen among the aliphatic amino acids in the group consisting of glycine, alanine, valine, isoleucine and leucine.

In one embodiment, the amino acids are chosen among the cyclic amino acids in the group consisting of proline.

In one embodiment, the amino acids are chosen among the hydroxylated or sulfur-containing amino acids in the group consisting of cysteine, serine, threonine and methionine.

In one embodiment, the amino acids are chosen among the aromatic amino acids in the group consisting of phenylalaline, tyrosine and tryptophane.

In one embodiment, the amino acids are chosen among the amino acids for which the carboxyl function of the side chain is amidified in the group consisting of asparagine and glutamine.

In one embodiment, the zwitterions of organic origin are chosen from the group consisting of amino acids with an uncharged lateral chain.

In one embodiment, the zwitterions of organic origin are chosen from the group consisting of the amino acids or acid amino acids.

In one embodiment, the amino acids are chosen from the group consisting of glutamic acid and aspartic acid, optionally in the form of salts.

In one embodiment, the zwitterions of organic origin are chosen from the group consisting of basic amino acids, or so-called cationic amino acids.

In one embodiment, the so-called "cationic" amino acids are chosen among arginine, histidine and lysine, in particular arginine and lysine.

Most particularly, the zwitterions comprise as many negative charges as positive charges and therefore, a nil overall charge at the iso-electric point and/or at a pH from 6 to 8.

Said ionic species are introduced into the compositions in the form of salts. The introduction of these may be done in solid form before putting them into solution in the compositions, or in the form of a solution, in particular, of a concentrated solution.

For example, cations of mineral origin are added in the form of salts chosen among sodium chloride, zinc chloride, sodium phosphate, sodium sulfate, etc.

For example, anions of organic origin are added in the form of salts chosen among sodium citrate or sodium potassium or sodium acetate.

For example, amino acids are added in the form of salts chosen among arginine hydrochloride, histidine hydrochloride or in non-salified form such as, for example, histidine or arginine.

In one embodiment, the total molar concentration of ionic species in the composition is greater than or equal to 10 mM.

In one embodiment, the total molar concentration of ionic species in the composition is greater than or equal to 20 mM.

In one embodiment, the total molar concentration of ionic species in the composition is greater than or equal to 30 mM.

In one embodiment, the total molar concentration of ionic species in the composition is greater than or equal to 50 mM.

In one embodiment, the total molar concentration of ionic species in the composition is greater than or equal to 75 mM.

In one embodiment, the total molar concentration of ionic species in the composition is greater than or equal to 100 mM.

In one embodiment, the total molar concentration of ionic species in the composition is greater than or equal to 200 mM.

In one embodiment, the total molar concentration of ionic species in the composition is greater than or equal to 300 mM.

In one embodiment, the total molar concentration of ionic species in the composition is greater than or equal to 500 mM.

In one embodiment, the total molar concentration of ionic species in the composition is greater than or equal to 600 mM.

In one embodiment, the total molar concentration of ionic species in the composition is greater than or equal to 700 mM.

In one embodiment, the total molar concentration of ionic species in the composition is greater than or equal to 800 mM.

In one embodiment, the total molar concentration of ionic species in the composition is greater than or equal to 900 mM.

In one embodiment, the total molar concentration of ionic species in the composition is less than or equal to 1000 mM.

In one embodiment, the total molar concentration of ionic species in the composition is less than or equal to 1500 mM.

In one embodiment, the total molar concentration of ionic species in the composition is less than or equal to 1200 mM.

In one embodiment, the total molar concentration of ionic species in the composition is less than or equal to 1000 mM.

In one embodiment, the total molar concentration of ionic species in the composition is less than or equal to 900 mM.

In one embodiment, the total molar concentration of ionic species in the composition is less than or equal to 800 mM.

In one embodiment, the total molar concentration of ionic species in the composition is less than or equal to 700 mM.

In one embodiment, the total molar concentration of ionic species in the composition is less than or equal to 600 mM.

In one embodiment, the total molar concentration of ionic species in the composition is less than or equal to 500 mM.

In one embodiment, the total molar concentration of ionic species in the composition is less than or equal to 400 mM.

In one embodiment, the total molar concentration of ionic species in the composition is less than or equal to 300 mM.

In one embodiment, the total molar concentration of ionic species in the composition is less than or equal to 200 mM.

In one embodiment, the total molar concentration of ionic species in the composition is less than or equal to 100 mM.

In one embodiment, the total molar concentration of ionic species in the composition is comprised from 10 to 1000 mM.

In one embodiment, the total molar concentration of ionic species in the composition is comprised from 20 to 1000 mM.

In one embodiment, the total molar concentration of ionic species in the composition is comprised from 30 to 1000 mM.

In one embodiment, the total molar concentration of ionic species in the composition is comprised from 50 to 1000 mM.

In one embodiment, the total molar concentration of ionic species in the composition is comprised from 75 to 1000 mM.

In one embodiment, the total molar concentration of ionic species in the composition is comprised from 100 to 1000 mM.

In one embodiment, the total molar concentration of ionic species in the composition is comprised from 200 to 1000 mM.

In one embodiment, the total molar concentration of ionic species in the composition is comprised from 300 to 1000 mM.

In one embodiment, the total molar concentration of ionic species in the composition is comprised from 400 to 1000 mM.

In one embodiment, the total molar concentration of ionic species in the composition is comprised from 500 to 1000 mM.

In one embodiment, the total molar concentration of ionic species in the composition is comprised from 600 to 1000 mM.

In one embodiment, the total molar concentration of ionic species in the composition is comprised from 10 to 900 mM.

In one embodiment, the total molar concentration of ionic species in the composition is comprised from 20 to 900 mM.

In one embodiment, the total molar concentration of ionic species in the composition is comprised from 30 to 900 mM.

In one embodiment, the total molar concentration of ionic species in the composition is comprised from 50 to 900 mM.

In one embodiment, the total molar concentration of ionic species in the composition is comprised from 75 to 900 mM.

In one embodiment, the total molar concentration of ionic species in the composition is comprised from 100 to 900 mM.

In one embodiment, the total molar concentration of ionic species in the composition is comprised from 200 to 900 mM.

In one embodiment, the total molar concentration of ionic species in the composition is comprised from 300 to 900 mM.

In one embodiment, the total molar concentration of ionic species in the composition is comprised from 400 to 900 mM.

In one embodiment, the total molar concentration of ionic species in the composition is comprised from 500 to 900 mM.

In one embodiment, the total molar concentration of ionic species in the composition is comprised from 600 to 900 mM.

In one embodiment, the total molar concentration of ionic species in the composition is comprised from 10 to 800 mM.

In one embodiment, the total molar concentration of ionic species in the composition is comprised from 20 to 800 mM.

In one embodiment, the total molar concentration of ionic species in the composition is comprised from 30 to 800 mM.

In one embodiment, the total molar concentration of ionic species in the composition is comprised from 50 to 800 mM.

In one embodiment, the total molar concentration of ionic species in the composition is comprised from 75 to 800 mM.

In one embodiment, the total molar concentration of ionic species in the composition is comprised from 100 to 800 mM.

In one embodiment, the total molar concentration of ionic species in the composition is comprised from 200 to 800 mM.

In one embodiment, the total molar concentration of ionic species in the composition is comprised from 300 to 800 mM.

In one embodiment, the total molar concentration of ionic species in the composition is comprised from 400 to 800 mM.

In one embodiment, the total molar concentration of ionic species in the composition is comprised from 500 to 800 mM.

In one embodiment, the total molar concentration of ionic species in the composition is comprised from 600 to 800 mM.

In one embodiment, the total molar concentration of ionic species in the composition is comprised from 10 to 700 mM.

In one embodiment, the total molar concentration of ionic species in the composition is comprised from 20 to 700 mM.

In one embodiment, the total molar concentration of ionic species in the composition is comprised from 30 to 700 mM.

In one embodiment, the total molar concentration of ionic species in the composition is comprised from 50 to 700 mM.

In one embodiment, the total molar concentration of ionic species in the composition is comprised from 75 to 700 mM.

In one embodiment, the total molar concentration of ionic species in the composition is comprised from 100 to 700 mM.

In one embodiment, the total molar concentration of ionic species in the composition is comprised from 200 to 700 mM.

In one embodiment, the total molar concentration of ionic species in the composition is comprised from 300 to 700 mM.

In one embodiment, the total molar concentration of ionic species in the composition is comprised from 400 to 700 mM.

In one embodiment, the total molar concentration of ionic species in the composition is comprised from 500 to 700 mM.

In one embodiment, the total molar concentration of ionic species in the composition is comprised from 600 to 700 mM.

In one embodiment, the total molar concentration of ionic species in the composition is comprised from 10 to 600 mM.

In one embodiment, the total molar concentration of ionic species in the composition is comprised from 20 to 600 mM.

In one embodiment, the total molar concentration of ionic species in the composition is comprised from 30 to 600 mM.

In one embodiment, the total molar concentration of ionic species in the composition is comprised from 50 to 600 mM.

In one embodiment, the total molar concentration of ionic species in the composition is comprised from 75 to 600 mM.

In one embodiment, the total molar concentration of ionic species in the composition is comprised from 100 to 600 mM.

In one embodiment, the total molar concentration of ionic species in the composition is comprised from 200 to 600 mM.

In one embodiment, the total molar concentration of ionic species in the composition is comprised from 300 to 600 mM.

In one embodiment, the total molar concentration of ionic species in the composition is comprised from 400 to 600 mM.

In one embodiment, the total molar concentration of ionic species in the composition is comprised from 500 to 600 mM.

In one embodiment, the total molar concentration of ionic species in the composition is comprised from 10 to 500 mM.

In one embodiment, the total molar concentration of ionic species in the composition is comprised from 20 to 500 mM.

In one embodiment, the total molar concentration of ionic species in the composition is comprised from 30 to 500 mM.

In one embodiment, the total molar concentration of ionic species in the composition is comprised from 50 to 500 mM.

In one embodiment, the total molar concentration of ionic species in the composition is comprised from 75 to 500 mM.

In one embodiment, the total molar concentration of ionic species in the composition is comprised from 100 to 500 mM.

In one embodiment, the total molar concentration of ionic species in the composition is comprised from 200 to 500 mM.

In one embodiment, the total molar concentration of ionic species in the composition is comprised from 300 to 500 mM.

In one embodiment, the total molar concentration of ionic species in the composition is comprised from 400 to 500 mM.

In one embodiment, the total molar concentration of ionic species in the composition is comprised from 10 to 400 mM.

In one embodiment, the total molar concentration of ionic species in the composition is comprised from 20 to 400 mM.

In one embodiment, the total molar concentration of ionic species in the composition is comprised from 30 to 400 mM.

In one embodiment, the total molar concentration of ionic species in the composition is comprised from 50 to 400 mM.

In one embodiment, the total molar concentration of ionic species in the composition is comprised from 75 to 400 mM.

In one embodiment, the total molar concentration of ionic species in the composition is comprised from 100 to 400 mM.

In one embodiment, the total molar concentration of ionic species in the composition is comprised from 200 to 400 mM.

In one embodiment, the total molar concentration of ionic species in the composition is comprised from 300 to 400 mM.

In one embodiment, the total molar concentration of ionic species in the composition is comprised from 10 to 300 mM.

In one embodiment, the total molar concentration of ionic species in the composition is comprised from 20 to 300 mM.

In one embodiment, the total molar concentration of ionic species in the composition is comprised from 30 to 300 mM.

In one embodiment, the total molar concentration of ionic species in the composition is comprised from 50 to 300 mM.

In one embodiment, the total molar concentration of ionic species in the composition is comprised from 75 to 300 mM.

In one embodiment, the total molar concentration of ionic species in the composition is comprised from 100 to 300 mM.

In one embodiment, the total molar concentration of ionic species in the composition is comprised from 200 to 300 mM.

In one embodiment, the total molar concentration of ionic species in the composition is comprised from 10 to 200 mM.

In one embodiment, the total molar concentration of ionic species in the composition is comprised from 20 to 200 mM.

In one embodiment, the total molar concentration of ionic species in the composition is comprised from 30 to 200 mM.

In one embodiment, the total molar concentration of ionic species in the composition is comprised from 50 to 200 mM.

In one embodiment, the total molar concentration of ionic species in the composition is comprised from 75 to 200 mM.

In one embodiment, the total molar concentration of ionic species in the composition is comprised from 100 to 200 mM.

In one embodiment, the total molar concentration of ionic species in the composition is comprised from 10 to 100 mM.

In one embodiment, the total molar concentration of ionic species in the composition is comprised from 20 to 100 mM.

In one embodiment, the total molar concentration of ionic species in the composition is comprised from 30 to 100 mM.

In one embodiment, the total molar concentration of ionic species in the composition is comprised from 50 to 100 mM.

In one embodiment, the total molar concentration of ionic species in the composition is comprised from 75 to 100 mM.

In one embodiment, the total molar concentration of ionic species in the composition is comprised from 10 to 75 mM.

In one embodiment, the total molar concentration of ionic species in the composition is comprised from 20 to 75 mM.

In one embodiment, the total molar concentration of ionic species in the composition is comprised from 30 to 75 mM.

In one embodiment, the total molar concentration of ionic species in the composition is comprised from 50 to 75 mM.

In one embodiment, the total molar concentration of ionic species in the composition is comprised from 10 to 50 mM.

In one embodiment, the total molar concentration of ionic species in the composition is comprised from 20 to 50 mM.

In one embodiment, the total molar concentration of ionic species in the composition is comprised from 30 to 50 mM.

In one embodiment, said ionic species are present in a concentration from 5 to 400 mM.

In one embodiment, said ionic species are present in a concentration from 5 to 300 mM.

In one embodiment, said ionic species are present in a concentration from 5 to 200 mM.

In one embodiment, said ionic species are present in a concentration from 5 to 100 mM.

In one embodiment, said ionic species are present in a concentration from 5 to 75 mM.

In one embodiment, said ionic species are present in a concentration from 5 to 50 mM.

In one embodiment, said ionic species are present in a concentration from 5 to 25 mM.

In one embodiment, said ionic species are present in a concentration from 5 to 20 mM.

In one embodiment, said ionic species are present in a concentration from 5 to 10 mM.

In one embodiment, said ionic species are present in a concentration from 10 to 400 mM.

In one embodiment, said ionic species are present in a concentration from 10 to 300 mM.

In one embodiment, said ionic species are present in a concentration from 10 to 200 mM.

In one embodiment, said ionic species are present in a concentration from 10 to 100 mM.

In one embodiment, said ionic species are present in a concentration from 10 to 75 mM.

In one embodiment, said ionic species are present in a concentration from 10 to 50 mM.

In one embodiment, said ionic species are present in a concentration from 10 to 25 mM.

In one embodiment, said ionic species are present in a concentration from 10 to 20 mM.

In one embodiment, said ionic species are present in a concentration from 20 to 300 mM.

In one embodiment, said ionic species are present in a concentration from 20 to 200 mM.

In one embodiment, said ionic species are present in a concentration from 20 to 100 mM.

In one embodiment, said ionic species are present in a concentration from 20 to 75 mM.

In one embodiment, said ionic species are present in a concentration from 20 to 50 mM.

In one embodiment, said ionic species are present in a concentration from 20 to 25 mM.

In one embodiment, said ionic species are present in a concentration from 50 to 300 mM.

In one embodiment, said ionic species are present in a concentration from 50 to 200 mM.

In one embodiment, said ionic species are present in a concentration from 50 to 100 mM.

In one embodiment, said ionic species are present in a concentration from 50 to 75 mM.

Regarding cations of mineral origin and, in particular, $Zn^{2+}$, its molar concentration in the composition may be from 0.25 to 20 mM, in particular, from 0.25 to 10 mM or from 0.25 to 5 mM.

In one embodiment, the ionic species present is NaCl.

In one embodiment, the concentration of NaCl is comprised from 5 to 250 mM.

In one embodiment, the concentration of NaCl is comprised from 10 to 150 mM. In one embodiment, the concentration of NaCl is comprised from 20 to 100 mM.

In one embodiment, the ionic species present is citric acid and/or its salts.

In one embodiment, the concentration of citric acid is comprised from 5 to 40 mM.

In one embodiment, the concentration of citric acid is comprised from 7 to 30 mM.

In one embodiment, the concentration of citric acid is comprised from 8 to 20 mM.

In one embodiment, the concentration of citric acid is comprised from 105 [sic] to 15 mM.

In one embodiment, the composition also comprises a polyanionic compound.

In one embodiment, the polyanionic compound is chosen from the group consisting of the carboxylate polyacids and their salts $Na^+$, $K^+$, $Ca^{2+}$ or $Mg^{2+}$.

In one embodiment, the polyanionic compound is chosen from the group consisting of citric acid, tartric acid, and their salts $Na^+$, $K^+$, $Ca^{2+}$ or $Mg^{2+}$.

In one embodiment, the polyanionic compound is chosen from the group consisting of the phosphoric polyacids and their salts $Na^+$, $K^+$, $Ca^{2+}$ or $Mg^{2+}$.

In one embodiment, the phosphoric polyacid compound is triphosphate and its salts $Na^+$, $K^+$, $Ca^{2+}$ or $Mg^{2+}$.

In one embodiment, the polyanionic compound is citric acid and its salts $Na^+$, $K^+$, $Ca^{2+}$ or $Mg^{2+}$.

In one embodiment, the polyanionic compound is chosen tartric acid and its salts $Na^+$, $K^+$, $Ca^{2+}$ or $Mg^{2+}$.

In one embodiment, the polyanionic compound is triphosphate acid and its salts $Na^+$, $K^+$, $Ca^{2+}$ or $Mg^{2+}$.

In one embodiment, the concentration of polyanionic compound is comprised from 1 to 20 mM.

In one embodiment, the concentration of polyanionic compound is comprised from 2 to 15 mM.

In one embodiment, the concentration of polyanionic compound is comprised from 3 to 12 mM.

In one embodiment, the concentration of polyanionic compound is 10 mM.

In one embodiment, the concentration of polyanionic compound is 5 mM.

In one embodiment, the concentration of polyanionic compound is 10 mM for concentrations of glucagon from 0.5 mg/ml and 3 mg/ml.

In one embodiment, the concentration of polyanionic compound is 10 mM for concentrations of glucagon from 0.5 mg/ml and 2 mg/ml.

In one embodiment, the concentration of polyanionic compound is 10 mM for concentrations of glucagon from 1 mg/ml and 2 mg/ml.

In one embodiment, the concentration of polyanionic compound is 5 mM for concentrations of glucagon from 0.5 mg/ml and 3 mg/ml.

In one embodiment, the concentration of polyanionic compound is 5 mM for concentrations of glucagon from 0.5 mg/ml and 2 mg/ml.

In one embodiment, the concentration of polyanionic compound is 5 mM for concentrations of glucagon from 1 mg/ml and 2 mg/ml.

In one embodiment, the concentration in citric acid and its salts $Na^+$, $K^+$, $Ca^{2+}$ or $Mg^{2+}$ is comprised from 1 to 20 mM.

In one embodiment, the concentration in citric acid and its salts $Na^+$, $K^+$, $Ca^{2+}$ or $Mg^{2+}$ is comprised from 2 to 15 mM.

In one embodiment, the concentration in citric acid and its salts $Na^+$, $K^+$, $Ca^{2+}$ or $Mg^{2+}$ is comprised from 3 to 12 mM.

In one embodiment, the concentration of citric acid and its salts $Na^+$, $K^+$, $Ca^{2+}$ or $Mg^{2+}$ is 10 mM.

In one embodiment, the concentration of citric acid and its salts $Na^+$, $K^+$, $Ca^{2+}$ or $Mg^{2+}$ is 5 mM.

In one embodiment, the concentration in citric acid and its salts $Na^+$, $K^+$, $Ca^{2+}$ or $Mg^{2+}$ is 10 mM for concentrations in glucagon from 0.5 mg/ml to 3 mg/ml.

In one embodiment, the concentration in citric acid and its salts $Na^+$, $K^+$, $Ca^{2+}$ or $Mg^{2+}$ is 10 mM for concentrations in glucagon from 0.5 mg/ml to 2 mg/ml.

In one embodiment, the concentration in citric acid and its salts $Na^+$, $K^+$, $Ca^{2+}$ or $Mg^{2+}$ is 10 mM for concentrations in glucagon from 1 mg/ml to 2 mg/ml.

In one embodiment, the concentration in citric acid and its salts $Na^+$, $K^+$, $Ca^{2+}$ or $Mg^{2+}$ is 5 mM for concentrations in glucagon from 0.5 mg/ml to 3 mg/ml.

In one embodiment, the concentration in citric acid and its salts $Na^+$, $K^+$, $Ca^{2+}$ or $Mg^{2+}$ is 5 mM for concentrations in glucagon from 0.5 mg/ml to 2 mg/ml.

In one embodiment, the concentration in citric acid and its salts $Na^+$, $K^+$, $Ca^{2+}$ or $Mg^{2+}$ is 5 mM for concentrations in glucagon from 1 mg/ml to 2 mg/ml.

In one embodiment, the pharmaceutical composition also comprises at least one absorption promoter chosen among absorption promoters, diffusion promoters or vasodilating agents, alone or in mixture.

Absorption promoters include, but are not limited to, the surfactants, for example, bile salts, fatty acid salts or phospholipids; nicotinic agents such as nicotinamides, nicotinic acids, niacin, niacinamide, vitamin B3 and their salts; pancreatic trypsin inhibiters; magnesium salts; polyunsaturated fatty acids; didecanyl phophatidylcholine; the aminopolycarboxylates; tolmetine, sodium caprate; salicylic acid; oleic acid; linoleic acid; eicosapntaenoic acid (EPA); docosahexaenoic acid (DHA); benzylic acid; nitrogen monoxide donors, for example, 3-(2-Hydroxy-1-(1-methylethyl)-2-nitrosohydrazino)-1-propanamine, 1a N-ethyl-2-(1-ethyl-hydroxy-2-1-nitrosohydrazino)-ethanamine, or S-nitroso-N-acetylpenicillamine; bile acids, 1a glycine conjugated to a bile acid; sodium ascorbate, potassium ascorbate; sodium salicylate, potassium salicylate, actyl-salicylic acid, salicylosalicylic acid, aluminum acetylsalicylate aluminum, choline salicylate, salicylamide, lysine acetylsalicylate; exalamide; diflunisal; ethenzamide; EDTA; alone or in mixture.

In one embodiment, the pharmaceutical composition also comprises at least one diffusion promoter. Examples of diffusion promoters include, but are not limited to, the glycosaminoglycanases, for example hyaluronidase.

In one embodiment, the pharmaceutical composition also comprises at least one vasodilator.

In one embodiment, the pharmaceutical composition also comprises at least one vasodilating agent causing hyperpolarization by blocking ionic calcium channels.

In one embodiment, the vasodilating agent that causes hyperpolarization by blocking ionic calcium channels is adenosine, a hyperpolarizing agent derived from the endothelium, a type 5 phosphodiesterase inhibitor (PDE5), an agent for opening potassium channels, or any combination of these agents.

In one embodiment, the pharmaceutical composition also comprises at least one vasodilating agent, mediated by AMPc.

In one embodiment, the pharmaceutical composition also comprises at least one vasodilating agent, mediated by GMPc.

In one embodiment, the pharmaceutical composition also comprises at least one vasodilating agent, chosen from the group comprising the vasodilating agents which act by causing hyperpolerization by blocking ionic calcium channels, vasodilators mediated by AMPc, and vasodilators, mediated by GMPc.

At least one vasodilating agent is chosen from the group comprising nitrogen monoxide donors, for example, nitroglycerin, isosorbide dinitrate, isosorbide mononitrate, amyl nitrate, erythrityl, tetranitrate, nitroprussiate); prostacycline and its analogues, for example sodium epoprostenol, iloprost, epoprostenol, treprostinil or selexipag; histamine, 2-methylhistamine, 4-methylhistamine; 2-(2-pyridyl)ethylamine, 2-(2-thiazolyl)ethylamine; papaverin, papaverin hydrochloride; minoxidil; dipyridamol; hydralazine; adenosine, adnosine triphosphate; uridine trisphosphate; GPLC; L-carnitine; arginine; prostaglandin D2; potassium salts; and in certain cases, α1 and α2 receptors antagonists, for example, prazosine, phenoxybenzamine, phentolamine, dibenamine, moxissylite hydrochloride and tolazoline), betazol, dimaprit; β2 receptors agonists, for example, isoproterenol, dobutamin, albuterol, terbutalin, aminophyllin, theophyllin, caffeine; alprostadil, ambrisentan; cabergolin diazoxide; dihydralazine mesilate; diltiazem hydrochloride; enoximone; flunarizine hydrochloride; *Ginkgo biloba* extract; levosimendan; molsidomine; naftidrofuryl acid oxalate; nicorandil; pentoxifylline; phenoxybenzamine chloride; basic piribedil; piribedil mesilate; regadenoson monohydrate; riociguat; sildenafil citrate, tadalafil, vardenafil tryhydrated hydrochloride; trimethazidine hydrochloride; trinitrine; verapamil; endothline receptors antagonists, for example, avanafil and bosentran monohydrate; and the calcium channel inhibiters, for example, amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, prandipine; alone or in mixture.

According to one embodiment, the vasodilating agent is treprostinil.

In one embodiment, the composition also comprises a polyanionic compound and an absorption promoter.

In one embodiment, the composition comprises, in combination, citric acid and/or its salts $Na^+$, $K^+$, $Ca^{2+}$ or $Mg^{2+}$ and an absorption promoter.

In one embodiment, the polyanionic compound is citric acid and its salts $Na^+$, $K^+$, $Ca^{2+}$ or $Mg^{2+}$.

In one embodiment, the composition comprises, in combination, a polyanionic compound, and an absorption promoter and, optionally, NaCl.

In one embodiment, the composition comprises, in combination, citric acid and/or its salts $Na^+$, $K^+$, $Ca^{2+}$ or $Mg^{2+}$, nicotinamide or treprostinil, and optionally, NaCl.

In one embodiment, the composition comprises, in combination, citric acid and/or its salts $Na^+$, $K^+$, $Ca^{2+}$ or $Mg^{2+}$ nicotinamide or treprostinil, and optionally, NaCl, and is intended for intramuscular administration.

In one embodiment, the composition comprises, in combination, citric acid and/or its salts $Na^+$, $K^+$, $Ca^{2+}$ or $Mg^{2+}$ nicotinamide, optionally, NaCl, and is intended for intramuscular administration.

In one embodiment, the composition comprises, in combination, citric acid and/or its salts $Na^+$, $K^+$, $Ca^{2+}$ or $Mg^{2+}$, treprostinil, and optionally, NaCl, and is intended for intramuscular administration.

In one embodiment, the composition comprises, in combination, citric acid and/or its salts $Na^+$, $K^+$, $Ca^{2+}$ or $Mg^{2+}$ nicotinamide or treprostinil, and optionally, NaCl, and is intended for sub-cutaneous administration.

In one embodiment, the composition comprises, in combination, citric acid and/or its salts $Na^+$, $K^+$, $Ca^{2+}$ or $Mg^{2+}$ nicotinamide, optionally, NaCl, and is intended for sub-cutaneous administration.

In one embodiment, the composition comprises, in combination, citric acid and/or its salts $Na^+$, $K^+$, $Ca^{2+}$ or $Mg^{2+}$, treprostinil, and optionally, NaCl, and is intended for sub-cutaneous administration.

In one embodiment, the compositions according to the invention also comprise a gastro-intestinal hormone.

By "gastro-intestinal hormones" is meant hormones chosen from the group consisting of the GLP-1 RAs for Glucagon human-Like Peptide receptor agonists (Glucagon like peptide-1 receptor agonist)Glucagon like) and GIP (Glucose-dependent insulinotropic peptide), oxyntomodulin (a human proglucagon derivative), YY peptide, amylin, cholecystokinin, pancreatic polypeptide (PP), ghrelin and enterostatin, their analogues or derivatives and/or pharmaceutically acceptable salts.

In one embodiment, the gastro-intestinal hormones are analogues or derivatives of GLP-1 RA (Glucagon like peptide-1 receptor agonist) chosen from the group consisting of exenatide or Byetta® (ASTRA-ZENECA), liraglutide or Victoza® (NOVO NORDISK), lixisenatide or Lyxumia® (SANOFI), albiglutide or Tanzeum® (GSK) or dulaglutide or Trulicity® (ELI LILLY & CO), their analogues or derivatives and their pharmaceutically acceptable salts.

In one embodiment, the gastro-intestinal hormone is pramlintide Symlin® (ASTRA-ZENECA).

In one embodiment, the gastro-intestinal hormone is exenatide or Byetta®, its analogues or derivatives and their pharmaceutically acceptable salts.

In one embodiment, the gastro-intestinal hormone is liraglutide or Victoza®, its analogues or derivatives and their pharmaceutically acceptable salts.

In one embodiment, the gastro-intestinal hormone is lixisenatide or Lyxumia®, its analogues or derivatives and their pharmaceutically acceptable salts.

In one embodiment, the gastro-intestinal hormone is albiglutide or Tanzeum®, its analogues or derivatives and their pharmaceutically acceptable salts.

In one embodiment, the gastro-intestinal hormone is dulaglutide or Trulicity®, its analogues or derivatives and their pharmaceutically acceptable salts.

In one embodiment, the gastro-intestinal hormone pramlintide or Symlin® its analogues or derivatives and their pharmaceutically acceptable salts.

By "analogue", when it is used to refer to a peptide or a protein, is meant a peptide or a protein in which one or more constitutive amino acid residues have been substituted by other amino acid residues and/or in which one or more constitutive amino acid residues have been deleted and/or in which one or more constitutive amino acid residues have been added. The percentage of homology allowed for this definition of an analogue is 50%.

By "derived", when used in reference to a peptide or a protein, is meant a peptide or a protein or an analogue chemically modified by a substitute which is not present in the cited peptide or protein or reference analogue, that is, a peptide or a protein which was modified by creation of covalent bonds, in order to introduce substitutes.

In one embodiment, the substitute is chosen from the group consisting of fatty chains.

In one embodiment, the concentration of gastro-intestinal hormone is comprised in an interval from 0.01 to 10 mg/mL.

In one embodiment, the concentration of exentide, its analogues or derivatives and their pharmaceutically acceptable salts is comprised within an interval from 0.04 to 0.5 mg/mL.

In one embodiment, the concentration of liraglutide, its analogues or derivatives and their pharmaceutically acceptable salts is comprised within an interval from 1 to 10 mg/mL.

In one embodiment, the concentration of lixisentide, its analogues or derivatives and their pharmaceutically acceptable salts is comprised within an interval from 0.01 to 1 mg/mL.

In one embodiment, the concentration of pramlintide, its analogues or derivatives and their pharmaceutically acceptable salts is comprised within an interval from 0.1 to 5 mg/mL.

In one embodiment, the compositions according to the invention are made by mixing solutions of human glucagon obtained by the preparation of lyophilisate and solutions GLP-1 RA (Glucagon like peptide-1 receptor agonist) GLP-1 RA, of GLP-1 RA analogue or derivative, said solutions of GLP-1 RA being commercial or prepared using lyphilosate.

In one embodiment, the compositions according to the invention also comprise buffers.

In one embodiment, the compositions according to the invention comprise buffers in a concentration from 0 to 100 mM.

In one embodiment, the compositions according to the invention comprise buffers in a concentration from 15 to 50 mM.

In one embodiment, the compositions according to the invention comprise a buffer chosen from the group consisting of a phosphate buffer, Tris (trishydroxymethylaminomethane), and sodium citrate.

In one embodiment, the buffer is sodium phosphate.

In one embodiment, the buffer is Tris (trishydroxymethylaminomethane).

In one embodiment, the buffer is sodium citrate.

In one embodiment, the composition also comprises a zinc salt, in particular zinc chloride.

In one embodiment, the concentration in zinc salt is comprised from 50 to 5000 µM.

In one embodiment, the concentration in zinc salt is comprised from 100 to 2000 µM.

In one embodiment, the concentration in zinc salt is comprised from 200 to 1500 µM.

In one embodiment, the concentration in zinc salt is comprised from 200 to 1000 µM.

In one embodiment, the concentration in zinc is such that the [zinc]/[glucagon] molar ratio is comprised from 0.1 to 2.5.

In one embodiment, the concentration in zinc is such that the [zinc]/[glucagon] molar ratio is comprised from 0.2 to 2.

In one embodiment, the concentration in zinc is such that the [zinc]/[glucagon] molar ratio is comprised from 0.5 to 1.5.

In one embodiment, the concentration in zinc is such that the [zinc]/[glucagon] molar ratio is 1.

In one embodiment, the compositions according to the invention also comprise preservatives.

In one embodiment, the preservatives are chosen from the group consisting of m-cresol and phenol, alone or in mixture.

In one embodiment, the compositions according to the invention also comprise antioxidants.

In one embodiment, the antioxidants are chosen among methionine.

In one embodiment, the concentration of preservatives is comprised from 10 to 50 mM.

In one embodiment, the concentration of preservatives is comprised from 10 to 40 mM.

In one embodiment, the compositions according to the invention also comprise a tensioactive.

In one embodiment, the tensioactive is chosen from the group consisting of glycol propylene and polysorbate.

The compositions according to the invention also comprise additives such as tonicity agents.

In one embodiment, the tonicity agents are chosen from the group consisting of sodium chloride, mannitol, sucrose, sorbitol and glycerol.

Compositions according to the invention may also comprise all of the excipients in compliance with the pharmacopoeias and compatible with the human insulin and gastro-intestinal hormones, specifically the GLP-1 RAs, used at usage concentrations.

The invention also relates to a pharmaceutical formulation according to the invention characterized in that it is obtained by drying and/or lyophilization.

In the case of local and systemic releases, the routes of administration considered are intravenous, sub-cutaneous, intradermal or intramuscular.

Transdermal, oral, nasal, vaginal, ocular, mouth and pulmonary routes of administration are also considered.

The invention also relates to single-dose formulations at a pH from 6.6 to 7.8, comprising human glucagon.

The invention also relates to single-dose formulations at a pH from 6.6 to 7.8 comprising human glucagon and a gastro-intestinal hormone, as defined above.

In one embodiment the single-dose formulations also comprise a co-polyamino acid substituted as defined above.

In one embodiment, the formulations are in the form of an injectable solution. In one embodiment, the GLP-1 RA, analogue or derivative of GLP-1 RA, is chosen from the group comprising exenatide (Byetta®), liraglutide (Victoza®), lixisenatide (Lyxumia®), albiglutide (Tanzeum®), dulaglutide (Trulicity®) or one of their derivatives.

In one embodiment, the gastro-intestinal hormone is exenatide.

In one embodiment, the gastro-intestinal hormone is liraglutide.

In one embodiment, the gastro-intestinal hormone is lixisenatide.

In one embodiment, the gastro-intestinal hormone is albiglutide.

In one embodiment, the gastro-intestinal hormone is dulaglutide.

Furthermore, and just as importantly, the applicant was able to verify that the human glucagon present in a co-polyamino acid bearing carboxylate charges and at least one hydrophobic radical according to the invention preserves its action whether it is alone or in combination with a gastro-intestinal hormone.

The preparation of a composition according to the invention has the advantage of being able to be prepared by simple mixing of a solution of human glucagon, a solution of GLP-1 RA, an analogue or derivative of GLP-1 RA and a co-polyamino acid bearing carboxylate charges and at least one hydrophobic radical according to the invention, in aqueous solution or in lyophilized form. If necessary, the pH of the preparation is adjusted to pH 7.

In one embodiment, the mixture of human glucagon and substituted co-polyamino acid is concentrated by ultrafiltration before mixing with GLP-1 RA, an analogue or derivative of GLP-1 RA in aqueous solution or in lyophilized form.

If necessary, the composition of the mixture is adjusted with excipients such as glyceril, m-cresol, and polysorbate (Tween®) by adding concentrated solutions of these excipients to the mixture. If necessary, the pH of the preparation is adjusted to pH 7.

The following examples are used to illustrate the invention without, however, being limitative.

Part A—Synthesis of Intermediate Hy Hydrophobic Compounds Making it Possible to Obtain -Hy Radicals.

| No. | INTERMEDIATE HYDROPHOBIC COMPOUNDS |
|---|---|
| A1 | |
| A2 | |
| A3 | |
| A4 | |

-continued
| No. | INTERMEDIATE HYDROPHOBIC COMPOUNDS |
|---|---|
| A5 | 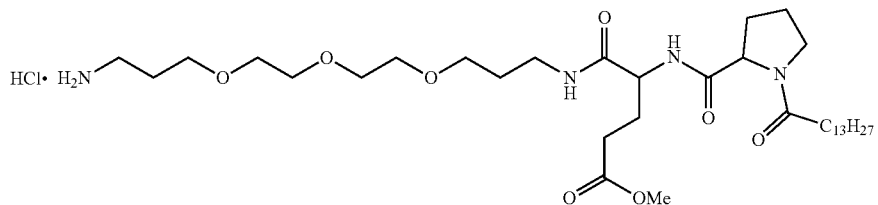 |
| A7 | 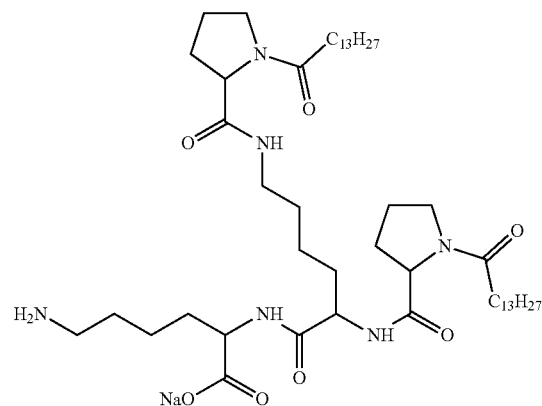 |
| A5a | 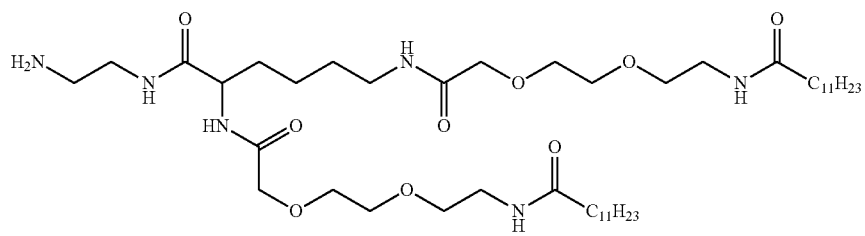 |
| A6a | 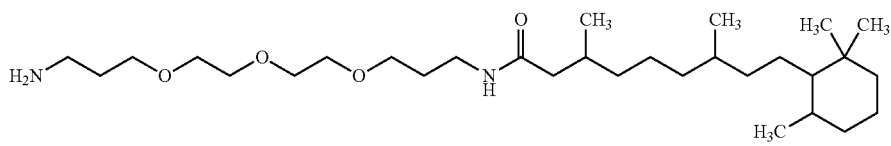 [SMILES: CC(CCCC(C)CC(=O)NCCCOCCOCCOCCCN)CCC1C(C)CCCC1(C)C] |
| A8 | 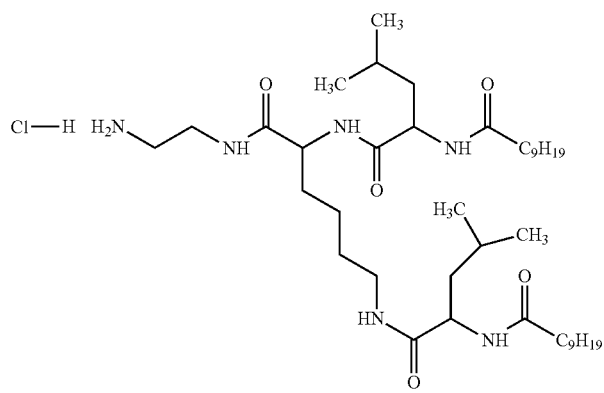 |
| A9 | 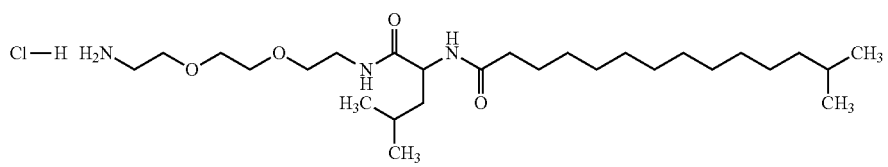 |

-continued
| No. | INTERMEDIATE HYDROPHOBIC COMPOUNDS |
|---|---|
| A10 | 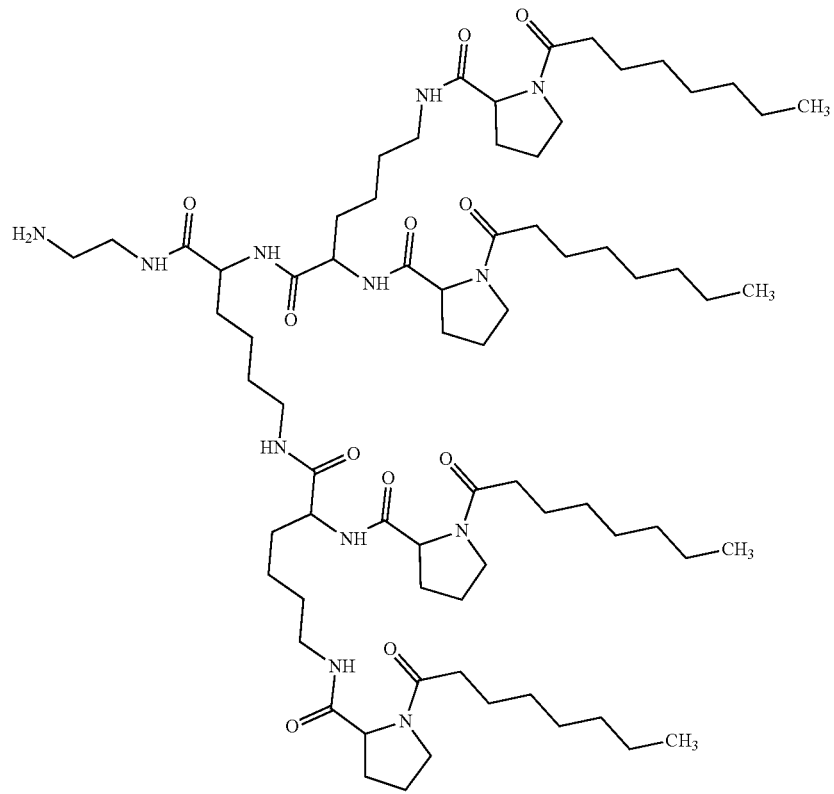 [SMILES: CCCCCCCC(=O)N1CCCC1C(=O)NCCCCC(NC(=O)C1CCCN1C(=O)CCCCCCC)C(=O)NCCCCC(NC(=O)C(CCCCNC(=O)C1CCCN1C(=O)CCCCCCC)NC(=O)C1CCCN1C(=O)CCCCCCC)C(=O)NCCN] |
| A11 | 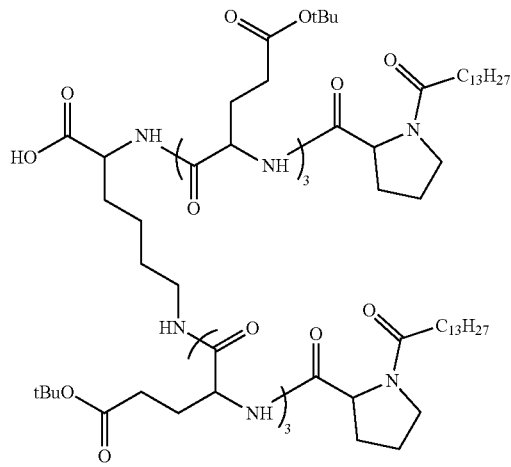 |

| No. | INTERMEDIATE HYDROPHOBIC COMPOUNDS |
|---|---|
| A12 | 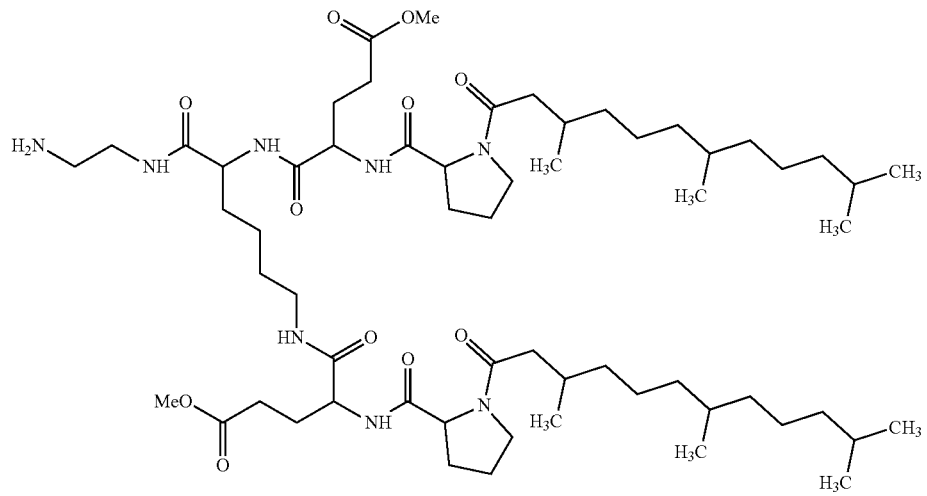 [SMILES: COC(=O)CCC(NC(=O)C1CCCN1C(=O)CC(C)CCCC(C)CCCC(C)C)C(=O)NCCCCC(NC(=O)C(CCC(=O)OC)NC(=O)C1CCCN1C(=O)CC(C)CCCC(C)CCCC(C)C)C(=O)NCCN] |
| A13 | 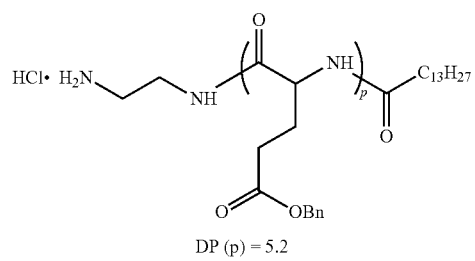<br>DP (p) = 5.2 |
| A15 | 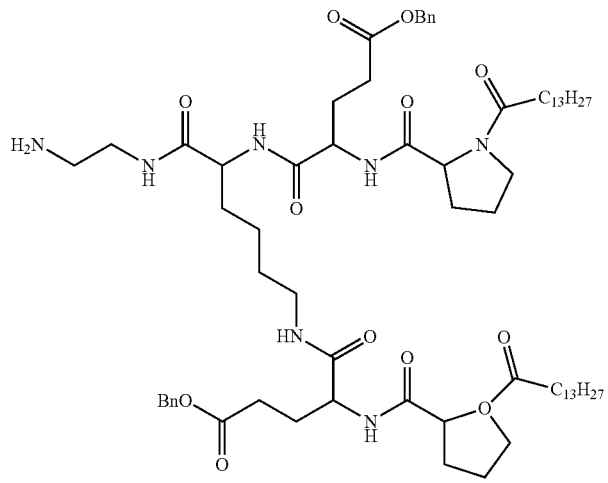 |

| No. | INTERMEDIATE HYDROPHOBIC COMPOUNDS |
|---|---|
| A16 | 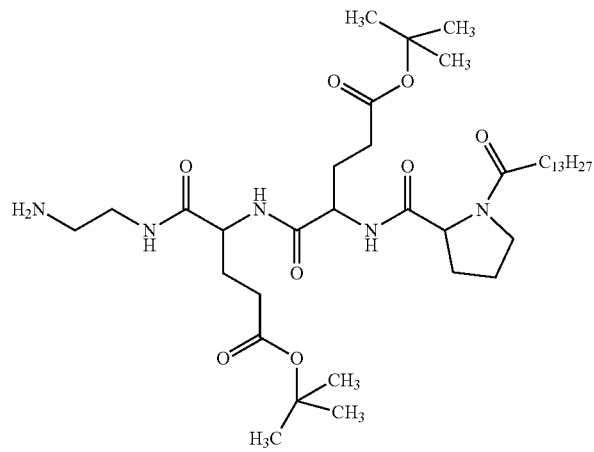 |
| A17 | 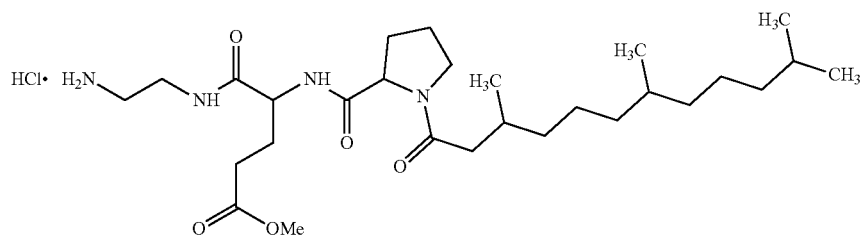 [SMILES: COC(=O)CCC(NC(=O)C1CCCN1C(=O)CC(C)CCCC(C)CCCC(C)C)C(=O)NCCN] |
| A18 | 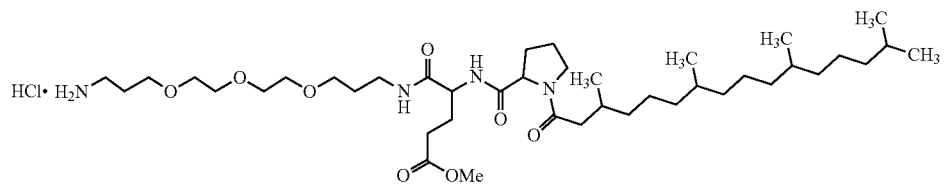 [SMILES: COC(=O)CCC(NC(=O)C1CCCN1C(=O)CC(C)CCCC(C)CCCC(C)CCCC(C)C)C(=O)NCCCOCCOCCOCCCN] |
| A19 | 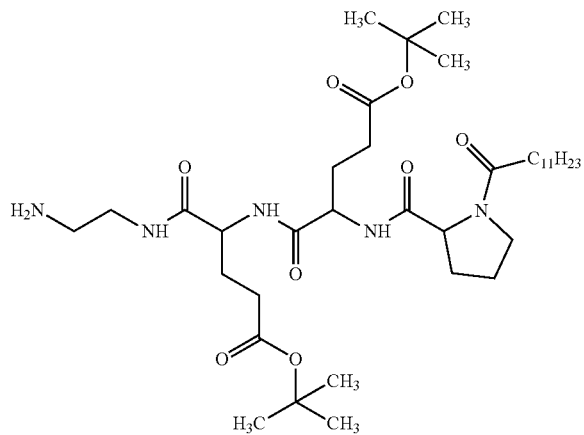 |

| No. | INTERMEDIATE HYDROPHOBIC COMPOUNDS |
|---|---|
| A20 | 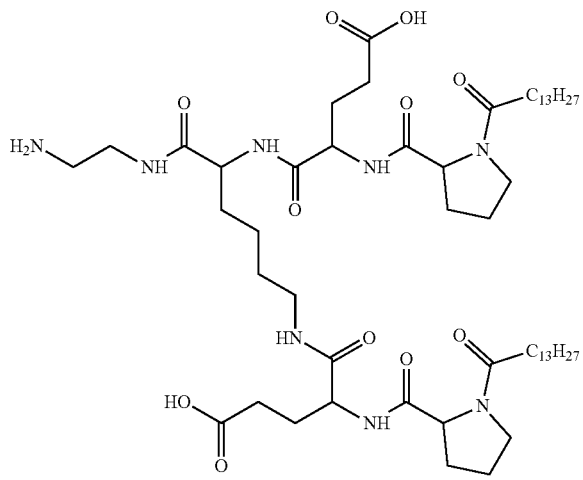 |

Example A1: Molecule A1

Molecule 1: Product Obtained by the Reaction Between Fmoc-Lys(Fmoc)-OH and the Resin 2-Cl-Trityl Chloride.

To a suspension of Fmoc-Lys(Fmoc)-OH (7.32 g, 12.40 mmol) in dichloromethane (60 mL) at room temperature is added DIPEA (4.32 mL, 24.80 mmol). After complete solubilization (10 min), the solution obtained is poured onto the resin 2-Cl-trityl chloride previously washed in dichloromethane (100-200 mesh, 1% DVB, 1.24 mmol/g) (4.00 g, 4.96 mmol), After stirring for 2 hours at room temperature, HPLC grade methanol (0.8 mL/g resin, 3.2 mL) is added and the medium is stirred at room temperature for 15 minutes. The resin is filtered, successively washed with dichloromethane (3×60 mL), DMF (2×60 mL), dichloromethane (2×60 mL), isopropanol (1×60 mL) and dichloromethane (3×60 mL).

Molecule 2: Product Obtained by the Reaction Between Molecule 1 and an 80:20 DMF/Piperidine Mixture.

Molecule 1, previously washed with DMF, is treated with an 80:20 DMF/piperidine mixture (60 mL). After 30 minutes of stirring at room temperature, the resin is filtered, successively washed with DMF (3×60 mL), isopropanol (1×60 mL) and dichloromethane (3×60 mL).

Molecule 3: Product Obtained by the Reaction Between Molecule 2 and a Fmoc-Glu(OtBu)-OH.

To a suspension of Fmoc-Glu(OtBu)-OH (10.55 g, 24.80 mmol) and of 1-[bis(dimethylamino)methylene]-1H-1,2,3-triazolo[4,5-b]pyridinium 3-oxide hexafluorophosphate (HATU, 9.43 g, 24.80 mmol) in a 1:1 mixture of DMF/dichloromethane (60 mL) is added DIPEA (8.64 mL, 49.60 mmol). After complete solubilization, the solution obtained is poured onto molecule 2. After 2 hours of stirring at room temperature, the resin is filtered, successively washed with DMF (3×60 mL), isopropanol (1×60 mL) and dichloromethane (3×60 mL).

Molecule 4: Product Obtained by the Reaction Between Molecule 3 and a 50:50 DMF/Morpholine Mixture.

Molecule 3, previously washed with DMF, is treated with a 50:50 DMF/piperidine mixture (60 mL). After 1 hour 15 minutes of stirring at room temperature, the resin is filtered, successively washed with DMF (3×60 mL), isopropanol (1×60 mL) and dichloromethane (3×60 mL).

Molecule 5: Product Obtained by the Reaction Between Molecule 4 and Molecule 11.

Molecule 5 is obtained using a process similar to that used for molecule 3, applied to molecule 4 and to molecule 11 (8.07 g, 24.80 mmol) in DMF (60 mL).

Molecule 6: Product Obtained by the Reaction Between Molecule 5 and an 80:20 dichloromethane/1,1,1,3,3,3-hexafluoro-2-propanol (HFIP) mixture.

Molecule 5 is treated with an 80:20 dichloromethane/1,1,1,3,3,3-hexafluoro-2-propanol (HFIP) (60 mL) mixture. After 20 minutes of stirring at room temperature, the resin is filtered and washed with dichloromethane (2×60 mL). The solvents are evaporated under reduced pressure. Two co-evaporations are then carried out on the residue with dichloromethane (60 mL) then with diisopropylether (60 mL). The product is purified by chromatography on silica gel (dichloromethane, methanol). A white solid of molecule 6 is obtained.

Yield: 2.92 g (52% in 6 steps)

RMN $^1$H (CD$_3$OD, ppm): 0.90 (6H); 1.22-2.47 (88H); 3.13-3.25 (2H); 3.45-3.76 (4H); 4.24-4.55 (5H).

LC/MS (ESI+): 1131.9 (calculated ([M+H]$^+$): 1131.8).

Molecule 7: Product Obtained by the Reaction Between Molecule 6 and N-Boc Ethylenediamine To a solution of molecule 6 (2.82 g, 2.49 mmol) in Me-THF (20 mL) at room temperature are successively added N-hydroxybenzotriazole (HOBt, 496 mg, 3.24 mmol) and N-Boc ethylenediamine (BocEDA, 440 mg, 2.74 mmol). The mixture is cooled to 0° C. then (3-dimethylaminopropyl)-N'-ethylcarbodiimide (EDC, 621 mg, 3.24 mmol) hydrochloride is added. The medium is stirred for 15 minutes at 0° C. then for 18 h at room temperature. The organic phase is diluted with dichloromethane (30 mL) and washed with an aqueous solution saturated in NH$_4$Cl (2×20 mL), an aqueous solution saturated in NaHCO$_3$ (2×20 mL), and a saturated NaCl aqueous solution (2×20 mL). The organic phase is dried over Na$_2$SO$_4$, filtered and concentrated under reduced pressure. A white solid of molecule 7 is obtained after recrystallization in acetonitrile Yield: 2.47 g (78%)

RMN $^1$H (CDCl$_3$, ppm): 0.87 (6H); 1.09-1.77 (77H); 1.84-2.49 (20H); 2.99-3.83 (10H); 4.16-4.25 (1H); 4.27-

4.47 (4H); 5.68 (0.1H); 5.95-6.08 (0.9H); 6.91-7.14 (2H); 7.43-7.57 (1H); 7.68-7.78 (1H); 8.22-8.35 (1H).

LC/MS (ESI+): 1273.9 (calculated ([M+H]$^+$): 1273.9).

Molecule A1

To a solution of molecule 7 (2.47 g, 1.94 mmol) in dichloromethane (20 mL) at room temperature is added a solution of HCl 4 N in dioxane (7.27 mL) then the medium is stirred for 16 hours at room temperature. After concentration under reduced pressure, co-evaporation and washing with diisopropylether, a white solid of molecule A1 in the form of an HCl salt is obtained. This solid is solubilized in water (100 mL) then the pH is adjusted to 7 by adding an aqueous solution of NaOH 1 N. The solution is lyophilized and the lyophilisate is dried by co-evaporation in the toluene. A white solid of molecule A1 is obtained.

Yield: 1.64 g (80%)

RMN $^1$H (D$_2$O, ppm): 0.90 (6H); 1.15-2.59 (70H); 3.06-3.86 (10H); 4.19-4.43 (5H).

LC/MS (ESI+): 1061.8 (calculated ([M+H]$^+$): 1061.8).

Example A2: Molecule A2

Molecule 8: Product Obtained by the Coupling Between Myristic Acid and Methyl-L-Glutamate.

To a solution of myrisitic acid (35.0 g, 153.26 mmol) in tetrahydrofurane THF (315 mL) at 0° C. are successively added N-hydroxysuccinimide (NHS, 17.81 g, 154.79 mmol) and N,N-dicyclohexylcarboxydiimide (DCC, 31.94 g, 154.79 mmol). The medium is stirred for 48 hours while raising the temperature to room temperature, filtered on the sinter filter, then added to a solution of methyl-L-glutamate (24.95 g, 154.9 mmol) and N,N-diisopropylethylamine (DIPEA, 99.0 g, 766.28 mmol) in water (30 mL). The reaction medium is stirred at 20° C. for 48 hours then concentrated under reduced pressure. Water (200 mL) is added and the mixture obtained is treated by the successive addition of ethyl acetate (AcOEt, 100 mL) then an aqueous solution of Na$_2$CO$_3$ at 5% (50 mL). The aqueous phase is then washed again with AcOEt (100 mL), acidified by adding an aqueous solution of 10% HCl and the product is extracted with dichloromethane (DCM, 3×150 mL). The organic phase is dried over Na$_2$SO$_4$, filtered and concentrated under reduced pressure. A white solid of molecule 8 is obtained.

Yield: 47.11 g (84%)

RMN $^1$H (CDCl$_3$, ppm) 0.87 (3H); 1.07-1.66 (22H); 2.02-2.11 (1H); 2.18-2.36 (3H); 2.39-2.47 (1H); 2.50-2.58 (1H); 3.69 (3H); 4.54-4.59 (1H); 6.62 (1H); 8.26 (1H).

LC/MS (ESI+): 372.2 (calculated ([M+H]$^+$): 372.3).

Molecule 9: Product Obtained by the Coupling Between Molecule 8 and Methyl-L-Glutamate.

Using a process similar to that used for the preparation of molecule 8 and applied to molecule 8 (35.0 g, 94.21 mmol) and to methyl-L-glutamate (15.33 g, 95.15 mmol), a white solid of molecule 9 is obtained after recrystallization in acetonitrile Yield: 24.0 g (49%)

RMN $^1$H (DMSO-d6, ppm): 0.85 (3H); 1.06-1.51 (22H); 1.70-1.94 (3H); 1.96-2.15 (3H); 2.29-2.40 (4H); 3.58 (3H); 3.58 (3H); 4.16-4.22 (1H); 4.25-4.32 (1H); 7.93 (1H); 8.16 (1H); 12.66 (1H).

LC/MS (ESI+): 515.3 (calculated ([M+H]$^+$): 515.3).

Molecule 10: Product Obtained by the Reaction Between Molecule 9 and N-Boc Ethylenediamine.

To a suspension of molecule 9 (24.0 g, 46.63 mmol) in DCM (285 mL) at 0° C. are successively added HOBt (714 mg, 46.66 mmol), BocEDA (8.97 g, 55.96 mmol) in solution in DCM (25 mL) then EDC (9.83 g, 51.30 mmol). The medium is stirred for 1 hour at 0° C. then for 18 h at room temperature. The organic phase is washed with an aqueous solution saturated in NaHCO$_3$ (2×300 mL), an aqueous solution saturated in HCl 1 N (2×300 mL), and a saturated NaCl aqueous solution (500 mL). Methanol (40 mL) is added, the organic phase is dried over Na$_2$SO$_4$, filtered and concentrated under reduced pressure. A white solid of molecule 10 is obtained after recrystallization in acetonitrile Yield: 27.15 g (89%)

RMN $^1$H (CDCl$_3$, ppm): 0.87 (3H); 1.07-1.68 (22H); 1.42 (9H); 1.97-2.18 (4H); 2.22-2.31 (2H); 2.35-2.55 (4H); 3.19-3.29 (2H); 3.30-3.38 (2H); 3.66 (3H); 3.68 (3H); 4.34-4.41 (1H); 4.42-4.48 (1H); 5.54 (1H); 6.99-7.18 (2H) 7.56 (1H).

LC/MS (ESI+): 657.4 (calculated ([M+H]$^+$): 657.4).

Molecule A2

To a solution of molecule 10 (27.15 g, 41.33 mmol) in a DCM/methanol mixture (410 mL) at 0° C. is added a solution of HCl 4 N in dioxane (51.7 mL) then the medium is stirred for 2 hours at 0° C., then 16 hours at room temperature. After concentration under reduced pressure, co-evaporation in methanol (2×150 mL), a white solid of molecule A2 in the form of a hydrochloride salt is obtained after recrystallization in acetonitrile.

Yield: 23.2 g (95%)

RMN $^1$H (DMSO-d6, ppm): 0.85 (3H); 1.05-1.52 (22H); 1.71-1.85 (2H); 1.87-2.03 (2H); 2.07-2.18 (2H); 2.24-2.37 (4H); 2.84 (2H); 3.24-3.38 (2H); 3.58 (3H); 3.58 (3H); 4.17-4.24 (2H); 7.95-8.08 (5H); 8.14 (1H).

LC/MS (ESI+): 557.3 (calculated ([M+H]$^+$): 557.4).

Example A3: Molecule A3

Molecule 11: Product Obtained by the Reaction Between Myristoyl Chloride and L-Proline.

To a solution of L-proline (300.40 g, 2.61 mol) in aqueous soda 2 N (1.63 L) at 0° C. is slowly added over an 1 h myristoyl chloride (322 g, 1.30 mol) in solution in dichloromethane (DCM, 1.63 L). After this addition, the reaction medium is raised to 20° C. over 3 h, then stirred for 2 h. The mixture is cooled to 0° C. then a 37% HCl aqueous solution (215 mL) is added over 15 minutes. The reaction medium is stirred for 1 hour from 0° C. to 20° C. The organic phase is separated, washed with a 10% HCl aqueous solution (3×430 mL), a saturated NaCl aqueous solution (430 mL), dried over Na$_2$SO$_4$, filtered with cotton, then concentrated under reduced pressure. The residue is solubilized in the heptane (1.31 L) at 50° C., then the solution is progressively brought to room temperature. After priming the crystallization using a glass rod, the medium is again heated to 40° C. for 30 minutes, then reduced to room temperature over 4 hours. A white solid is obtained after sinter filtration, washing with heptane (2×350 mL) and drying under reduced pressure.

Yield: 410 g (97%)

RMN $^1$H (CDCl$_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H).

LC/MS (ESI): 326.4; 651.7 (calculated ([M+H]$^+$): 326.3; ([2M+H]$^+$): 651.6).

Molecule 12: Product Obtained by the Coupling Between Molecule 11 and Methyl-L-Glutamate.

Using a process similar to that used for the preparation of molecule 8 and applied to molecule 11 (30.0 g, 92.17 mmol) and to methyl-L-glutamate (15.60 g, 96.78 mmol), a white solid of molecule 12 is obtained after recrystallization in refluxing acetone, cooling to room temperature and sinter filtration. The filtrate is evaporated and the residue is precipitated in acetone, as above, with this operation being repeated 3 times.

Yield: 15.5 g (36%)

RMN $^1$H (DMSO-d6, ppm): 0.85 (3H); 1.07-1.37 (20H); 1.40-1.50 (2H); 1.71-2.27 (8H); 2.30-2.40 (2H); 3.28-3.54 (2H); 3.58 (1.3H); 3.59 (1.7H); 4.14-4.28 (1H); 4.28-4.37 (1H); 8.06 (0.55H); 8.33 (0.45H); 12.64 (1H).

LC/MS (ESI+): 469.2 (calculated ([M+H]$^+$): 469.3).

Molecule 13: Product Obtained by the Reaction Between Molecule 12 and N-Boc Ethylenediamine.

Using a process similar to that used for the preparation of molecule 10 and applied to molecule 12 (15.5 g, 33.05 mmol) and to methyl-L-glutamate (5.83 g, 36.36 mmol), a white solid of molecule 13 is obtained after recrystallization in acetonitrile Yield: 19.8 g (83%)

RMN $^1$H (DMSO-d6, ppm): 0.85 (3H); 1.07-1.55 (22H); 1.37 (9H); 1.69-2.19 (7H); 2.22-2.36 (3H); 2.91-3.17 (4H); 3.28-3.60 (5H); 4.11-4.18 (0.7H); 4.20-4.28 (1H); 4.38-4.42 (0.3H); 6.74 (1H); 7.64 (0.7H); 7.87 (0.7H); 7.98 (0.3H); 8.22 (0.3H).

LC/MS (ESI+): 611.4 (calculated ([M+H]$^+$): 611.4).

Molecule A3

Using a process similar to that used for the preparation of molecule A2 and applied to molecule 13 (16.8 g, 27.50 mmol), a white solid of molecule A3 in the form of a hydrochloride salt is obtained after recrystallization in acetonitrile Yield: 13.5 g (90%)

RMN $^1$H (DMSO-d6, ppm): 0.85 (3H); 1.08-1.52 (22H); 1.70-2.37 (10H); 2.80-2.90 (2H); 3.22-3.62 (4H); 3.57 (3H); 4.15-4.28 (1.75H); 4.41-4.44 (0.25H); 7.81-8.13 (4.5H); 8.24-8.29 (0.25H) 8.33-8.39 (0.25H).

LC/MS (ESI+): 511.3 (calculated ([M+H]$^+$): 511.4).

Example A4: Molecule A4

Molecule 14: Product Obtained by the Reaction Between Lauroyl Chloride and L-Proline Using a process similar to that used for the preparation of molecule 11 and applied to lauroyl chloride (27.42 g, 685.67 mmol) and to L-proline (60.0 g, 247.27 mmol), a white solid of molecule 14 is obtained.

Yield: 78.35 g (96%)

RMN $^1$H (CDCl$_3$, ppm): 0.87 (3H); 1.26 (16H); 1.70 (2H); 1.90-2.10 (3H); 2.35 (2H); 2.49 (1H); 3.48 (1H); 3.56 (1H); 4.60 (1H).

LC/MS (ESI+): 298.1 (calculated ([M+H]$^+$): 298.2).

Molecule 15: Product Obtained by the Coupling Between Molecule 14 and Methyl-L-Glutamate.

Using a process similar to that used for the preparation of molecule 8 and applied to molecule 14 (34.64 g, 116.46 mmol) and to methyl-L-glutamate (19.14 g, 118.79 mmol), a white solid of molecule 15 is obtained after recrystallization in acetonitrile Yield: 37.28 g (73%)

RMN $^1$H (CDCl$_3$, ppm): 0.85 (3H); 1.08-1.42 (16H); 1.54-1.06 (2H); 1.80-2.47 (10H); 3.42-3.80 (2H); 3.65 (2.55H); 3.67 (0.45H); 4.37-4.40 (0.15H); 4.51-4.58 (0.85H); 4.58-4.67 (1H); 7.26 (0.15H) 7.65 (0.85H); 8.06 (1H).

LC/MS (ESI+): 441.1 (calculated ([M+H]$^+$): 441.3).

Molecule 16: Product Obtained by the Reaction Between Molecule 15 and N-Boc Ethylenediamine.

Using a process similar to that used for the preparation of molecule 10 and applied to molecule 15 (37.30 g, 84.66 mmol) and to methyl-L-glutamate (14.92 g, 93.13 mmol), a white solid of molecule 16 is obtained after recrystallization in acetonitrile Yield: 43.10 g (87%)

RMN $^1$H (DMSO-d6, ppm): 0.85 (3H); 1.08-1.53 (18H); 1.37 (9H); 1.70-2.36 (10H); 2.91-3.60 (9H); 4.11-4.18 (0.7H); 4.21-4.28 (1H); 4.38-4.42 (0.3H); 6.38 (0.1H); 6.74 (0.9H); 7.65 (0.7H); 7.87 (0.7H); 7.99 (0.3H); 8.22 (0.3H).

LC/MS (ESI+): 583.4 (calculated ([M+H]$^+$): 583.4).

Molecule A4

Using a process similar to that used for the preparation of molecule A2 and applied to molecule 16 (43.10 g, 73.96 mmol), a white solid of molecule A4 in the form of a hydrochloride salt is obtained after recrystallization in acetonitrile Yield: 31.90 g (83%)

RMN $^1$H (DMSO-d6, ppm): 0.85 (3H); 1.05-1.37 (16H); 1.39-1.52 (2H); 1.70-2.37 (10H); 2.29-2.91 (2H); 3.20-3.62 (7H); 4.16-4.29 (1.7H); 4.42-4.46 (3H); 7.86-8.18 (4.6H); 8.32 (0.3H); 8.40 (0.3H).

LC/MS (ESI+): 483.2 (calculated ([M+H]$^+$): 483.3).

Example A5: Molecule A5

Molecule 17: Product Obtained by the Reaction Between 1-Amino-4,7,10-Trioxa-13-Tridecane Amine and Tert-Butyl Phenylcarbonate.

To a solution of 1-amino-4,7,10-trioxa-13-tridecane amine and (112.29 g, 509.71 mmol) in ethanol (510 mL) at 80° C. is added, drop by drop, tert-butyl phenylcarbonate (49.50 g, 254.86 mmol). The reaction medium is stirred at 80° C. for 3 hours 30 minutes then concentrated under reduced pressure. The residue is solubilized in water (250 mL), the pH is adjusted to 2.3 with a 37% HCl solution, and the mixture is extracted with methyl tert-butylether (MTBE, 2×150 mL). The aqueous phase is basified to pH 12.6 by adding 2 N NaOH solution extracted with DCM (3×250 μm>). The organic phase is washed with an aqueous solution of 1 N NaOH (1×100 mL), a saturated NaCl aqueous solution (100 mL), dried over Na$_2$SO$_4$, filtered and concentrated under reduced pressure. A yellow oil of molecule 17 is obtained.

Yield: 54.4 g (67%)

RMN $^1$H (CDCl$_3$, ppm): 1.40-1.58 (11H); 1.73-1.81 (4H); 2.80-2.84 (2H); 3.20-3.70 (14H); 5.11 (1H).

LC/MS (ESI+): 321.2 (calculated ([M+H]$^+$): 321.2).

Molecule 18: Product Obtained by the Coupling Between Molecule 12 and Molecule 17.

Using a process similar to that used for the preparation of molecule 10 and applied to molecule 12 (20.46 g, 43.66 mmol) and to molecule 17 (16.79 g, 52.39 mmol), a white wax of molecule 18 is obtained after purification by flash chromatography (eluent: DCM, methanol), solubilization of the residue in DCM (300 mL), washes of the organic phase with an aqueous solution of NaHCO$_3$ (2×150 mL), an aqueous solution of 10% HCl (2×150 mL), aa saturated NaCl aqueous solution (2×150 mL), dried over Na$_2$SO$_4$ and concentrated under reduced pressure.

Yield: 30.15 g (90%)

RMN $^1$H (DMSO-d6, ppm): 0.85 (3H); 1.09-1.52 (31H); 1.55-1.67 (4H); 1.69-2.36 (10H); 2.91-2.98 (2H); 3.02-3.17 (2H); 3.28-3.61 (17H); 4.12-4.17 (0.7H); 4.20-4.28 (1H); 4.39-4.42 (0.3H); 6.37 (0.1H); 6.71 (0.9H); 7.59 (0.7H); 7.85 (0.7H); 7.94 (0.3H); 8.21 (0.3H).

LC/MS (ESI+): 771.4 (calculated ([M+H]$^+$): 771.5).

Molecule A5

Using a process similar to that used for the preparation of molecule A2 and applied to molecule 18 (30.0 g, 38.91 mmol), a white solid of molecule A5 in the form of a hydrochloride salt is obtained after solubilization of the residue in water (500 mL) and lyophilization.

Yield: 25.2 g (91%)

RMN $^1$H (DMSO-d6, ppm): 0.85 (3H); 1.06-1.37 (20H); 1.39-1.52 (2H); 1.58-1.66 (2H); 1.70-2.37 (12H); 2.78-2.85 (2H); 3.01-3.15 (2H); 3.31-3.62 (17H); 4.11-4.17 (0.7H); 4.19-4.27 (1H); 4.41-4.44 (0.3H); 7.63-7.71 (0.7H); 7.90-8.24 (4H); 8.28-8.35 (0.3H);

LC/MS (ESI+): 671.4 (calculated ([M+H]$^+$): 671.5).

Example A7: Molecule A7

Molecule 21: Product Obtained by the Coupling Between Molecule 11 and L-Lysine.

Using a process similar to that used for the preparation of molecule 8 and applied to molecule 11 (133.00 g, 408.61 mmol) and to L-lysine (31.36 g, 214.52 mmol), a white solid of molecule 21 is obtained after crystallization 2 times in acetone.

Yield: 106.50 g (68%)

RMN $^1$H (DMSO-d$_6$, ppm): 0.85 (6H); 1.26 (40H); 1.35-1.50 (6H); 1.50-2.10 (10H); 2.10-2.25 (4H); 3.01 (2H); 3.31-3.55 (4H); 4.10-4.40 (3H); 7.68 (0.6H); 7.97 (1H); 8.27 (0.4H); 12.50 (1H).

LC/MS (ESI): 761.8 (calculated ([M+H]$^+$): 762.1).

Molecule 22: Product Obtained by the Coupling Between Molecule 21 and Methyl N-Boc-L-Lysinate.

Using a process similar to that used for the preparation of molecule 10 and applied to molecule 21 (43.00 g, 56.50 mmol) in solution in THF and to N-Boc-L-lysinate methyl hydrochloride (20.12 g, 67.79 mmol), a transparent solid of molecule 22 is obtained and used without any additional purification.

Yield: 55.80 g (98%)

RMN $^1$H (DMSO-d6, ppm): 0.86 (6H); 1.08-2.03 (64H); 1.37 (9H); 2.07-2.30 (4H); 2.84-3.09 (4H); 3.29-3.57 (4H); 3.58-3.65 (3H); 4.14-4.43 (4H); 6.40 (0.1H); 6.74 (0.9H); 7.69 (0.6H); 7.82 (0.6H); 7.95-8.06 (1H); 8.11-8.20 (0.4H); 8.26 (0.4H).

LC/MS (ESI): 1003.8 (calculated ([M+H]$^+$): 1003.8).

Molecule 23: Product Obtained by the Saponification of Molecule 23.

A solution of molecule 22 (55.80 g, 55.61 mmol) in a 1:1 mixture of THF/water (370 mL) at 0° C. is treated by the slow addition of a solution of LiOH (2.00 g, 83.41 mmol) in water (185 mL). After 16 hours of stirring at 0° C., the medium is concentrated under reduced pressure and the residue is redissolved in water (500 mL). DCM (500 mL) is added, the heterogeneous mixture is cooled to 10° C. and acidified by adding an aqueous solution of 10% HCl to pH 1. The aqueous phase is extracted with DCM (2×300 mL), the combined organic phases are washed with aa saturated NaCl aqueous solution (2×300 mL), dried over Na$_2$SO$_4$, filtered and concentrated under reduced pressure. A white solid of molecule 23 is obtained after crystallization in acetone.

Yield: 46.10 g (84%)

RMN $^1$H (pyridine-d6, ppm): 0.85 (6H); 1.05-2.03 (67H); 2.07-2.61 (10H); 3.12-3.93 (8H); 4.54-4.93 (2H); 4.98-5.16 (2H); 7.35-7.45 (1H); 8.34-8.63 (1H); 8.94-9.41 (2H).

LC/MS (ESI): 989.8 (calculated ([M+H]$^+$): 989.8).

Molecule A7

To a solution of molecule 23 (12.00 g, 12.13 mmol) in dichloromethane (40 mL) at 0° C. is added a solution of HCl 4 N in dioxane (15.20 mL) then the medium is stirred for 15 hours 0° C. and 5 hours at room temperature. The reaction mixture is concentrated under reduced pressure, the residue is solubilized in a mixture of DCM (120 mL) and NaOH 2 N (60 mL). After separation of the phases, the organic phase is washed by a solution of 2 N NaOH (60 mL), dried over Na$_2$SO$_4$ and concentrated under reduced pressure.

Yield: 10.90 g (98%)

RMN $^1$H (DMSO-d6, ppm): 0.86 (6H); 1.05-2.27 (70H); 2.45-2.52 (2H); 2.90-3.58 (6H); 3.67-3.76 (1H); 4.02-4.10 (0.6H); 4.11-4.17 (0.4H); 4.20-4.26 (0.6H); 4.30-4.39 (1h); 4.42-4.46 (0.4H); 7.29-7.42 (1H); 7.71-7.80 (0.6H); 7.97-8.05 (0.6H); 8.10-8.24 (0.4H); 8.33-8.45 (0.4H);

LC/MS (ESI): 887.7 (calculated ([M−H]$^-$): 887.7).

Example A5A: Molecule A5A

Molecule 3a: Product Obtained by the Reaction Between Fmoc-Lys(Fmoc)-OH and the Resin 2-Cl-Trityl Chloride.

To a suspension of Fmoc-Lys(Fmoc)-OH (7.32 g, 12.40 mmol) in DCM (60 mL) at room temperature is added DIPEA (4.32 mL, 24.80 mmol). After complete solubilization (10 min), the solution obtained is poured onto the resin 2-Cl-trityl chloride (100-200 mesh, 1% DVB, 1.24 mmol/g) (4.00 g, 4.96 mmol) previously washed in DCM in a reactor used for peptide synthesis on a solid medium. After stirring for 2 hours at room temperature, HPLC grade methanol (0.8 mL/g resin, 3.2 mL) is added and the medium is stirred at room temperature for 15 minutes. The resin is filtered, successively washed with DCM (3×60 mL), DMF (2×60 mL), DCM (2×60 mL), isopropanol (1×60 mL) and DCM (3×60 mL).

Molecule 4a: Product Obtained by the Reaction Between Molecule 3a and an 80:20 DMF/Piperidine Mixture.

Molecule 3a, previously washed with DMF, is treated with an 80:20 DMF/piperidine mixture (60 mL). After 30 minutes of stirring at room temperature, the resin is filtered, successively washed with DMF (3×60 mL), isopropanol (1×60 mL) and DCM (3×60 mL).

Molecule 5a: Product Obtained by Reaction Between Molecule 4a and 8-Acid (9-Fluorenylmethyloxycarbonyl-Amino)-3,6-Dioxaoctanoic (Fmoc-O2Oc-OH).

To a suspension of Fmoc-O2Oc-OH (9.56 g, 24.80 mmol) and of 1-[bis(dimethylamino)methylene]-1H-1,2,3-triazolo[4,5-b]pyridinium 3-oxide hexafluorophosphate (HATU, 9.43 g, 24.80 mmol) in a mixture DMF/DCM 1:1 (60 mL) is added DIPEA (8.64 mL, 49.60 mmol). After complete solubilization, the solution obtained is poured onto molecule 4a. After 2 hours of stirring at room temperature, the resin is filtered, successively washed with DMF (3×60 mL), isopropanol (1×60 mL) and dichloromethane (3×60 mL).

Molecule 6a: Product Obtained by the Reaction Between Molecule 5a and an 80:20 DMF/Piperidine Mixture.

Using a process similar to that used for molecule 4a, applied to molecule 5a, molecule 6a is obtained.

Molecule 7a: Product Obtained by the Reaction Between Molecule 6a and Lauric Acid.

Molecule 7a is obtained using a process similar to that used for molecule 5a, applied to molecule 6a and tolauric acid (4.97 g, 24.80 mmol) in DMF (60 mL), molecule 7a is obtained.

Molecule 8a: Product Obtained by the Reaction Between Molecule 7a and a Dichloromethane/1,1,1,3,3,3-Hexafluoro-2-Propanol (HFIP) 80:20 Mixture.

Molecule 7a is treated with an 80:20 dichloromethane/1,1,1,3,3,3-hexafluoro-2-propanol (HFIP) (60 mL) mixture. After 20 minutes of stirring at room temperature, the resin is filtered and washed with dichloromethane (2×60 mL). The solvents are evaporated under reduced pressure. Two co-evaporations are then carried out on the residue with dichloromethane (60 mL) then with diisopropylether (60 mL). A white solid of molecule 8a is obtained after recrystallization in acetonitrile Yield: 2.63 g (66% in 6 steps)
RMN $^1$H (CDCl$_3$, ppm): 0.87 (6H); 1.09-1.66 (40H); 1.77-1.98 (2H); 2.13-2.29 (4H); 3.24-3.75 (18H); 3.95-4.07 (4H); 4.65-4.70 (1H); 6.23-6.37 (1H); 6.39-6.62 (1H); 6.74-6.91 (1H); 7.38-7.54 (1H).
LC/MS (ESI): 801.6 (calculated ([M+H]$^+$): 801.6).

Molecule 9a: Product Obtained by the Reaction Between Molecule 8a and N-Boc Ethylenediamine.

To a solution of molecule 8a (2.63 g, 3.29 mmol) in chloroform (20 mL) at room temperature are successively added HOBt (654 mg, 4.27 mmol) and BocEDA (580 mg, 3.62 mmol). The mixture is cooled to 0° C. then EDC (819 mg, 4.27 mmol) is added. The medium is stirred for 15 minutes at 0° C. then for 18 h at room temperature. The organic phase is washed with a saturated NH$_4$Cl aqueous solution (2×10 mL), an aqueous solution saturated in NaHCO$_3$ (2×10 mL), and aa saturated NaCl aqueous solution (2×10 mL). The organic phase is dried over Na$_2$SO$_4$, filtered and concentrated under reduced pressure. A white solid of molecule 9a is obtained after purification by chromatography on silica gel (eluent: dichloromethane, methanol).

Yield: 2.37 g (76%)
RMN $^1$H (CDCl$_3$, ppm): 0.87 (6H); 1.08-1.47 (34H); 1.43 (9H); 1:48-170 (7H); 1.78-1.87 (1H); 2.14-2.25 (4H); 3.16-3.71 (22H); 3.92-4.04 (4H); 4.47-4.52 (1H); 5.33 (1H); 6.10 (1H); 6.65-7.01 (1H); 7.11-7.30 (2H); 7.47-7.63 (1H).

Molecule A5a

To a solution of molecule 9a (2.37 g, 2.51 mmol) in dichloromethane (50 mL) at room temperature is added a solution of 4 N HCl in dioxane (6.3 mL) then the medium is stirred for 2 hours at room temperature. After concentration under reduced pressure, the residue is solubilized in dichloromethane (50 mL) then washed with an aqueous solution of 1 N NaOH (2×12.5 mL) and a saturated NaCl aqueous solution (25 mL). The organic phase is dried over Na$_2$SO$_4$, filtered and concentrated under reduced pressure. A white solid of molecule A5a is obtained after recrystallization in acetonitrile Yield: 1.57 g (74%)
RMN $^1$H (CDCl$_3$, ppm): 0.87 (6H); 1.08-1.43 (34H); 1.48-1.71 (7H); 1:74-1.93 (3H); 2.14-2.25 (4H); 2.79-2.86 (2H); 3.17-3.71 (20H); 3.93-4.05 (4H); 4.47-4.54 (1H); 6.08-6.29 (1H); 6.84-7.01 (1H); 7.15-7.32 (2H); 7.50-7.64 (1H).
LC/MS (ESI): 843.6 (calculated ([M+H]$^+$): 843.7).

Example A6A: Molecule A6A

Molecule 10a: Product Obtained by the Hydrogenation of Retinoic Acid.

A solution of retinoic acid (19.0 g, 63.24 mmol) in methanol (450 mL) in the presence of 10% palladium on carbon (1.9 g) is placed under hydrogen atmosphere (1 atm) at room temperature. After overnight, the reaction medium is sinter filtered then the filtrate is concentrated under reduced pressure. A colorless oil of molecule 10a is obtained.

Yield: 19.50 g (99%)
RMN $^1$H (CDCl$_3$, ppm): 0.45-2.01 (35H); 2.10-2.17 (1H); 2.33-2.38 (1H); 11.14 (1H).
LC/MS (ESI): 309.3 (calculated ([M−H]$^+$): 309.3).

Molecule 11a: Product Obtained by the Reaction Between Boc-1-Amino-4,7,10-Trioxa-13-Tridecane Amine (Boc-TOTA) and Molecule 10a.

Using a process similar to that used for the preparation of molecule 9a applied to molecule 10a (19.3 g, 62.15 mmol) and to BocTOTA (23.9 g, 74.58 mmol), an orange oil of molecule 11a is obtained.

Yield: 37.05 g (97%)
RMN $^1$H (CDCl$_3$, ppm): 0.43-1.71 (49H); 2.13-2.17 (1H); 3.17-3.24 (2H); 3.32-3.39 (2H); 3.51-3.66 (12H); 4.77 (0.1H); 4.94 (0.9H); 6.13 (0.9H); 6.29 (0.1H).
LC/MS (ESI): 613.5 (calculated ([M+H]$^+$): 613.5).

Molecule A6a

Using a process similar to that used for the preparation of molecule A5a applied to molecule 11a (34.9 g, 56.94 mmol), an orange oil of molecule A6a is obtained.

Yield: 28.5 g (97%)
RMN $^1$H (CDCl$_3$, ppm): 0.41-1.96 (42H); 2.13 (1H); 2.78 (2H); 3.31-3.36 (2H); 3.53 (4H); 3.55-3.58 (4H); 3.60-3.63 (4H); 6.43 (1H).
LC/MS (ESI): 513.5 (calculated ([M+H]$^+$): 513.5).

Example A8: Molecule A8

Molecule 15a: Product Obtained by the Reaction Between Decanoic Acid and L-Leucine.

Using a process similar to that used for the preparation of molecule 8 and applied to decanoic acid (8.77 g, 50.94 mmol) and to L-leucine (7.00 g, 53.36 mmol), a white solid of molecule 15a is obtained.

Yield: 9.17 g (66%)
RMN $^1$H (DMSO-d6, ppm): 0.82-0.89 (9H); 1.18-1.65 (17H); 2.04-2.14 (2H); 4.19-4.23 (1H); 7.98 (1H); 12.40 (1H).
LC/MS (ESI): 286.2 (calculated ([M+H]$^+$): 286.2).

Molecule 16a: Product Obtained by the Reaction Between Molecule 15a and L-Lysine Methylic Ester.

To a solution of molecule 15a (9.16 g, 32.11 mmol) in THF (160 mL) are successively added triethylamine (8.12 g, 80.27 mmol) and 2-(1H-benzotriazol-1-yl)-1,1,3,3-tetramethyluronium tetrafluoroborate (TBTU) and the medium is stirred for 30 minutes at room temperature. Dichlorhydride methyl ester of L-lysine (3.93 g, 16.86 mmol) is added and the reaction medium is stirred for 3 hours, then concentrated under reduced pressure. The residue is diluted with AcOEt (200 mL), the organic phase is filtered and washed with an aqueous solution of 1 N HCl, then with water, dried over Na$_2$SO$_4$, filtered and concentrated under reduced pressure. A white solid of molecule 16a is obtained after trituration of the residue in acetonitrile Yield: 7.33 g (66%)
RMN $^1$H (DMSO-d6, ppm): 0.80-0.91 (18H); 1.06-1.72 (38H); 2.03-2.16 (4H); 2.91-3.07 (2H); 3.60 (1.15H); 3.61 (1.85H); 4.13-4.28 (2H); 4.33-4.44 (1H); 7.79-7.92 (3H); 8.13-8.26 (1H).
LC/MS(ESI) 695.7 (calculated ([M+H]$^+$): 695.6).

Molecule 17a: Product Obtained by the Saponification of Molecule 16a.

To a solution of molecule 16a (7.33 g, 10.55 mmol) in a THF/methanol/water (105 mL) mixture is added LiOH (505.13 mg, 21.09 mmol) a 0° C., then the medium is stirred for 20 hours at room temperature and concentrated under reduced pressure. The aqueous phase is acidified with a solution of 1 N HCl to pH 1 and the solid formed is filtered, washed with water and dried under reduced pressure resulting in a white solid of molecule 17a.

Yield: 7.09 g (99%)
RMN $^1$H (DMSO-d6, ppm): 0.80-0.89 (18H); 1.18-1.73 (40H); 2.03-2.16 (4H); 2.91-3.05 (2H); 4.03-4.13 (1H); 4.21-4.27 (1H); 4.31-4.40 (1H); 7.79-8.02 (4H).
LC/MS (ESI): 681.7 (calculated ([M+H]$^+$): 681.6).

Molecule 18a: Product Obtained by the Reaction Between Molecule 17a and N-Boc Ethylenediamine.

Using a process similar to that used for the preparation of molecule 16a applied to molecule 17a (7.09 g, 10.41 mmol) and to N-Boc ethylenediamine (1.83 g, 11.45 mmol), a white solid of molecule 18a is obtained after trituration in acetonitrile Yield: 6.64 g (77%)
RMN $^1$H (DMSO-d6, ppm): 0.80-0.91 (18H); 1.15-1.73 (49H); 2.03-2.18 (4H); 2.92-3.13 (6H); 4.05-4.30 (3H); 6.71-6.83 (1H); 7.69-8.23 (5H).
LC/MS (ESI): 824.0 (calculated ([M+H]$^+$): 823.7).

Molecule A8

Using a process similar to that used for the preparation of molecule A5a and applied to molecule 18a (3.00 g, 3.64 mmol), without basic washing, a beige solid of molecule A8 in the form of a hydrochloride salt is obtained after co-evaporation, 4 times, of the residue in methanol.

Yield: 2.66 g (96%)
RMN $^1$H (DMSO-d6, ppm): 0.80-0.91 (18H); 1.15-1.76 (40H); 2.03-2.19 (4H); 1.78-2.89 (2H); 2.91-3.07 (2H); 3.22-3.37 (2H); 4.08-4.14 (1H); 4.17-4.28 (2H); 7.81-8.36 (8H).
LC/MS (ESI): 723.7 (calculated ([M+H]$^+$): 723.6).

Example A9: Molecule A9

Molecule 19a: Methyltetradecanoic-13 Acid

Magnesium in chips (5.50 g, 226.3 mmol) is introduced into a dry three-neck flask under argon The magnesium is covered with anhydrous THF (25 mL) and several drops of 1-bromo-2-methylpropane are added at room temperature to initiate the reaction. After observing an exotherm and of a slight turbidity of the medium, the rest of 1-bromo-2-methylpropane (28.42 g, 207 mmol) diluted in THF (60 mL) is added, drop-by-drop over 1 hour while the temperature of the medium remains stable from 65 to 70° C. The reaction medium is then heated by refluxing for 2 hours.

In a three-neck flask under argon, to a solution of CuCl (280 mg, 2.83 mmol), dissolved in N-methylpyrrolidone (NMP) previously distilled at 0° C., is added, drop-by-drop, a solution of bromoundecanoic-11 acid (25 g, 94.27 mmol) dissolved in THF (60 mL). Then, to this solution is added, drop-by-drop, the solution of organo-magnesium, slightly hot, diluted in THF (50 mL) so as to maintain the temperature of the medium below 25° C. The mixture is then stirred at room temperature for 16 hours. The medium is cooled to 0° C. and the reaction is stopped by slow addition of an aqueous solution of 1 N HCl to pH 1 (300 mL) and the medium is extracted with hexane (100 mL) and ethyl acetate (2×75 mL). After washing the organic phase with an aqueous solution of 1 N HCl (100 mL), water (100 mL) and drying with Na$_2$SO$_4$, the solution is filtered and concentrated under vacuum, resulting in a brown solid. After purification by flash chromatography (cyclohexand, ethyl acetate), a white solid is obtained.

Yield: 18.1 g (79%)
RMN $^1$H (CDCl$_3$, ppm): 0.87 (6H); 1.11-1.18 (2H); 1.20-1.38 (16H); 1.51 (1H); 1.63 (2H); 2.35 (2H).

Molecule 20: Product Obtained by the Reaction Between Molecule 19a and L-Leucine.

To a solution of molecule 19a (18.05 g, 74.46 mmol) in THF (745 mL) at room temperature are successively added DCC (14.63 g, 70.92 mmol) and NHS (8.16 g, 70.92 mmol). After 40 hours of stirring at room temperature, the medium is cooled to 0° C. for 20 minutes, sinter-filtered. L-leucine (9.77 g, 74.46 mmol), DIPEA (86 mL) and water (150 mL) are added to the filtrate. After 20 hours of stirring at room temperature, the medium is diluted with an aqueous solution saturated with NaHCO$_3$ (200 mL). The aqueous phase is washed with ethyl acetate (2×200 mL) and acidified with an aqueous solution of 2 N HCl to pH 1. The precipitate is filtered, rinsed thoroughly with water and dried under vacuum at 50° C. The solid is triturated 3 times in pentane, sonicated, then filtered, resulting in a white solid.

Yield: 18.8 g (75%)
RMN $^1$H (CDCl$_3$, ppm): 0.86 (6H); 0.96 (6H); 1.12-1.18 (2H); 1.20-1.78 (22H); 2.24 (2H); 4.58-4.63 (1H); 5.89 (1H).
LC/MS (ESI): 356.2 (calculated ([M+H]$^+$): 356.6).

Molecule 21a: Product Obtained by the Reaction Between Molecule 20 and Boc-Tri(Ethyleneglycol)Diamine.

To a solution of molecule 20 (16.7 g, 46.97 mmol) in THF (235 mL) at room temperature are added DIPEA (20.3) and TBTU. After stirring for 20 minutes, the Boc-tri(ethyleneglycol)diamine (14 g, 56.36 mmol) is added. After stirring at room temperature for 5 hours, the mixture is concentrated under vacuum. The residue is removed with ethyl acetate (500 mL) washed with a saturated aqueous solution of NaHCO$_3$ (3×200 mL), an aqueous solution of 1 N HCl (3×200 mL), and a saturated NaCl aqueous solution (3×200 mL). After drying with Na$_2$SO$_4$, filtration and concentrated under vacuum, the residue is purified by flash chromatography (cyclohexane, ethyl acetate, methanol), resulting in a colorless oil.

Yield: 23.5 g (85%)
RMN $^1$H (CDCl$_3$, ppm): 0.86 (6H); 0.93 (6H); 1.10-1.17 (2H); 1.19-1.08 (31H); 2.18 (2H); 3.23-3.65 (12H); 4.41-4.56 (1H); 5.12-5.47 (1H); 5.99-6.11 (0.75H); 6.48-6.65 (1H); 7.30-7.40 (0.25H).

Molecule A9

Using a process similar to that used for the preparation of molecule A5a, applied to molecule 21a (23.46 g, 40.04 mmol) without basic washing, the residue obtained after vacuum concentration is triturated in an acetonitrile/acetone mixture. The supernatant is removed and the pasty residue is dried under vacuum. The residue is then triturated in acetone (150 mL) and the white solid of molecule A9 in the form of a hydrochloride salt is filtered, rinsed in acetone, then dried under vacuum.

Yield: 13.0 g (64%)
RMN $^1$H (DMSO-d6, ppm): 0.79-0.90 (12H); 1.09-1.61 (24H); 2.03-2.17 (2H); 2.92-2.98 (2H); 3.15-3.23 (2H); 3.40 (2H); 3.50-3.58 (4H); 3.61 (2H); 4.30-4.23 (1H); 7.88-8.14 (5H).
LC/MS (ESI): 486.4 (calculated ([M−]$^+$): 486.8).

Example A10: Molecule A10

Molecule 22a: Product Obtained by the Reaction Between Octanoyl Chloride and L-Proline.

Using a process similar to that used for the preparation of molecule 11 and applied to octanoyl chloride (150.0 g, 0.922 mol) and to L-proline (212.3 g, 1.844 mol), a colorless oil of molecule 22a is obtained after washes of the organic phase with an aqueous solution of 10% HCl (3×300 mL), a saturated NaCl aqueous solution (300 mL), drying with $Na_2SO_4$, filtration with cotton, concentration under reduced pressure, then the residue is purified by flash chromatography (eluent: DCM, MeOH)

Yield: 134 g (60%)

RMN $^1$H ($CDCl_3$, ppm): 0.87 (3H); 1.10-1.52 (8H); 1.57-1.74 (2H); 1.79-2.52 (6H); 3.37-3.67 (2H); 4.37-4.42 (0.07H); 4.53-5.63 (0.93H); 9.83 (1H).

LC/MS (ESI): 242.1 (calculated ([M+H]$^+$): 242.2).

Molecule 23a: Product Obtained by the Coupling Between Molecule 22a and L-Lysine.

To a solution of molecule 22a (132 g, 0.547 mol) in THF (924 mL) cooled to a temperature less than 5° C. are successively added NHS (66.1 g, 0.574 mol) and DCC (118.5 g, 0.574 mol). After 21 hours of stirring, the precipitated is eliminated by precipitation and the filtrate is added over 30 minutes to a solution of L-lysine (41.98 g, 0.287 mol) in a mixture of deionized water (82 mL) DIPEA (476 mL, 2.735 mol) at 15° C. After 23 hours of stirring at room temperature, the reaction medium is concentrated under reduced pressure resulting in an oily residue which is diluted in water (1.3 L). The aqueous phase is washed twice with AcOEt (2×0.5 L), cooled to a temperature below 10° C., acidified by adding a solution of 6 N HCl (120 mL) to reach a pH of 1, then extracted 3 times with DCM (3×0.6 L). The organic phases are reunited, washed with a saturated solution of NaCl (0.6 L), dried over $Na_2SO_4$ then concentrated under reduced pressure. The foam obtained is taken up into refluxing acetone (240 mL) for 2 hours. After a night at 10° C., pentane (240 mL) is added drop-by-drop. After 1 hour of stirring, the precipitate is recovered by filtration under vacuum, washed with a 1:1 mixture of pentane and acetone (150 mL), then dried under vacuum.

Yield: 83.9 g (52%)

RMN $^1$H ($CDCl_3$, ppm): 0.87 (6H); 1.06-1.78 (25H); 1.80-2.41 (13H); 2.80-3.72 (6H); 4.30-4.39 (0.15H); 4.46-4.70 (2.85H); 7.84 (1H); 7.93 (1H).

LC/MS (ESI): 593.5 (calculated ([M+H]$^+$): 593.4).

Molecule 24: Product Obtained by the Reaction Between Molecule 23a and L-Lysine Methyl Ester.

To molecule 23a (76.26 g, 0.129 mol) are successively added HOPO (3.57 g, 32.1 mmol), dihydrochloride LysOMe (15.0 g, 64.3 mmol) and EDC (34.53 g, 0.18 mol) then DMF (600 mL) previously cooled to 5° C. is added. After dissolution, triethylamine (43.9 mL, 0.315 mol) is added drop-by-drop while maintaining the temperature below 5° C. for 2 more hours after the end of the addition. After a night at room temperature, the reaction medium is poured onto a water/ice mixture (2 kg) and DCM (0.5 L). After 15 minutes of stirring, the phases are separated. The aqueous phase is extracted with DCM (2×0.4 L). The organic phases are reunited, washed with a solution of 1 N HCl (0.5 L) then with a saturated solution of NaCl (0.5 L), dried over $Na_2SO_4$, concentrated under reduced pressure, then the residue is purified by flash chromatography (eluent: DCM, MeOH).

Yield: 56.7 g (67%)

RMN $^1$H ($CDCl_3$, ppm): 0.87 (12H); 1.10-2.40 (82H); 2.86-3.72 (17H); 4.16-4.60 (7H); 6.83-8.01 (6H).

Molecule A10

A solution of molecule 24 (4.0 g, 3.05 mmol) in ethylenediamine (30 mL) is heated to 50° C. overnight. The reaction medium is then diluted with methyl-tetrahydrofurane, then the organic phase is washed 4 times with a saturated solution of NaCl (4×30 mL) then 2 times with water (2×50 mL) before being dried over $Na_2SO_4$ then concentrated under reduced pressure. The residue is solubilized in refluxing acetonitrile for 30 minutes, then the solution is cooled to room temperature while stirring overnight. The white precipitate is then recovered by filtration under vacuum, washed with cold acetonitrile (2×20 mL) then dried under vacuum.

Yield: 3.0 g (74%)

RMN $^1$H ($CDCl_3$, ppm): 0.87 (12H); 1.09-2.37 (84H); 2.74-4.56 (25H); 6.85-8.00 (7H).

LC/MS (ESI): 1338.0 (calculated ([M+H]$^+$): 1338.0).

Example A11: Molecule A11

Molecule A11 is obtained by the conventional method of peptide synthesis in solid phase (SPPS) on 2-chlorotrityle chloride (CTC) (40.0 g, 1.16 mmol/g) resin. Grafting of the first Fmoc-Lys(Fmoc)-OH (1.5 equivalents) amino acid is carried out in DCM (10V), in the presence of DIPEA (3.0 equivalents). Sites which did not react are capped with methanol (0.8 mL/g resin) at the end of the reaction.

The couplings of protected amino acids Fmoc-Glu (OtBu)-OH (2.5 equivalents), Fmoc-Pro-OH (2.5 equivalents) and myristic acid (2.5 equivalents) are carried out in DMF (10V), in the presence of HATU (2.5 equivalents) and DIPEA (3.7 equivalents).

The protective Fmoc groups are removed using a solution of DMF/piperidine 80:20 (10 V). The product is cleaved from the resin using a solution of DCM/HFIP 80:20 (10 V).

After concentration under reduced pressure, the residue is purified by chromatography on silica gel (dichloromethane, methanol).

Yield: 56.5 g (65%)

RMN $^1$H ($CD_3OD$, ppm): 0.90 (6H); 1.22-2.53 (140H); 3.12-3.25 (2H); 3.43-3.80 (4H); 4.17-4.54 (9H).

LC/MS (ESI+): 1894.5 (calculated ([M+Na]$^+$): 1894.2).

Example A12: Molecule A12

Molecule 25: Product Obtained by the Hydrogenation of Farnesol.

To a solution of farnesol (60.00 g, 269.82 mmol) in THF (1200 mL) under argon is added platinum oxide ($PtO_2$, 613 mg, 2.70 mmol) and the medium is placed under 1 atm of dihydrogen then stirred for 6 hours at room temperature. After filtration on a pad of celite rinsed with THF, a black oil of molecule 25 is obtained after concentration under reduced pressure. This compound is used without additional purification.

Yield: 61.60 g (100%)

RMN $^1$H ($CDCl_3$, ppm): 0.85 (3H); 0.87 (6H); 0.90 (3H) 1.01-1.43 (15H); 1.47-1.66 (3H); 3.62-3.76 (2H).

Molecule 26: Product Obtained by the Oxidation of Molecule 25.

To a solution of molecule 25 (61.60 g, 269.68 mmol) in a dichloroethane/water (1350 mL/1080 mL) mixture are successively added tetrabutylammonium bromide (46.95 g, 145.63 mmol), acetic acid (416 mL, 7.28 mol) then $KMnO_4$ (127.85 g, 809.04 mmol) by small fractions while maintaining the temperature from 11 to 13° C. The reaction medium is then stirred for 4 hours 30 minutes, refluxed, cooled to 0° C. then acidified to pH 1 with a 37% HCl solution (50 mL). $Na_2SO_3$ (186.94 g) is added progressively while maintaining the temperature from 0 to 10° C. and the medium is stirred until it becomes completely colorless. The medium is acidified to pH 1 with a 37% solution of HCl, then water (500 mL) and DCM (500 mL) are added. The phases are separated and the aqueous phase is extracted with DCM (2×500 mL). The combined organic phases are washed with an aqueous solution of 10% HCl (400 mL), water (2×400 mL), an aqueous saturated solution in NaCl (400 mL), dried over Na$_2$SO$_4$, filtered and concentrated under reduced pressure. A yellow oil of molecule 26 is obtained after purification by flash chromatography (eluent: cyclohexane, AcOEt).

Yield: 54.79 g (84%)

RMN $^1$H (CDCl$_3$, ppm): 0.85 (3H); 0.87 (6H); 0.97 (3H); 1.03-1.43 (13H); 1.52 (1H); 1.91-2.01 (1H); 2.11-2.18 (1H); 2.32-2.39 (1H).

LC/MS (ESI−): 241.3 (calculated ([M−H]$^-$): 241.2).

Molecule 27: Product Obtained by the Coupling Between Molecule 26 and Methyl-L-Prolinate.

To a solution of molecule 26 (54.70 g, 225.66 mmol) in DCM (1500 mL) at 0° C. are successively added HOBt (3.46 g, 22.57 mmol), DIPEA (117.92, 676.97 mmol), methyl L-prolinate hydrochloride (56.06 g, 338.49 mmol) then EDC (64.89 g, 338.49 mmol). The reaction mixture is stirred at 0° C. for 1 hour then at room temperature for 18 hours. The medium is then diluted with DCM (1000 mL), then washed with an aqueous saturated solution in NaHCO$_3$ (2×1 L), a aqueous solution of 1 N HCl (2×1000 mL) and a saturated aqueous solution of NaCl (2×1000 mL). The organic phase is dried over Na$_2$SO$_4$, filtered and concentrated under reduced pressure, resulting in a yellow oil of molecule 27 which is used without further purification.

Yield: 77.15 g (97%)

RMN $^1$H (DMSO-d$_6$, ppm): 0.79-0.89 (12H); 0.98-1.43 (13H); 1.51 (1H); 1.70-2.32 (7H); 3.33-3.42 (0.4H); 3.46-3.57 (1.6H); 3.59 (2.4H); 3.67 (0.6H); 4.23-4.32 (0.8H); 4.53-4.62 (0.2H).

LC/MS (ESI+): 354.2 (calculated ([M+H]$^+$): 354.3).

Molecule 28: Product Obtained by the Saponification of Molecule 27.

To a solution of molecule 27 (77.15 g, 218.22 mmol) in a mixture of THF/MeOH 1:1 (1454 mL) at 0° C. is added, drop-by-drop, a solution of LiOH (7.84 g, 327.33 mmol) in water (727 mL). The reaction mixture is stirred at 0° C. for 18 hours, then at room temperature for 5 hours. Organic solvents are evaporated under reduced pressure. Water (500 mL), an aqueous solution of 10% HCl (200 mL) and DCM (800 mL) are added and the phases are separated. The aqueous phase is extracted with DCM (2×1 L). The organic phases are reunited, washed with water (500 mL), an aqueous saturated solution of NaCl (500 mL), dried over Na$_2$SO$_4$, filtered and concentrated under reduced pressure, resulting a yellow oil of molecule 28 which is used without further purification.

Yield: 71.72 g (97%)

RMN $^1$H (DMSO-d$_6$, ppm): 0.73-0.95 (12H); 0.95-1.42 (13H); 1.51 (1H); 1.65-2.32 (7H); 3.24-3.64 (2H); 4.13-4.28 (0.8H); 4.37-4.50 (0.2H); 12.44 (1H).

LC/MS (ESI+): 340.2 (calculated ([M+H]$^+$): 340.3).

Molecule A12

Molecule A12 is obtained by the conventional method of peptide synthesis in solid phase (SPPS) on 2-chlorotrityle chloride (CTC) (34.5 g, 1.16 mmol/g) resin.

Grafting of the diamine ethylene (10.0 equivalents) is carried out in DCM (10V), in the presence of DIPEA (10.0 equivalents). Sites which did not react are capped with methanol (0.8 mL/g resin) at the end of the reaction.

The couplings of protected amino acids Fmoc-Lys (Fmoc)-OH (1.5 equivalents), Fmoc-Glu(OMe)-OH (3.0 equivalents) and molecule 28 (3.0 equivalents) are carried out in a DCM/DMF 1:1 mixture (10V), in the presence of HATU (1.0 equivalent in relation to the acid) and DIPEA (2.0 equivalents in relation to the acid).

The protective Fmoc groups are removed using a solution of DMF/piperidine 80:20 (10 V) (after coupling with lysine) or a solution of morpholine at 50% in DMF (after coupling with glutamic acids).

The product is cleaved from the resin using a solution of DCM/TFA 50:50 (10 V). After evaporation, the residue is solubilized in MeTHF (450 mL) and the organic phase is washed with a saturated aqueous solution of NaHCO$_3$ (3×450 mL) and a saturated NaCl aqueous solution (200 mL). After drying with Na$_2$SO$_4$, the organic phase is filtered, concentrated under reduced pressure and the residue is purified by chromatography on silica gel (dichloromethane, methanol, NH$_4$OH).

Yield: 13.95 g (31% in 7 steps).

RMN $^1$H (DMSO-d$_6$, ppm): 0.73-0.91 (24H); 0.96-2.41 (56H); 2.72 (2H); 2.89-3.10 (2H); 3.15-3.26 (2H); 3.26-3.51 (4H); 3.57 (3H); 3.58 (3H); 3.99-4.50 (5H) 6.07 (2H); 7.59-8.39 (5H).

LC/MS (ESI+): 1118.2 (calculated ([M+H]$^+$): 1117.8).

Example A13: Molecule A13

Molecule 29: Product Obtained by Polymerization of γ-Benzyl-L-Glutamate N-Carboxyanhydride Initiated by N-Boc-Ethylenediamine.

In a reactor, γ-benzyl-L-glutamate N-carboxyanhydride (39.44 g, 149.82 mmol) is solubilized in DMF (81 mL) at 25° C. The mixture is then stirred until complete dissolution, cooled to −10° C., then a solution of BocEDA (6.00 g, 37.45 mmol) in DMF (7 mL) is introduced rapidly. The reaction medium is stirred at 0° C. for 3 hours, then a solution of 4 M HCl in 1,4-dioxane (3.33 M, 11.8 mL, 39.29 mmol) is added. The reaction medium is stirred at room temperature, then run over an MeOH/IPE solution (125 mL/495 mL) cooled by an ice bath. After 65 hours of stirring at room temperature, the precipitate is sinter filtered, washed with IPE (2×90 mL) and dried at 30° C. under reduced pressure.

Yield: 21.71 g (54%)

DP (estimated according to RMN $^1$H): 4.9

The average calculated molar mass of molecule 29 in the form of a hydrochloride salt is 1270.9 g/mol.

RMN $^1$H (DMSO-d6, ppm): 1.35 (9H); 1.72-2.09 (9.8H); 2.23-2.60 (9.8H); 2.86-3.19 (4H); 3.85 (1H); 4.14-4.52 (3.9H); 4.86-5.23 (9.8H); 6.33-6.85 (1H); 7.09-7.55 (24.5H); 7.88-8.42 (6.9H); 8.67 (1H).

Molecule 30: Product Obtained by the Coupling Between Myristoyl Chloride and Molecule 29.

After solubilization of molecule 29 in the form of a hydrochloride sale (12.46 g, 9.80 mmol) in DCM (115 mL), the solution is cooled to 0° C. Then triethylamine (2.35 g, 23.24 mmol) and a solution of myristoyl chloride (3.16 g, 12.79 mmol) in DCM (16 mL) are successively added. The reaction medium is stirred at 0° C. for 4 h then at temperature for 2 hours before being run over IPE (920 mL). After 14 hours of stirring at room temperature, the precipitate is filtered, washed by EtOH (2×145 ml, then 100 mL) and dried at 30° C. under reduced pressure.

Yield: 9.77 g (69%)

DP (estimated according to RMN $^1$H): 5.1

The average calculated molar mass of molecule 30 is 1488.7 g/mol.

RMN $^1$H (CDCl$_3$, ppm): 0.87 (3H); 1.07-1.51 (29H); 1.51-1.64 (2H); 1.80-2.75 (22.4H); 2.98-3.73 (4H); 3.84-4.50 (5.1H); 4.86-5.32 (10.2H); 5.71-6.47 (1H); 6.72-8.38 (31.6H).

Molecule A13

To a solution of molecule 30 (4.70 g, 3.16 mmol) in DCM (31 mL) at 0° C. is added TFA (31 mL). The reaction medium is stirred at 0° C. for 2 hours then concentrated under reduced pressure and at room temperature. The residue is returned to DCM (100 mL), then dry concentrated under reduced pressure and at room temperature. The residue is solubilized in DCM (100 mL) and washed with an aqueous solution of carbonate buffer at pH=10.4 (326 mL, then 2×200 mL) then with an aqueous solution of HCl (0.1 N, 2×200 mL). The organic solution is dried over $Na_2SO_4$, filtered, then dry concentrated at 40° C. under reduced pressure.

Yield: 3.96 g (88%)

DP (estimated according to RMN $^1H$): 5.2

The average calculated molar mass of molecule A13 in the form of a hydrochloride salt is 1446.9 g/mol.

RMN $^1H$ (TFA-d, ppm): 0.91 (3H); 1.17-1.47 (20H); 1.60-1.74 (2H); 1.99-2.78 (22.8H); 3.41-4.05 (4H); 4.62-4.83 (5.2H); 5.05-5.35 (10.4H); 6.99-8.02 (26H).

Example A15: Molecule A15

Molecule A15 is obtained by the conventional method of peptide synthesis in solid phase (SPPS) on 2-chlorotrityl chloride (CTC) (16.0 g, 1.16 mmol/g) resin.

Grafting of the diamine ethylene (20.0 equivalents) is carried out in DCM (10V). Sites which did not react are capped with methanol (0.8 mL/g resin) at the end of the reaction.

The couplings of protected amino acids Fmoc-Lys (Fmoc)-OH (3.0 equivalents), Fmoc-Glu(OBn)-OH (4.0 equivalents) and molecule 11 (3.0 equivalents) are carried out in a DCM (10V) (Lys and molecule 11 couplings), or a 1:1 DCM/DMF mixture (10V), in the presence of HATU (1.0 equivalent in relation to the acid) and DIPEA mixture (1.5 equivalents in relation to the acid).

The protective Fmoc groups are removed using a solution of DMF/piperidine 80:20 (10 V) (after coupling with lysine) or a solution of DBU at 1% in DMF (after coupling with glutamic acids)

The product is cleaved from the resin using a solution of DCM/TFA 50:50 (10 V). After evaporation, the residue is solubilized in ethyl acetate (400 mL) and the organic phase is washed with an aqueous solution of carbonate buffer at pH 10 (1 M) (2×400 mL), then a saturated NaCl aqueous solution (400 mL). After drying with $Na_2SO_4$ the organic phase is filtered, concentrated under reduced pressure and the residue is purified by chromatography on silica gel (dichloromethane, methanol, $NH_4OH$), then by recrystallization in acetonitrile.

Yield: 16.20 g (70% in 7 steps).

RMN $^1H$ (DMSO-$d_6$, ppm): 0.85 (6H); 1.11-2.57 (72H); 2.50-5.57 (2H); 2.90-3.08 (4H); 3.36-3.61 (4H); 4.06-4.43 (5H); 5.08 (4H); 7.27-7.40 (10H); 7.51-8.31 (5H).

LC/MS (ESI+): 1242.0 (calculated ([M+H]$^+$): 1241.9).

Example A16: Molecule A16

Molecule 32: Product Obtained by SPPS

Molecule 32 is obtained by the conventional method of peptide synthesis in solid phase (SPPS) on 2-chlorotrityl chloride (CTC) (50.0 g, 1.14 mmol/g) resin.

Grafting of the first Fmoc-Glu(OtBu)-OH (1.3 equivalents) amino acid is carried out in DCM (10V), in the presence of DIPEA (2.6 equivalents). Sites which did not react are capped with methanol (0.8 mL/g resin) at the end of the reaction.

The couplings of protected amino acids Fmoc-Glu (OtBu)-OH (1.3 equivalents), and molecule 11 (3.0 equivalents) are carried out in a DMF (10V), in the presence of HATU (1.0 equivalent in relation to the acid) and DIPEA (1.5 equivalents in relation to the acid).

The protective Fmoc groups are removed using a solution of DMF/piperidine 80:20 (10 V).

The product is cleaved from the resin using a solution of DCM/HFIP 80:20 (10 V).

After concentration under reduced pressure, the residue is purified by trituration in diisopropylether.

Yield: 35.78 g (90%)

RMN $^1H$ (CDCl$_3$, ppm): 0.88 (3H); 1.19-1.35 (20H); 1.43 (9H); 1.44 (9H); 1.55-1.67 (2H); 1.90-2.46 (14H); 3.46-3.54 (1H); 3.63-3.71 (1H); 4.33-4.40 (1H); 4.43-4.52 (2H) 7.35 (0.05H); 7.40 (0.05H); 7.63 (0.95H); 7.94 (0.95H).

LC/MS (ESI+): 696.4 (calculated ([M+H]$^+$): 696.5).

Molecule 33: Product Obtained by the Reaction Between Molecule 32 and N-CBz Ethylenediamine Using a process similar to that used for the preparation of molecule 7 and applied to molecule 32 (30.0 g, 43.11 mmol) and to N-CBz ethylenediamine hydrochloride (CBzE-DA.HCl, 11.93 g, 51.73 mmol), and in the presence of DIPEA (15.0 mL, 86.22 mmol) a beige solid of molecule 33 is obtained. It is used without additional purification.

Yield: 37.6 g (100%)

RMN $^1H$ (CDCl$_3$, ppm): 0.88 (3H); 1.19-1.34 (20H); 1.42 (9H); 1.44 (9H); 1.52-2.54 (16H); 3.16-3.70 (6H); 4.08-4.15 (1H); 4.19-4.25 (1H); 4.43-4.53 (1H); 5.00 (1H) 5.08 (1H); 6.56 (1H); 7.00 (1H); 7.24-7.37 (5H); 7.59 (1H); 8.41 (1H).

LC/MS (ESI+): 872.5 (calculated ([M+H]$^+$): 872.6).

Molecule A16

To a solution of molecule 33 (37.6 g, 43.11 mmol) in methanol (376 mL) is added Pd/Al$_2$O$_3$ (3.76 g) under an atmosphere of argon. The mixture is placed under a hydrogen atmosphere (7 bar) and stirred at room temperature for 72 hours. After filtration of the catalyst on P4, then on an Omnipore 0.2 μm PTFE hydrophilic membrane, the filtrate is concentrated under reduced pressure, resulting in molecule A16 in the form of a sticky oil.

Yield: 31.06 g (98%)

RMN $^1H$ (CDCl$_3$, ppm): 0.88 (3H); 1.19-1.35 (20H); 1.43 (9H); 1.46 (9H); 1.56-1.67 (2H); 1.92-2.12 (6H); 2.24-2.54 (8H); 2.71 (2H); 2.90 (2H) 3.22-3.32 (1H); 3.42-3.51 (1H); 3.55-3.64 (1H) 3.73-3.81 (1H); 4.13-4.21 (1H); 4.26-4.33 (1H); 4.39-4.48 (1H); 7.10 (1H); 7.71 (1H); 8.45 (1H).

LC/MS (ESI+): 738.5 (calculated ([M+H]$^+$): 738.5).

Molecule A17

Molecule A17 is obtained by the conventional method of peptide synthesis in solid phase (SPPS) on 2-chlorotrityl chloride (CTC) (64.66 g, 1.16 mmol/g) resin. Grafting of the diamine ethylene (10.0 equivalents) is carried out in DCM (10V), in the presence of DIPEA (10.0 equivalents). Sites which did not react are capped with methanol (0.8 mL/g resin) at the end of the reaction.

The couplings of protected amino acids Fmoc-Glu (OtBu)-OH (1.5 equivalents), and molecule 28 (1.5 equivalents) are carried out in a DCM/DMF 1:1 (10V) mixture for the coupling of glutamic acid, or in DMF (10V), for the coupling of molecule 28, in the presence of HATU (1.0 equivalent in relation to the acid) and DIPEA (2.0 equivalents in relation to the acid).

The protective Fmoc groups are removed using a solution of DMF/morpholine 50:50 (10 V).

The product is cleaved from the resin using a solution of DCM/TFA 50:50 (10 V). After evaporation, the residue is solubilized in MeTHF (500 mL) and the organic phase is washed with a 5% aqueous solution of $Na_2CO_3$ (3×250 mL), then the aqueous phases are extracted with MeTHF (1×150 mL). The reunited organic phases are dried over $Na_2SO_4$ and filtered. A HCl solution in MeOH (1.25 M) is added, then the medium is concentrated under reduced pressure. The residue is purified on silica gel (dichloromethane, methanol), resulting in the hydrochloride salt of molecule A17 in the form of a light brown solid.

Yield: 12.48 g (30% in 5 steps).

RMN $^1$H (DMSO-$d_6$, ppm): 0.76-0.90 (12H); 0.97-1.41 (13H); 1.45-1.55 (1H); 1.68-2.40 (11H); 2.77-2.92 (2H); 3.20-3.64 (4H); 3.57 (3H); 4.15-4.49 (2H); 7.90-8.48 (5H).

LC/MS (ESI+): 525.5 (calculated ([M+H]$^+$): 525.4).

Example A18: Molecule A18

Molecule 34: Product obtained by the hydrogenation of phytol.

To a solution of phytol (260.00 g, 878.78 mmol) in ethanol (1.25 L) under argon is added Raney Nickel at 50% in water (30.75 g, 175.36 mmol). The medium is placed under 1 bar of dihydrogen, then stirred for 8 hours at room temperature. After filtration on a celite/silica/celite pad and rinsing with ethanol, a colorless oil of molecule 34 is obtained after concentration under reduced pressure.

Yield: 261.40 g (quant.)

RMN $^1$H (CDCl$_3$, ppm): 0.84 (6H); 0.86 (6H); 0.89 (3H) 1.00-1.46 (22H); 1.46-1.68 (3H); 3.61-3.73 (2H).

Molecule 35: Product obtained by the oxidation of molecule 34.

Using a process similar to that used for the preparation of molecule 26 applied to molecule 34 (29.00 g, 97.13 mmol), a yellow oil of molecule 35 is obtained.

Yield: 28.70 g (94%)

RMN $^1$H (CDCl$_3$, ppm): 0.84 (6H); 0.86 (6H); 0.97 (3H); 1.00-1.41 (20H); 1.52 (1H); 1.96 (1H); 2.14 (1H); 2.35 (1H); 11.31 (1H).

LC/MS (ESI): 311.1 (calculated ([M−H]$^-$): 311.3).

Molecule 36: Product Obtained by the Coupling Between Molecule 35 and Methyl-L-Prolinate.

Using a process similar to that used for the preparation of molecule 27 applied to molecule 35 (18.00 g, 57.59 mmol), and to methyl-L-prolinate (14.31 g, 86.39 mmol), a yellow oil of molecule 36 is obtained.

Yield: 23.20 g (95%)

RMN $^1$H (DMSO-$d_6$, ppm): 0.78-0.89 (15H); 0.97-1.43 (20H); 1.43-1.56 (1H); 1.70-1.96 (4H); 1.96-2.32 (3H); 3.33-3.56 (2H); 3.59 (0.6H); 3.67 (2.4H); 4.27 (0.8H); 4.57 (0.2H).

LC/MS (ESI): 424.4 (calculated ([M+H]$^+$): 424.4).

Molecule 37: Product Obtained by the Saponification of Molecule 36.

Using a process similar to that used for the preparation of molecule 28 applied to molecule 36 (21.05 g, 49.68 mmol), a yellow oil of molecule 37 is obtained.

Yield: 20.40 g (99%)

RMN $^1$H (DMSO-$d_6$, ppm): 0.77-0.91 (15H); 0.97-1.43 (20H); 1.43-1.56 (1H); 1.67-1.96 (4H); 1.96-2.29 (3H); 3.26-3.56 (2H); 4.20 (0.8H); 4.41 (0.2H).

LC/MS (ESI): 410.3 (calculated ([M+H]$^+$): 410.4).

Molecule A18

Molecule A18 is obtained by the conventional method of peptide synthesis in solid phase (SPPS) on 2-chlorotrityle chloride (CTC) (26.72 g, 1.16 mmol/g) resin.

Using a process similar to that used for the preparation of molecule A17, applied to 4,7,10-trioxa-1,13-tridecanediamine (TOTA, 68.30 g, 310.0 mmol), to Fmoc-Glu(OMe)-OH (23.77 mmol, 62.00 mmol) and to molecule 37 (19.04 g, 46.50 mmol), a yellow oil of molecule A18 in hydrochloride form is obtained.

Yield: 5.53 g (23% in 5 steps).

RMN $^1$H (DMSO-$d_6$, ppm): 0.76-0.89 (15H); 0.97-2.38 (36H); 2.77-2.87 (2H); 3.00-3.17 (3H); 3.32-3.54 (13H); 3.57 (3H); 4.09-4.18 (0.75H); 4.20-4.29 (1H); 4.39-4.47 (0.25H); 7.63-8.36 (5H).

LC/MS (ESI+): 755.7 (calculated ([M+H]$^+$): 755.6).

Molecule A19

Molecule A19 is synthesized in the same way as molecule A16, by using molecule 14 instead of molecule 11 during the SPPS stage.

Overall yield (3 stages): 32.6 g (81%)

RMN $^1$H (CDCl$_3$, ppm): 0.88 (3H); 1.20-1.35 (16H); 1.43 (9H); 1.46 (9H); 1.56-1.68 (2H); 1.93-2.11 (6H); 2.24-2.55 (10H); 2.85 (2H); 3.19-3.29 (1H); 3.38-3.48 (1H); 3.55-3.64 (1H) 3.74-3.82 (1H); 4.14-4.21 (1H); 4.25-4.32 (1H); 4.41-4.50 (1H); 7.03 (1H); 7.69 (1H); 8.42 (1H).

LC/MS (ESI): 710.4 (calculated ([M+H]$^+$): 710.5).

Example A20: Molecule A20

Molecule A20 is obtained by the conventional method of peptide synthesis in solid phase (SPPS) on 2-chlorotrityle chloride (CTC) (40.00 g, 1.16 mmol/g) resin. Grafting of the diamine ethylene (20.0 equivalents) is carried out in DCM (10V). Sites which did not react are capped with methanol (0.8 mL/g resin) at the end of the reaction. The couplings of protected amino acids Fmoc-Lys(Fmoc)-OH (1.5 equivalents), Fmoc-Glu(OtBu)-OH (2.5 equivalents) and molecule 11 (2.5 equivalents) are carried out in DMF (10 V), in the presence of HATU (1.0 equivalent in relation to the acid) and DIPEA (1.5 equivalents in relation to the acid).

The protective Fmoc groups are removed using a solution of DMF/piperidine 80:20 (10 V).

The product is cleaved from resin using a solution of DCM/TFA 50:50 (10 V). After evaporation, the residue is solubilized in water (600 mL), the pH of the solution is adjusted to 7 by adding a solution of 5 N NaOH, then the product is lyophilized. The lyophilisate is purified by column chromatography on silica gel (dichloromethane, methanol, NH$_4$OH), resulting in molecule A20 in the form of a white solid.

Yield: 24.6 g (50% in 7 steps).

RMN $^1$H (MeOD-d4, ppm): 0.90 (6H); 1.18-2.45 (68H); 2.45-2.60 (2H); 3.05-3.11 (2H); 3.11-3.19 (1H); 3.23-3.33 (1H); 3.43-3.66 (4H); 3.82-3.94 (2H); 4.10-4.51 (5H).

LC/MS (ESI+): 1061.9 (calculated ([M+H]$^+$): 1061.8).

Part B—Synthesis of Hydrophobic Co-Polyamino Acids
i) Co-Polyamino Acids According to Formulas XXX, XXXb and XXXa
| No. | CO-POLYAMINO ACIDS BEARING CARBOXYLATE CHARGES AND HYDROPHOBIC RADICALS |
|---|---|
| B1 | 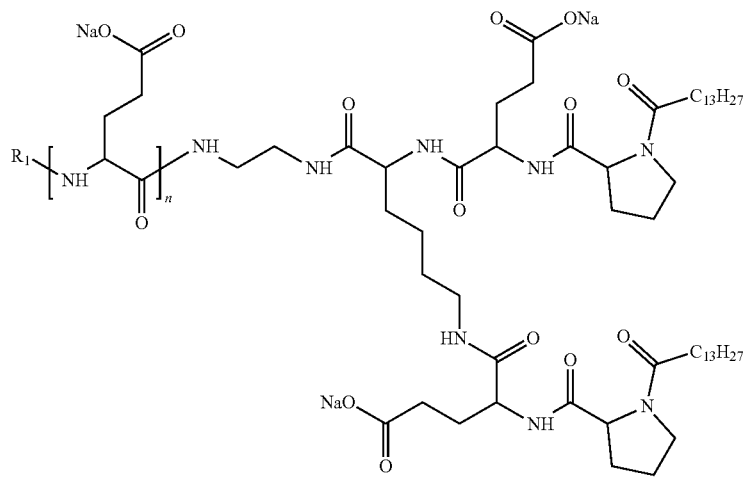<br>i = 0.038, DP = 26<br>$R_1$ = H or pyroglutamate |
| B2 | 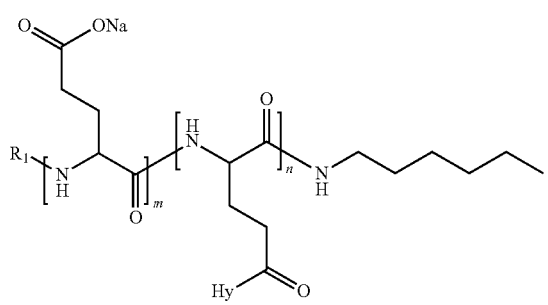<br>i = 0.15, DP (m + n) = 40<br><br>Hy = *—NH—... (structure shown)<br>$R_1$ = H or pyroglutamate |

-continued
| No. | CO-POLYAMINO ACIDS BEARING CARBOXYLATE CHARGES AND HYDROPHOBIC RADICALS |
|---|---|
| B3 | 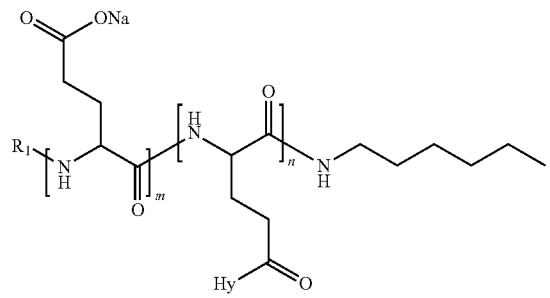 i = 0.15, DP (m + n) = 40 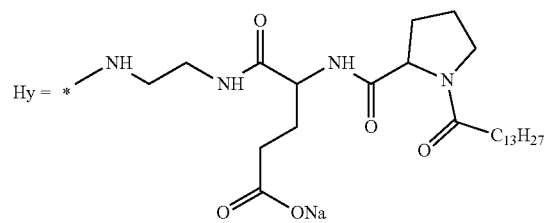 $R_1$ = H or pyroglutamate |
| B4 | 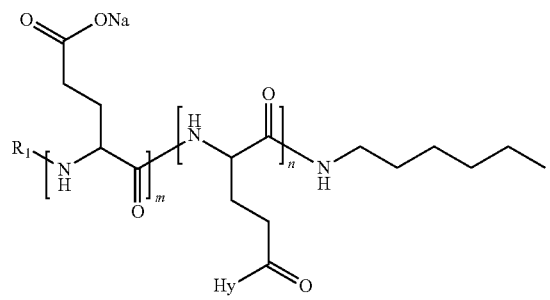 i = 0.15, DP (m + n) = 40 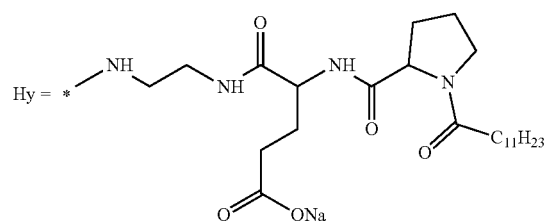 $R_1$ = H or pyroglutamate |
| B5 | 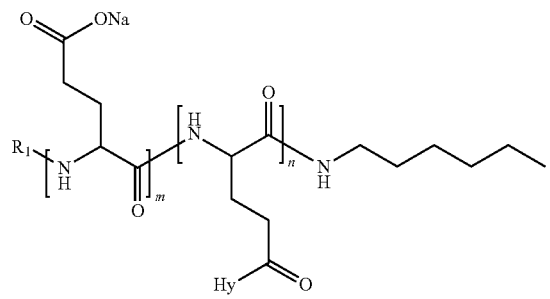 i = 0.15, DP (m + n) = 40 |

-continued
| No. | CO-POLYAMINO ACIDS BEARING CARBOXYLATE CHARGES AND HYDROPHOBIC RADICALS |
|---|---|
| | 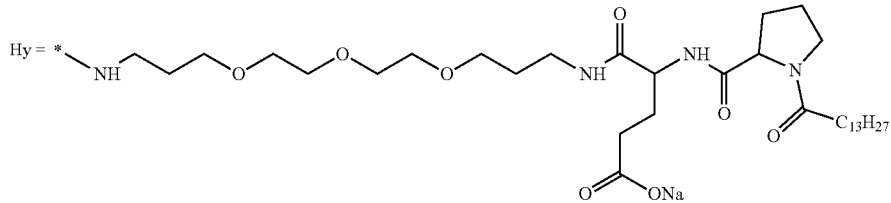
$R_1$ = H or pyroglutamate |
| B7 | 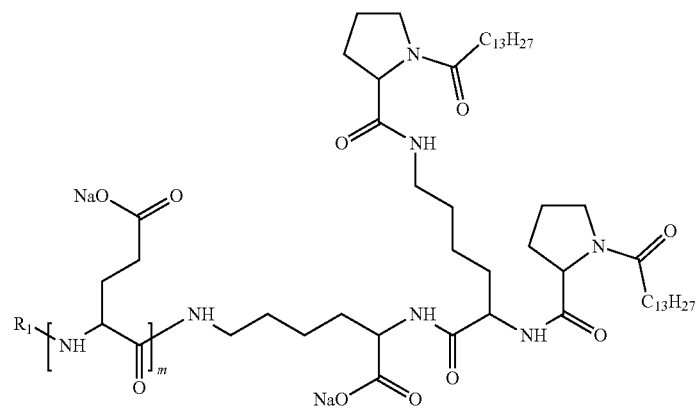
i = 0.038, DP = 26
$R_1$ = H or pyroglutamate |
| B13 | 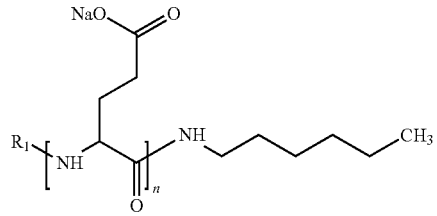
i = 0.042, DP = 24 |
| | 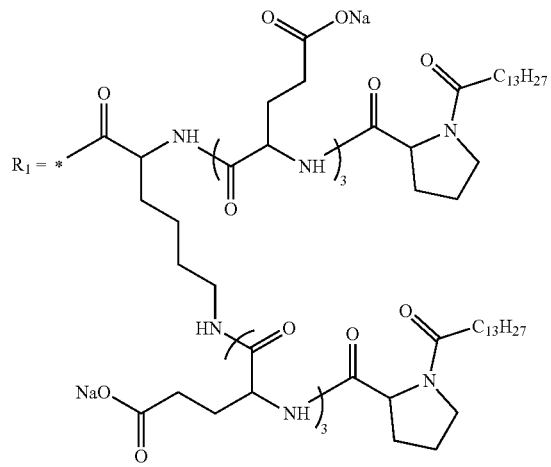 |

| No. | CO-POLYAMINO ACIDS BEARING CARBOXYLATE CHARGES AND HYDROPHOBIC RADICALS |
|---|---|
| B14 | 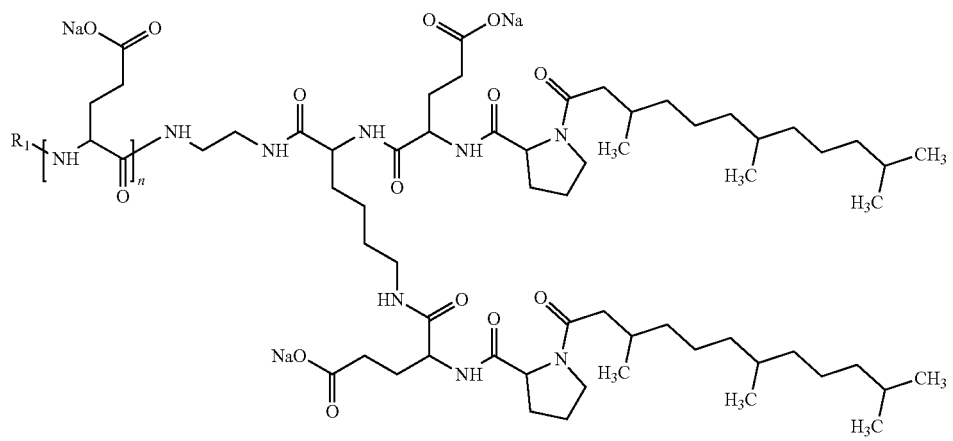<br>$i = 0.042$, DP = 24<br>$R_1$ = H or pyroglutamate |
| B15 | 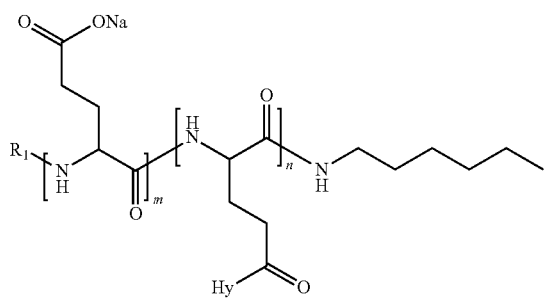<br>$i = 0.15$, DP (m + n) = 40<br>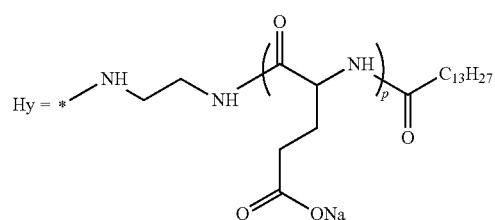<br>DP (p) = 5.2<br>$R_1$ = H or pyroglutamate |

| No. | CO-POLYAMINO ACIDS BEARING CARBOXYLATE CHARGES AND HYDROPHOBIC RADICALS |
|---|---|
| B17 | 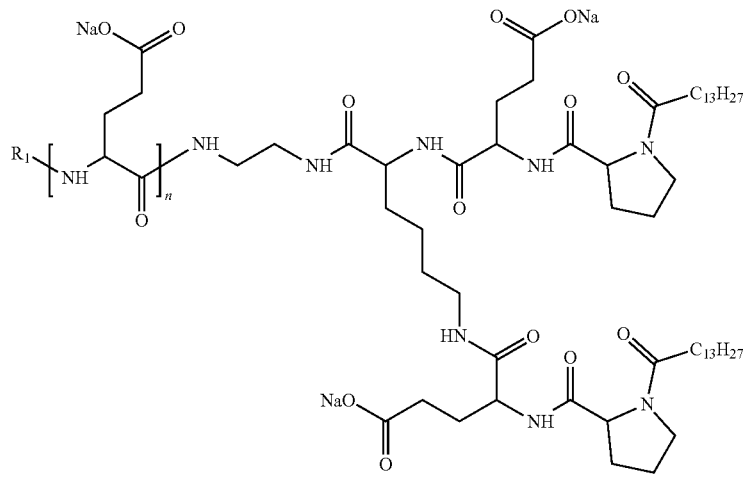<br>i = 0.1, DP = 10<br>$R_1$ = H or pyroglutamate |
| B18 | 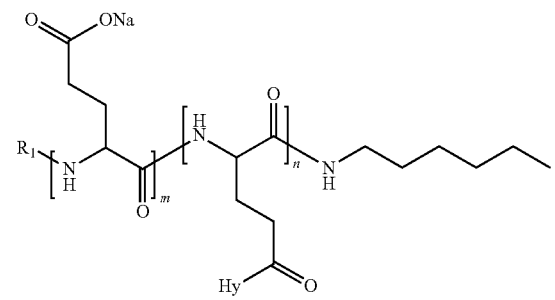<br>i = 0.15, DP (m + n) = 40<br><br>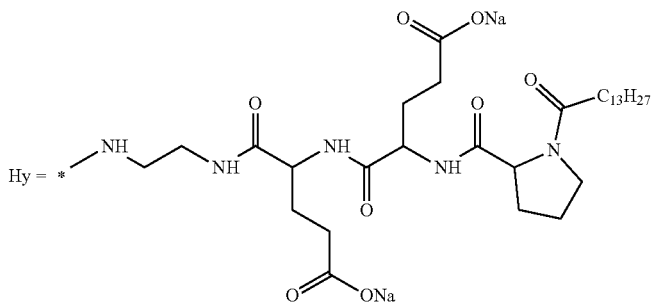<br>$R_1$ = H or pyroglutamate |
| B19 | 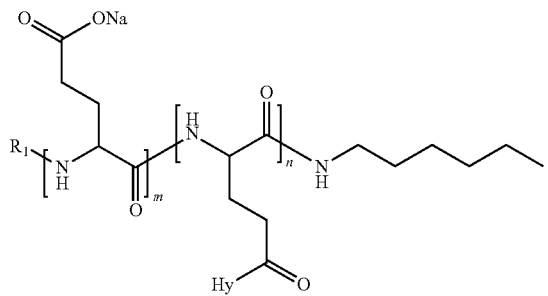<br>i = 0.15, DP (m + n) = 40 |

-continued
| No. | CO-POLYAMINO ACIDS BEARING CARBOXYLATE CHARGES AND HYDROPHOBIC RADICALS |
|---|---|
| | 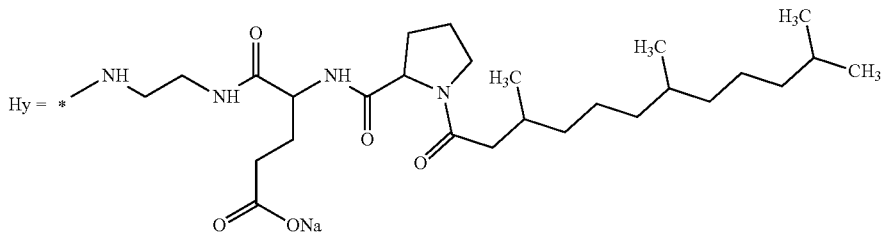<br>$R_1$ = H or pyroglutamate |
| B20 | 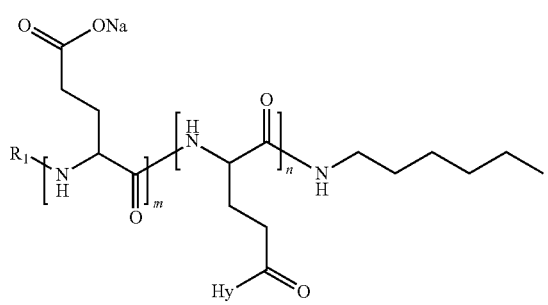<br>i = 0.15, DP (m + n) = 40<br>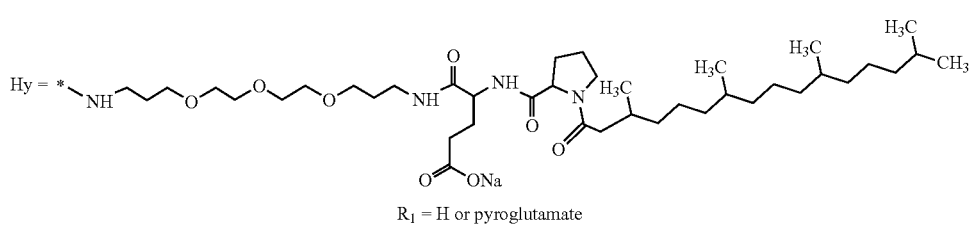<br>$R_1$ = H or pyroglutamate |
| B21 | 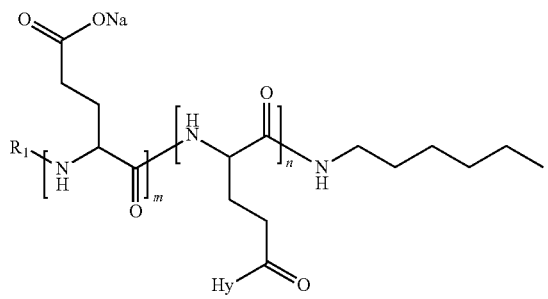<br>i = 0.15, DP (m + n) = 40<br>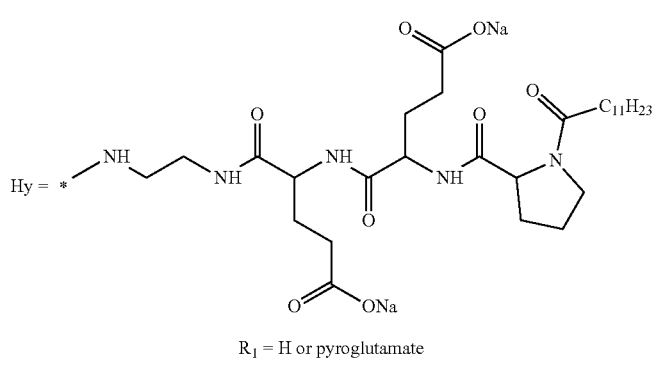<br>$R_1$ = H or pyroglutamate |

| No. | CO-POLYAMINO ACIDS BEARING CARBOXYLATE CHARGES AND HYDROPHOBIC RADICALS |
|---|---|
| B22 | 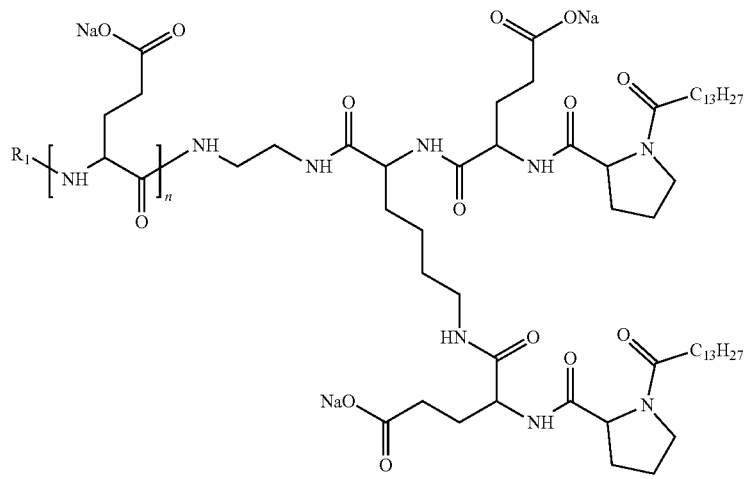 i = 0.05, DP = 20<br>$R_1$ = H or pyroglutamate |

Co-Polyamino Acid B1: Sodium Poly-L-Glutamate Modified at One of its Extremities by Molecule A1 and with a Molar Mass by Number (Mn) of 2800 g/Mol In a previously oven-dried flask, γ-benzyl-L-glutamate N-carboxyanhydride (8.95 g, 34 mmol) is solubilized in anhydrous DMF (34 mL). The mixture is cooled to 4° C., then a solution of molecule A1 (1.64 g, 1.55 mmol) in chloroform (6.6 mL) is quickly introduced. The mixture is stirred from 4° C. to room temperature for 68 hours, then heated to 65° C. for 2 hours. Half of the solvent is distilled under reduced pressure, then the reaction medium is cooled to room temperature and poured drop-by-drop into diisopropylether (300 mL) being stirred. The white precipitate is recovered by filtration, washed with diisopropylether (5×50 mL), then dried under reduced pressure at 30° C. in order to obtain a white solid. The solid (7.9 g) is diluted in TFA (30 mL), and a 33% hydrobromic acid (HBr) solution in acetic acid (21 mL, 120 mmol) is then added, drop-by-drop, at 0° C. The solution is stirred for 2 hours at room temperature, then dripped, drop-by-drop over a 1:1 mixture (v/v) of diisopropylether/water while stirring (360 mL). After stirring for 2 hours, the heterogeneous mixture is allowed to rest overnight. The white precipitate is recovered by filtration, washed successively with IPE (2×30 mL) then with water (2×30 mL). The solid obtained is solubilized in water (200 mL) while adjusting the pH to 7 by adding a 1 N aqueous soda solution. Water (65 mL) is added. The mixture is filtered through a 0.45 μm filter, then purified by ultrafiltration against a 0.9% NaCl solution and then water until the conductimetry of the permeate is less than 50 S/cm. The co-polyamino acid is then concentrated to about theoretical 25 g/L, the pH is adjusted to 7 and the aqueous solution is filtered through 0.2 μm. This solution is diluted with water and acetone in order to obtain a solution at 12 g/L containing 30% acetone mass, then it is filtered through an activated carbon filter (3M R53SLP). The acetone is distilled (40° C., 100 mbar) and the solution is purified by ultrafiltration against a 0.9% NaCl solution, then water, until the conductrimetry of the permeate is less than 50 μS/cm. The co-polyamino acid solution is then concentrated and the pH is adjusted to 7. The aqueous solution is filtered through 0.2 μm and stored at 4° C.

Dry extract: 17.8 mg/g

DP (estimated according to RMN $^1$H): 26

According to RMN $^1$H: i=0.038

The average calculated molar mass of co-polyamino acid B1 is 4994 g/mol.

Organic HPLC-SEC (PEG calibrating): Mn=2800 g/mol

Co-Polyamino Acid B2: Sodium Poly-L-Glutamate Modified by Molecule A2, the Esters of which are Saponified and Having a Number-Average Molar Mass (Mn) of 5200 g/Mol Co-polyamino acid B2-1: poly-L-glutamic acid obtained from the polymerization of γ-benzyl-L-glutamate N-carboxyanhydride initiated by hexylamine In a jacketed reactor, γ-benzyl-L-glutamate N-carboxyanhydride (500 g, 1.90 mol) is solubilized in anhydrous DMF (1100 mL). The mixture is then stirred until completely dissolved, cooled to 0° C., then hexylamine (6.27 mL, 47.5 mmol) is quickly introduced. The mixture is stirred at 0° C. for 5 h, from 0° C. to 20° C. for 7 h, then at 20° C. for 7 h. The reaction medium is then heated to 65° C. for 2 h, cooled to 55° C. and methanol (3300 mL) is introduced over 1 h 30. The reaction mixture is then cooled to 0° C. and stirred for 18 hours. The white precipitate is recovered by filtration, washed with diisopropylether (2×800 mL) then dried under reduced pressure at 30° C. resulting in a poly(gamma-benzyl-L-glutamique) acid (PBLG).

To a solution of PBLG (180 g) in N,N-dimethylacetamide (DMAc, 450 mL) is added Pd/Al$_2$O$_3$ (36 g) under an argon atmosphere. The mixture is placed under a hydrogen atmosphere (10 bar) and stirred at 60° C. for 24 hours. After cooling to room temperature and filtration of the catalyst on P4 sintered, then filtration through a 0.2 μm Omnipore PTFE hydrophilic membrane, a solution of water at pH 2 (2700 mL) is poured drop-by-drop over the DMAc solution, over a period of 45 minutes while stirring. After 18 hours of stirring, the white precipitate is recovered by filtration, washed with water (4×225 mL), then dried under reduced pressure at 30° C.

Co-Polyamino Acid B2

Co-polyamino acid B2-1 (15.0 g) is solubilized in DMF (230 mL) at 40° C., then N-methylmorpholine (NMM, 11.57 g, 114.4 mmol) is added. At the same time, molecule A2 in the form of a hydrochloride salt (10.17 g, 17.2 mmol) is suspended in DMF (250 mL) and triethylamine (2.39 mL, 17.2 mmol) is added, then the mixture is slightly heated while stirring, until completely dissolved. To the co-polyamino acid solution, cooled to 25° C., are successively added, the solution of molecule A2, of N-oxyde 2-hydroxypyridine (HOPO, 3.81 g, 34.3 mmol) then EDC (6.58 g, 34.3 mmol). The reaction medium is stirred at 25° C. for 2 h, filtered through a 0.2 mm woven filter and dripped drop-by-drop over 2.6 L of water containing 15% NaCl by mass and HCl (pH 2) while stirring. At the end of the addition, the pH is readjusted to 2 with a solution of 1 N HCl, and the suspension is allowed to rest overnight. The precipitate is collected, then rinsed 2×100 mL of water. The white solid obtained is solubilized in 1.2 L of water by slow addition of an aqueous solution of 1 N NaOH until pH 7, while stirring, then the solution is filtered through a 0.45 μm filter. Ethanol (30% by mass) is added, then the solution is filtered through an activated carbon filter (3M R53SLP). The solution of 10 N NaOH is slowly added, while stirring up to pH 13, then the mixture is stirred for 2 hours. After neutralization to pH 7 by adding a 37% HCl solution, the clear solution obtained is purified by ultrafiltration against a 0.9% solution of NaCl, then water, until the conductimetry of the permeate is less than 50 μS/cm. The co-polyamino acid solution is then concentrated and the pH is adjusted to 7. The aqueous solution is filtered through 0.2 μm and stored at 4° C.

Dry extract: 22.6 mg/g
DP (estimated according to RMN $^1$H): 40
According to RMN $^1$H: i=0.15
The average calculated molar mass of co-polyamino acid B2 is 9301 g/mol.
Organic HPLC-SEC (PEG calibrating): Mn=5200 g/mol.

Co-Polyamino Acid B3: Sodium Poly-L-Glutamate Modified by Molecule A3, the Ester of which is Saponified and Having a Number-Average Molar Mass (Mn) of 4900 g/Mol Co-polyamino acid B2-1 (12.0 g) is solubilized in DMF (92 mL) at 40° C., then N-methylmorpholine (NMM, 9.25 g, 91.5 mmol) is added. At the same time, a solution of molecule A3 in the form of a hydrochloride salt (7.51 g, 13.7 mmol) and of N,N-diisopropylethylamine (DIPEA, 2.39 mL, 13.7 mmol) in DMF (27 mL) is prepared. To the co-polyamino acid solution, cooled to 25° C., are successively added, the solution of molecule A3, of N-oxyde 2-hydroxypyridine (HOPO, 3.05 g, 27.4 mmol). The mixture is cooled to 0° C. then EDC (5.26 g, 27.4 mmol) is added. After 5 minutes at 0° C., the reaction medium is stirred at 25° C. for 2 h, filtered through a 0.2 mm fabric filter and poured drop-by-drop over 950 L of water containing 15% NaCl by mass and HCl (pH 2) while stirring. At the end of the addition, the pH is readjusted to 2 with a solution of 1 N HCl, and the suspension is allowed to rest overnight. The precipitate is collected, then rinsed 3×100 mL of water. The solid obtained is solubilized in 1 L of water by slow addition of an aqueous solution of 1 N NaOH until pH 7, while stirring. Once completely solubilized, the pH is adjusted to pH 12 over 2 hours then to pH 13 over 1 hour by adding a 10 N NaOH solution. After neutralization to pH 7 by adding a 37% HCl solution, this solution is diluted with water and ethanol in order to obtain a 12 g/L solution containing 30% ethanol by mass, then it is filtered with an activated carbon filter (3M R53 SLP). The solution is filtered through a 0.45 m filter, then purified by ultrafiltration against a 0.9% NaCl solution, until the conductimetry of the permeate is less than 50 μS/cm. The co-polyamino acid solution is then concentrated and the pH is adjusted to 7. The aqueous solution is filtered through 0.2 μm and stored at 4° C.

Dry extract: 20.6 mg/g
DP (estimated according to RMN $^1$H): 40
According to RMN $^1$H: i=0.15
The average calculated molar mass of co-polyamino acid B3 is 8977 g/mol.
Organic HPLC-SEC (PEG calibrating): Mn=4900 g/mol.

Co-Polyamino Acid B4: Sodium Poly-L-Glutamate Modified by Molecule A4, the Ester of which is Saponified and Having a Number-Average Molar Mass (Mn) of 4700 g/Mol Using a process similar to that used for the preparation of co-polyamino acid B3 applied to a hydrochloride salt of molecule A4 (7.12 g, 13.7 mmol) and to co-polyamino acid B2-1 (12.0 g), a sodium poly-L-glutamate modified by molecule A4 for which the ester is saponified is obtained.

Dry extract: 19.4 mg/g
DP (estimated according to RMN $^1$H): 40
According to RMN $^1$H: i=0.15
The average calculated molar mass of co-polyamino acid B4 is 8809 g/mol.
Organic HPLC-SEC (PEG calibrating): Mn=4700 g/mol.

Co-Polyamino Acid B5: Sodium Poly-L-Glutamate Modified by Molecule A5, the Ester of which is Saponified and Having a Number-Average Molar Mass (Mn) of 5400 g/Mol Using a process similar to that used for the preparation of co-polyamino acid B3 applied to a hydrochloride salt of molecule A5 (9.71 g, 13.7 mmol) and to co-polyamino acid B2-1 (12.0 g), a sodium poly-L-glutamate modified by molecule A5 for which the ester is saponified is obtained.

Dry extract: 20.8 mg/g
DP (estimated according to RMN $^1$H): 40
According to RMN $^1$H: i=0.15
The average calculated molar mass of co-polyamino acid B5 is 9939 g/mol.
Organic HPLC-SEC (PEG calibrating): Mn=5400 g/mol.

Co-Polyamino Acid B7: Sodium Poly-L-Glutamate Modified at One of its Extremities by Molecule A7 and Having a Number-Average Molar Mass (Mn) of 2500 g/Mol Using a process similar to that used for the preparation of co-polyamino acid B1 applied to molecule A7 (2.50 g, 2.74 mmol) and to γ-benzyl-L-glutamate N-carboxyanhydride (15.89 g, 60.4 g), a sodium poly-L-glutamate modified at one of its extremities by molecule A7 is obtained.

Dry extract: 20.3 mg/g
DP (estimated according to RMN $^1$H): 26
According to RMN $^1$H: i=0.038
The average calculated molar mass of co-polyamino acid B7 is 3893 g/mol.
Organic HPLC-SEC (PEG calibrating): Mn=2500 g/mol Co-Polyamino Acid B13: Sodium Poly-L-Glutamate Modified at One of its Extremities by Molecule all for which the Esters are Deprotected and Having a Number-Average Molar Mass (Mn) of 3000 g/Mol In a jacketed reactor, γ-benzyl-L-glutamate N-carboxyanhydride (24.50 g, 93.05 mmol) is solubilized in anhydrous DMF (55 mL). The mixture is then stirred until completely dissolved, cooled to 0° C., then hexylamine (0.56 mL, 4.23 mmol) is quickly introduced. The mixture is stirred at 0° C. for 48 h then a solution of molecule A11 (9.51 g, 5.08 mmol) in DMF (50 mL), HOPO (564 mg, 5.08 mmol) and EDC (973 mg, 5.08 mmol) are added successively. The reaction medium is stirred at 0° C. for 1 h, from 0° C. to 20° C. for 2 h, then at 20° C. for 16 h. This solution is then poured over a 1:1 H₂O/MeOH mixture (10 V) at room temperature while stirring. After 4 hours, the white precipitate is recovered by filtration, washed with diisopropyl ether (2×100 mL), water (2×100 mL) and a 1:1 H₂O/MeOH mixture (2×100 mL), then dried under reduced pressure.

The solid obtained is solubilized in TFA (220 mL) and stirred at room temperature for 2 hours 30 minutes. This solution is then poured into water (10V) at room temperature and while stirring. After 2 hours 30 minutes of stirring, the white precipitate is recovered by filtration, washed with water (2×200 mL), then dried under reduced pressure.

The solid obtained is solubilized in N,N-dimethylacetamide (DMAc, 210 mL) is added Pd/Al$_2$O$_3$ (2.1 g) under an argon atmosphere. The mixture is placed under a hydrogen atmosphere (6 bar) and stirred at 60° C. for 24 hours. After cooling to room temperature and filtration of the catalyst on sintered P4, then filtration through an Omnipore 0.2 μm PTFE hydrophilic membrane, a solution of water at pH 2 containing 15% NaCl (6 V) is dripped drop-by-drop on the DMAc solution, over a period of 45 minutes and while stirring. After 18 hours of stirring, the white precipitate is recovered by filtration, washed with water, then dried under reduced pressure. The solid obtained is solubilized in water (600 mL) while adjusting the pH to 7 by adding a 1N aqueous soda solution. The pH is then adjusted to pH12 and the solution is stirred for 1 hour. After neutralization to pH 7, the solution is filtered with 0.2 μm, diluted with ethanol in order to obtain a solution containing 30% by mass of ethanol, then filtered with an activated carbon filter (3M R53SLP). The solution is filtered through a 0.45 μm filter, then purified by ultrafiltration against a 0.9% NaCl solution, until the conductimetry of the permeate is less than 50 μS/cm. The co-polyamino acid solution is then concentrated and the pH is adjusted to 7. The aqueous solution is filtered through 0.2 μm and stored at 4° C.

Dry extract: 23.5 mg/g
DP (estimated by RMN ¹H)=24 therefore i=0.042
The average calculated molar mass of co-polyamino acid B13 is 5377 g/mol.
Organic HPLC-SEC (PEG calibrating): Mn=3000 g/mol.
Co-Polyamino Acid B14: Sodium Poly-L-Glutamate Modified at One of its Extremities by Molecule A12 for which the Esters are Deprotected and Having a Number-Average Molar Mass (Mn) of 3300 g/Mol
Co-Polyamino Acid B14-1: Poly-L-Benzylglutamate Modified at One of its Extremities by Molecule A12.

In a previously oven-dried flask, γ-benzyl-L-glutamate N-carboxyanhydride (50.00 g, 189.39 mmol) is solubilized in anhydrous DMF (65 mL). The mixture is then stirred until completely dissolved, cooled to 0° C., then a solution of molecule A12 (9.65 g, 8.63 mmol) in DMF (50 mL) is quickly introduced. The mixture is stirred from 0° C. to room temperature for 2 hours, then heated to 65° C. for 2 hours. The reaction medium is cooled to room temperature and poured drop-by-drop into diisopropylether (1.8 L) while being stirred. The white precipitate is recovered by filtration, washed two times with diisopropylether, then dried under vacuum at 30° C. in order to obtain a white solid.
Co-Polyamino Acid B14

Co-polyamino acid B14-1 is solubilized in DMAc (250 mL) then Pd/Al$_2$O$_3$ (5.0 g) is added under an argon atmosphere. The mixture is placed under a hydrogen atmosphere (10 bar) and stirred at 60° C. for 24 hours. After cooling to room temperature and filtration of the catalyst on sintered P4, then filtration through an Omnipore 0.2 μm PTFE hydrophilic membrane, a solution of water at pH 2 (6 V) is run drop-by-drop on the DMAc solution, over a period of 45 minutes and while stirring. After 18 hours of stirring, the white precipitate is recovered by filtration, washed with water, then dried under reduced pressure. The solid obtained is solubilized in water (1.25 L) while adjusting the pH to 7 by adding a 1N aqueous soda solution. The pH is then adjusted to pH13 and the solution is stirred for 3 hours. After neutralization to pH 7, the solution is filtered through 0.2 μm, diluted with ethanol in order to obtain a solution containing 30% by mass of ethanol, then filtered with an activated carbon filter (3M R53SLP). The solution is filtered through a 0.45 μm filter, then purified by ultrafiltration against a 0.9% NaCl solution, until the conductimetry of the permeate is less than 50 S/cm. The co-polyamino acid solution is then concentrated and the pH is adjusted to 7. The aqueous solution is filtered through 0.2 μm and stored at 4° C.

Dry extract: 25.7 mg/g
DP (estimated by RMN ¹H)=24 therefore i=0.042
The average calculated molar mass of co-polyamino acid B14 is 4720 g/mol.
Organic HPLC-SEC (PEG calibrating): Mn=3300 g/mol.
Co-Polyamino Acid B15: Sodium Poly-L-Glutamate Modified by Molecule A13 for which the Esters are Deprotected and Having a Number-Average Molar Mass (Mn) of 4400 g/Mol Using a process similar to that used for the preparation of co-polyamino acid B3 applied to a hydrochloride salt of molecule A13 (3.39 g, 2.34 mmol) and to co-polyamino acid B2-1 (2.04 g), with a saponification step at pH 13 for 5 hours in a mixture containing 30% by mass of ethanol, a sodium poly-L-glutamate modified by molecule A13 for which the esters are deprotected is obtained.

Dry extract: 15.7 mg/g
DP (estimated according to RMN ¹H): 40
According to RMN ¹H: i=0.15
The average calculated molar mass of co-polyamino acid B15 is 12207 g/mol.
Organic HPLC-SEC (PEG calibrating): Mn=4400 g/mol.
Co-Polyamino Acid B17: Sodium Poly-L-Glutamate Modified at One of its Extremities by Molecule A15 for which the Esters are Deprotected and Having a Number-Average Molar Mass (Mn) of 1000 g/Mol Using a process similar to that used for the preparation of co-polyamino acid B14 applied to molecule A15 (10.85 g, 8.74 mmol) and to γ-benzyl-L-glutamate N-carboxyanhydride (23.00 g, 87.37 g), with a saponification step to pH 12 for 2 hours, a sodium poly-L-glutamate modified at one of its extremities by molecule A15, for which the esters are deprotected is obtained.

Dry extract: 23.9 mg/g
DP (estimated according to RMN ¹H): 10
According to RMN ¹H: i=0.1
The average calculated molar mass of co-polyamino acid B17 is 2576 g/mol.
Aqueous HPLC-SEC (PEG calibrating): Mn=1000 g/mol.
Co-Polyamino Acid B18: Sodium Poly-L-Glutamate Modified by Molecule A16 for which the Esters are Deprotected and Having a Number-Average Molar Mass (Mn) of 5000 g/Mol Using coupling similar to that used for the preparation of co-polyamino acid B3 applied to molecule A16 (31.06 g, 42.08 mmol) and to co-polyamine acid B2-1 (36.80 g), a beige solid id obtained after the acid precipitation step. This solid is diluted in TFA (100 g/L) and the mixture is stirred at room temperature for 3 hours. The solution is then poured drop-by-drop over water (3V) while stirring. After 16 hours of stirring, the precipitate is recovered by filtration, then washed with water. The solid obtained is solubilized in water while adjusting the pH to 7 by adding a 10 N aqueous soda solution. Once solubilization is complete, the pH is adjusted to pH 12 over 1 hour by adding a 1N solution of NaOH. After neutralization to pH7 by adding a solution of 1N HCl, the product is purified by a process similar to that used for the preparation of co-polyamino acid B3 (carbon filtration and ultrafiltration). A sodium poly-L-glutamate modified by molecule A16 for which the esters are deprotected is obtained.

Dry extract: 28.2 mg/g
DP (estimated according to RMN $^1$H): 40
According to RMN $^1$H: i=0.15

The average calculated molar mass of co-polyamino acid B18 is 9884 g/mol.

Organic HPLC-SEC (PEG calibrating): Mn=5000 g/mol.
Co-Polyamino Acid B19: Sodium Poly-L-Glutamate Modified by Molecule A17 for which the Esters are Deprotected and Having a Number-Average Molar Mass (Mn) of 4900 g/Mol Using a process similar to that used for the preparation of co-polyamino acid B3 applied to a hydrochloride salt of molecule A17 (7.35 g, 13.09 mmol) and to co-polyamino acid B2-1 (11.45 g), with a saponification step at pH 13 for 3 hours in a mixture containing 30% by mass of ethanol, a sodium poly-L-glutamate modified by molecule A17 for which the esters are deprotected is obtained.

Dry extract: 25.7 mg/g
DP (estimated according to RMN $^1$H): 40
According to RMN $^1$H: i=0.15

The average calculated molar mass of co-polyamino acid B19 is 9062 g/mol.

Organic HPLC-SEC (PEG calibrating): Mn=4900 g/mol.
Co-Polyamino Acid B20: Sodium Poly-L-Glutamate Modified by Molecule A18 for which the Esters are Deprotected and Having a Number-Average Molar Mass (Mn) of 5800 g/Mol Using a process similar to that used for the preparation of co-polyamino acid B3 applied to a hydrochloride salt of molecule A18 (5.43 g, 6.86 mmol) and to co-polyamino acid B2-1 (6.00 g), with a saponification step at pH 13 for 3 hours in a mixture containing 30% by mass of ethanol, a sodium poly-L-glutamate modified by molecule A18 for which the esters are deprotected is obtained.

Dry extract: 22.0 mg/g
DP (estimated according to RMN $^1$H): 40
According to RMN $^1$H: i=0.15

The average calculated molar mass of Co-polyamino acid B20 is 10444 g/mol.

Organic HPLC-SEC (PEG calibrating): Mn=5800 g/mol.
Co-Polyamino Acid B21: Sodium Poly-L-Glutamate Modified by Molecule A19 for which the Esters are Deprotected and Having a Number-Average Molar Mass (Mn) of 5000 g/Mol Using a process similar to that used for the preparation of co-polyamino acid B18 applied to molecule A19 (32.64 g, 45.97 mmol) and to co-polyamino acid B2-1 (40.20 g), a sodium poly-L-glutamate modified by molecule A19 for which the esters are saponified is obtained.

Dry extract: 26.2 mg/g
DP (estimated according to RMN $^1$H): 40
According to RMN $^1$H: i=0.15

The average calculated molar mass of Co-polyamino acid B21 is 9716 g/mol.

Organic HPLC-SEC (PEG calibrating): Mn=5000 g/mol.
Co-Polyamino Acid B22: Sodium Poly-L-Glutamate Modified at One of its Extremities by Molecule A20 and Having a Number-Average Molar Mass (Mn) of 1900 g/Mol Using a process similar to that used for the preparation of co-polyamino acid B14 applied to molecule A20 (13.28 g, 12.51 mmol) in CHCl$_3$ (53 mL) and to γ-benzyl-L-glutamate N-carboxyanhydride (72.46 g, 275.2 mmol), in DMF (270 mL), with a saponification step at pH 12 for 1 hour 30 minutes, a sodium poly-L-glutamate modified at one of its extremities by molecule A20, is obtained.

Dry extract: 27.3 mg/g
DP (estimated according to RMN $^1$H): 20
According to RMN $^1$H: i=0.05

The average calculated molar mass of co-polyamino acid B22 is 4087 g/mol.

Aqueous HPLC-SEC (PEG calibrating): Mn=1900 g/mol.
ii) Co-Polyamino Acids According to Formula XXXb

| No. | CO-POLYAMINO ACIDS BEARING CARBOXYLATE CHARGES AND HYDROPHOBIC RADICALS |
|-----|---|
| B7' | 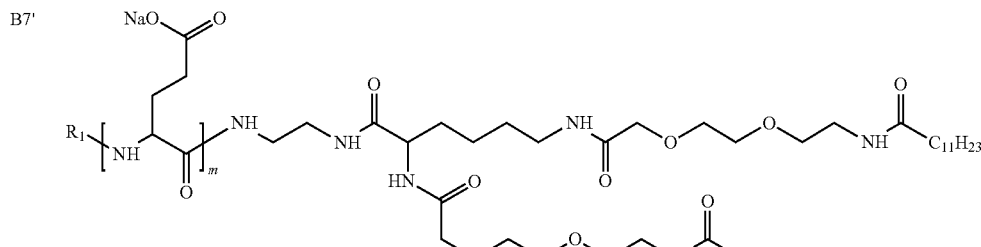 | i = 0.042, DP (m) = 24
R$_1$ = H or pyroglutamate

-continued
| No. | CO-POLYAMINO ACIDS BEARING CARBOXYLATE CHARGES AND HYDROPHOBIC RADICALS |
|---|---|
| B8 | 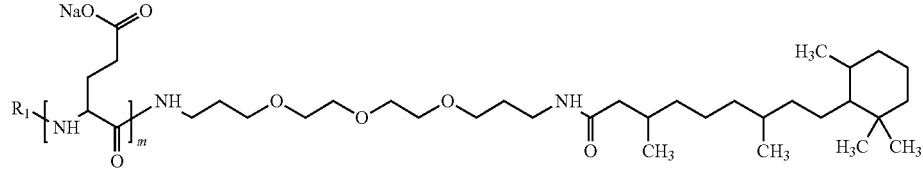<br>$i = 0.043$, DP (m) = 23<br>$R_1$ = H or pyroglutamate |
| B10 | 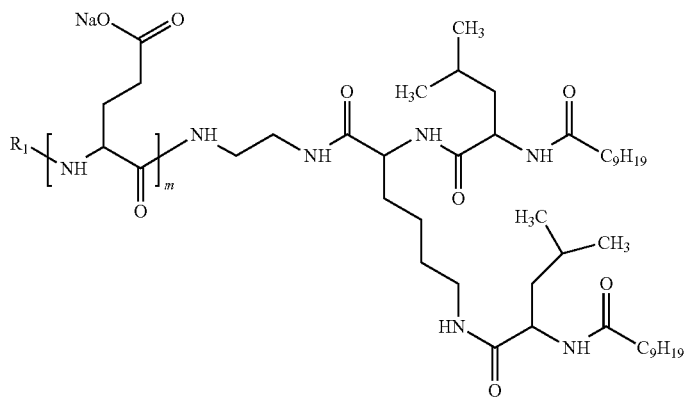<br>$i = 0.032$, DP (m) = 31<br>$R_1$ = H or pyroglutamate |
| B11 | 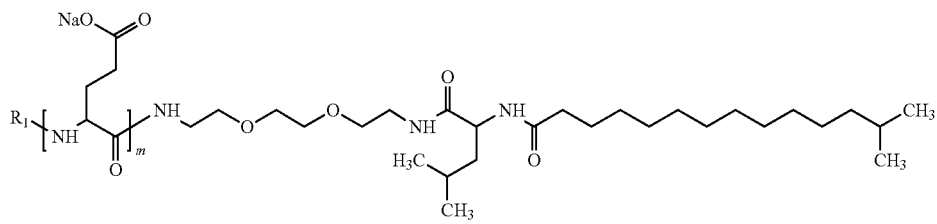<br>$i = 0.034$, DP (m) = 29<br>$R_1$ = H or pyroglutamate |

| No. | CO-POLYAMINO ACIDS BEARING CARBOXYLATE CHARGES AND HYDROPHOBIC RADICALS |
|---|---|
| B12 | 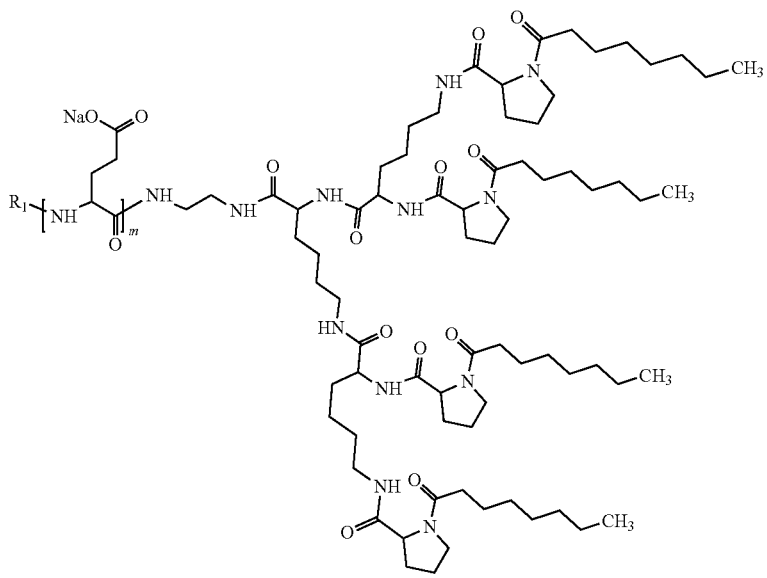 i = 0.042, DP (m) = 24<br>$R_1$ = H or pyroglutamate |

Co-Polyamino Acid B7': Sodium Poly-L-Glutamate Modified at One of its Extremities by Molecule A5a and Having a Number-Average Molar Mass (Mn) of 2600 g/Mol Co-Polyamino Acid B7'-1: Poly-L-Benzylglutamate Modified at One of its Extremities by Molecule A5a.

In a previously oven-dried flask, γ-benzyl-L-glutamate N-carboxyanhydride (10.1 g, 38.4 mmol) is solubilized in anhydrous DMF (19 mL). The mixture then stirred until completely dissolved, cooled to 0° C., then a solution of molecule A5a (1.47 g, 1.74 mmol) in chloroform (3.7 mL) is quickly introduced. The mixture is stirred from 0° C. to room temperature for 2 hours, then heated to 65° C. for 2 hours. The reaction medium is cooled to room temperature and poured drop-by-drop into diisopropylether (0.29 L) while being stirred. The white precipitate is recovered by filtration, washed two times with diisopropylether (5×50 mL), then dried under vacuum at 30° C. in order to obtain a white solid.

Co-Polyamino Acid B7'

Co-polyamino acid B7'-1 (8.33 g, 33.0 mmol) is diluted in trifuloroacetic (TFA, 132 mL), then the solution is cooled to 4° C. A 33% HBr solution in acetic acid (92.5 mL, 0.528 mol) is then added drop-by-drop. The mixture is stirred at room temperature for 2 hours, then poured drop-by-drop over a 1:1 mixture (v/v) of diisopropylether and water while stirring (0.8 L). After stirring for 2 hours, the heterogeneous mixture is allowed to rest overnight. The white precipitate is recovered by filtration, washed with IPE (2×66 mL) then with water (2×66 mL). The solid obtained is then solubilized in water (690 mL) while adjusting the pH to 7 by adding a 1 N aqueous soda solution. After solubilization, the theoretical concentration is adjusted to theoretical 20 g/L by adding water (310 mL), the solution is filtered through a 0.45 μm filter, then purified by ultrafiltration against a solution of NaCl 0.9%, then water until the conductimetry of the permeate is less than 50 μS/cm. The solution obtained is filtered through 0.2 μm and stored at 2-8° C.

Dry extract: 17.3 mg/g
DP (estimated according to RMN $^1$H): 24
According to RMN $^1$H: i=0.042
The average calculated molar mass of co-polyamino acid B7 is 4430 g/mol.
Organic HPLC-SEC (PEG calibrating): Mn=2600 g/mol.

Example B8: Co-Polyamino Acid B8—Sodium Poly-L-Glutamate Modified at One of Its Extremities by Molecule A6A and Having a Number-Average Molar Mass (Mn) of 2400 g/Mol Co-Polyamino Acid B8-1: Poly-L-Benzylglutamate Modified at One of its Extremities by Molecule A6.

In a previously oven-dried flask, γ-benzyl-L-glutamate N-carboxyanhydride (19.0 g, 72.2 mmol) is solubilized in anhydrous DMF (19 mL). The mixture then stirred until completely dissolved, cooled to 0° C., then a solution of molecule A6a (1.68 g, 3.28 mmol) in chloroform (3.7 mL) is quickly introduced. The mixture is stirred from 0° C. to room temperature for 2 hours, then heated to 65° C. for 2 hours. The reaction medium is cooled to room temperature and poured drop-by-drop into diisopropylether (0.29 L) while being stirred. The white precipitate is recovered by filtration, washed two times with diisopropylether (5×50 mL), then dried under vacuum at 30° C. in order to obtain a white solid.

Co-Polyamino Acid B8

Using a process similar to that used for the preparation of co-polyamino acid B7' applied to co-polyamino acid B8-1 (14.6 g, 61.5 mmol), a sodium poly-L-glutamate modified at one of its extremities by molecule A6a is obtained.

Dry extract: 21.3 mg/g
DP (estimated according to RMN $^1$H): 23
According to RMN $^1$H: i=0.043
The average calculated molar mass of Co-polyamino acid B8 is 3948 g/mol.

Organic HPLC-SEC (PEG calibrating): Mn=2400 g/mol.
Co-Polyamino Acid B10: Sodium Poly-L-Glutamate Modified at One of its Extremities by Molecule A8 and Having a Number-Average Molar Mass (Mn) of 3100 g/Mol Co-polyamino acid B10-1: poly-L-benzylglutamate modified at one of its extremities by molecule A8.

In an appropriate container are successively introduced, the hydrochloride salt of molecule A8 (2.308 g, 3.04 mmol), chloroform (120 mL), molecular sieve 4 Å (1.5 g), as well as the ion exchange resin Amberlite IRN 150 (1.5 g). After stirring from 1 hour on rollers, the medium is filtered and the resin is rinsed with chloroform. The mixture is evaporated, then co-evaporated with toluene. The residue is solubilized in anhydrous DMF (40 mL) in order to be used directly in the polymerization reaction.

In a previously oven-dried flask, γ-benzyl-L-glutamate N-carboxyanhydride (20.0 g, 76.0 mmol) is solubilized in anhydrous DMF (19 mL). The mixture then stirred until completely dissolved, cooled to 0° C., then a solution of molecule A8, previously prepared, in chloroform (3.7 mL) is quickly introduced. The mixture is stirred from 0° C. to room temperature for 2 hours, then heated to 65° C. for 2 hours. The reaction medium is cooled to room temperature and poured drop-by-drop into diisopropylether (0.29 L) while being stirred. The white precipitate is recovered by filtration, washed two times with diisopropylether (5×50 mL), then dried under vacuum at 30° C. in order to obtain a white solid.

Co-Polyamino Acid B10

Using a process similar to that used for the preparation of co-polyamino acid B7' applied to co-polyamino acid B10-1 (15.2 g, 60.8 mmol), a sodium poly-L-glutamate modified at one of its extremities by molecule A8 is obtained.

Dry extract: 34.1 mg/g
DP (estimated according to RMN $^1$H): 31
According to RMN $^1$H: i=0.032
The average calculated molar mass of co-polyamino acid B10 is 5367 g/mol.
Organic HPLC-SEC (PEG calibrating): Mn=3100 g/mol.

Example B11: Co-Polyamino Acid B11—Sodium Poly-L-Glutamate Modified at One of Its Extremities by Molecule A9 and Having a Number-Average Molar Mass (Mn) OF 3000 g/Mol Co-Polyamino Acid B11-1: Poly-L-Benzylglutamate Modified at One of its Extremities by Molecule A9.

In an appropriate container are successively introduced the hydrochloride salt of molecule A9 (2.023 g, 3.87 mmol), chloroform (120 mL), molecular sieve 4 Å (1.5 g), as well as the ion exchange resin Amberlite IRN 150 (1.5 g). After stirring from 1 hour on rollers, the medium is filtered and the resin is rinsed with chloroform. The mixture is evaporated, then co-evaporated with toluene. The residue is solubilized in anhydrous DMF (40 mL) in order to be used directly in the polymerization reaction.

Using a process similar to that used for the preparation of co-polyamino acid B8-1 applied to the solution of molecule A9 prepared previously and to γ-benzyl-L-glutamate N-carboxyanhydride (25.5 g, 96.8 mmol), the co-polyamino acid B11-1 is obtained.

Co-Polyamino Acid B11

Using a process similar to that used for the preparation of co-polyamino acid B7' applied to co-polyamino acid B11-1 (18.4 g, 77.3 mmol), a sodium poly-L-glutamate modified at one of its extremities by molecule A9 is obtained.

Dry extract: 28.0 mg/g
DP (estimated according to RMN $^1$H): 29
According to RMN $^1$H: i=0.034
The average calculated molar mass of co-polyamino acid B11 is 4828 g/mol.
Organic HPLC-SEC (PEG calibrating): Mn=3000 g/mol.

Co-Polyamino Acid B12: Sodium Poly-L-Glutamate Modified at One of its Extremities by Molecule A10 and Having a Number-Average Molar Mass (Mn) of 2700 g/Mol Co-polyamino acid B12-1: poly-L-benzylglutamate modified at one of its extremities by molecule A10.

Using a process similar to that used for the preparation of co-polyamino acid B10-1 applied to molecule A10 (3.0 g, 2.24 mmol) and to γ-benzyl-L-glutamate N-carboxyanhydride (12.99 g, 49.3 mmol), co-polyamino acid B12-1 is obtained.

Co-Polyamino Acid B12

Using a process similar to that used for the preparation of co-polyamino acid B7' applied to co-polyamino acid B12-1 (13.2 g, 48.0 mmol), a sodium poly-L-glutamate modified at one of its extremities by molecule A10 is obtained.

Dry extract: 13.2 mg/g
DP (estimated according to RMN $^1$H): 24
According to RMN $^1$H: i=0.042
The average calculated molar mass of co-polyamino acid B12 is 4924 g/mol.
Organic HPLC-SEC (PEG calibrating): Mn=2700 g/mol.

Part C: Compositions

The glucagon used is human glucagon resulting from a peptide synthesis process. It comes from Bachem (reference 4074733).

Example C1: Solution of Glucagon at 2 Mg/Ml 94.7 mg of glucagon DS in powder is introduced into a 50 mL Falcon tube, followed by 45 mL of a hydrochloride solution at 0.003 N containing 2 mg/mL of L-methionine. The glucagon powder is mixed by repeated inversions of the tube until the glucagon is completely dissolved. The 2 mg/mL glucagon solution is then membrane (0.22 m) filtered.

Example C2: Solution of Glucagon at 4 Mg/Ml

Glucagon (160 mg) in powder is introduced into a 45 ml falcon tube, then 40 mL of the aqueous hydrochloric acid solution at 0.006 N containing 2 mg/mL of L-methionine is added. The glucagon powder is mixed by repeated inversions of the tube until the glucagon is completely dissolved. The 4 mg/ml glucagon solution is then membrane (0.22 μm) filtered.

Example CA0: Preparation of a Solution af Glucagon at 1 Mg/Ml Containing Different Co-Polyamino Acids of the Invention, A Phosphate Buffer (2 Mm) and Glycerin at pH 7.2

A co-polyamino acid solution is added into a flask containing concentrated solutions of excipients (phosphate, glycerol (in order to obtain 300 mOsmole/kg in the final formulation) and potentially additives (m-cresol, citrate). The composition is stirred briefly until the co-polyamino acid is dissolved, then the solution is filtered through membrane (0.22 The equivolumic mixture of this solution with the freshly prepared glucagon solution, as described in example C1, results in final compositions CA1 to CA32 and CA15' and CA26' containing 1 mg/mL of glucagon. The pH of the solution is adjusted to pH 7.2±0.1 by adding a 1 N NaOH/HCl then filtered through a membrane (0.22 μm). The details of the compositions is summarized in the tables below.

A visual inspection is carried out in order to determine if a clear solution has been obtained (by comparison, the glucagon solution at neutral pH is not soluble above 0.2 mg/mL). A visual inspection of the samples is performed in order to detect visible particles or turbidity. This inspection is carried out according to the recommendations of European Pharmacopoeia (EP 2.9.20): the samples are subjected to lighting of at least 2000 Lux and are observed in front of a white background and of a black background. When particles are visible in half the samples, the composition is considered not clear.

The results are shown in Tables 1 and 1a: Compositions and visual aspect of glucagon solutions at 1 mg/mL at pH 7.2 at different concentrations of co-polyamino acid containing 2 mM of phosphate buffer and 1 mg/mL of L-methionine.

TABLE 1

Compositions and visual aspect of solutions of glucagon at 1 mg/mL at pH 7.2 at different concentrations of co-polyamino acid containing 2 mM of phosphate buffer and 1 mg/mL of L-methionine.

| Compositions | Co-polyamino acid | Concentrations in co-polyamino acid (mg/mL) | Co-polyamino acid/glucagon molar ratio | Additives | Glycerol (mM) | Visual aspect of the solution |
|---|---|---|---|---|---|---|
| CA1 | B3 | 3.43 | 1.33 | | 290 | Clear |
| CA2 | | 4.02 | 1.56 | | 290 | Clear |
| CA3 | | 3.61 | 1.4 | 10 mM citrate | 250 | Clear |
| CA4 | | 4.13 | 1.6 | 10 mM citrate | 250 | Clear |
| CA5 | B2 | 6.95 | 2.6 | 10 mM citrate | 250 | Clear |
| CA6 | | 7.75 | 2.9 | 10 mM citrate | 250 | Clear |
| CA7 | | 7.75 | 2.9 | | 294 | Clear |
| CA8 | | 8.55 | 3.2 | | 294 | Clear |
| CA9 | | 9.62 | 3.6 | | 294 | Clear |
| CA10 | B1 | 4.3 | 3 | 27 mM-cresol | 259 | Clear |
| CA11 | | 7.2 | 5 | 27 mM-cresol | 253 | Clear |
| CA11C | | 2.61 | 2 | 10 mM citrate | 260 | Clear |
| CA11D | | 2.87 | 2.2 | 10 mM citrate | 260 | Clear |
| CA11E | | 4.95 | 3.8 | 10 mM citrate | 260 | Clear |
| CA11F | | 2.61 | 2 | | 290 | Clear |
| CA11G | | 2.87 | 2.2 | | 290 | Clear |
| CA12 | B3 | 2.58 | 1 | | 290 | Clear |
| CA13 | | 3.09 | 1.2 | | 290 | Clear |
| CA14 | | 2.58 | 1 | 10 mM citrate | 260 | Clear |
| CA15 | | 3.09 | 1.2 | 10 mM citrate | 260 | Clear |
| CA16 | B2 | 2.67 | 1 | 10 mM citrate | 260 | Clear |
| CA17 | | 3.20 | 1.2 | 10 mM citrate | 260 | Clear |
| CA18 | | 2.14 | 0.8 | | 300 | Clear |
| CA19 | | 2.67 | 1 | | 300 | Clear |
| CA20 | | 3.20 | 1.2 | | 300 | Clear |
| CA21 | B5 | 6.28 | 2.2 | 10 mM citrate | 260 | Clear |
| CA22 | | 7.13 | 2.5 | 10 mM citrate | 260 | Clear |
| CA23 | B20 | 4.27 | 1.5 | 10 mM citrate | 260 | Clear |
| CA24 | | 5.70 | 2.0 | 10 mM citrate | 260 | Clear |
| CA25 | B14 | 3.79 | 2.8 | 10 mM citrate | 248 | Clear |
| CA26 | | 4.06 | 3.0 | 10 mM citrate | 248 | Clear |
| CA27 | B19 | 3.12 | 1.2 | 10 mM citrate | 249 | Clear |
| CA28 | | 3.64 | 1.4 | 10 mM citrate | 249 | Clear |
| CA29 | B17 | 2.22 | 3.2 | 10 mM citrate | 249 | Clear |
| CA30 | | 2.37 | 3.0 | 10 mM citrate | 249 | Clear |

TABLE 1-continued

Compositions and visual aspect of solutions of glucagon at 1 mg/mL at pH 7.2 at different concentrations of co-polyamino acid containing 2 mM of phosphate buffer and 1 mg/mL of L-methionine.

| Compositions | Co-polyamino acid | Concentrations in co-polyamino acid (mg/mL) | Co-polyamino acid/glucagon molar ratio | Additives | Glycerol (mM) | Visual aspect of the solution |
|---|---|---|---|---|---|---|
| CA31 | B18 | 3.46 | 1.2 | 10 mM citrate | 260 | Clear |
| CA32 |  | 4.03 | 1.4 | 10 mM citrate | 260 | Clear |

TABLE 1a

Compositions and visual aspect of solutions of glucagon at 1 mg/mL at pH 7.2 at different concentrations of co-polyamino acid containing phosphate buffer (2 mM) and 1 mg/mL of L-methionine.

| Composition | Co-polyamino acid | Concentration of co-polyamino acid (mg/mL) | Co-polyamino acid/ Glucagon ratio | Additives | Glycerin (mM) | Visual aspect of the solution |
|---|---|---|---|---|---|---|
| CA15' | B11 | 20.2 | 14.6 | 23 mM-cresol | 230 | Clear |
| CA26' | B8 | 2.50 | 2.2 |  | 292 | Clear |

The above prepared compositions are clear, while the glucagon prepared under these conditions, without co-polyamino acid, is not soluble.

Example CB0: Preparation of a Solution of Co-Polyamino Acid and Glucagon at 2 Mg/Ml at pH 7.2

In a similar protocol to that of example CA0, glucagon compositions at 2 mg/mL containing different co-polyamino acids, glycerol (in order to obtain 300 mOsmol/kg in the final formulation), a phosphate buffer (2 mM) and additives are prepared. They are presented in table 1b below:

TABLE 1b

Compositions and visual aspect of glucagon solutions at 2 mg/mL at pH 7.2 at different concentrations of co-polyamino acid containing 2 mM of phosphate buffer and 1 mg/mL of L-methionine.

| Composition | co-polyamino acid | Concentration of co-polyamino acids (mg/mL) | Co-polyamino acid/Glucagon ratio | Additive | glycerol (mM) | Visual aspect of the solution |
|---|---|---|---|---|---|---|
| CB1 | B3 | 6.9 | 1.33 |  | 290 | Clear |
| CB2 |  | 10.3 | 2 | 10 mM citrate | 250 | Clear |
| CB3 | B2 | 16 | 3 | 10 mM citrate | 250 | Clear |
| CB4 |  | 16 | 3 |  | 294 | Clear |

Physical Stability of the Compositions

The compositions prepared above were transferred into cartridges (easy-to-fill from OMPI of 3 ml—Ref P40B4100.3250) at the rate of 1 mL per cartridge and placed in static conditions at 37° C.

Visual inspections of the samples placed in static conditions at 37° C. were performed at 0, 1, 2, 3, 4, 5, 6 weeks at 37° C. in order to detect the appearance of visible particles, fibrils or turbidity. This inspection is carried out according to the recommendations of European Pharmacopoeia (EP 2.9.20): the samples are subjected to lighting of at least 2000 Lux and are observed in front of a white background and of a black background, in order to comply with the recommendations of the European Pharmacopoeia. When particles are visible in half the samples, the composition is considered unstable. Therefore, stable, on the day of inspection, means that at least half of the samples had no particles, fibrils or turbidity.

The results of the visual inspections are recorded in the following table. The study of the physical stability of the compositions described in the table below was carried out on volumes of 1 mL of composition in cartridges with a capacity of 3 mL (OMPI—ref: P40B4100.3250). By comparison, the solution of glucagon at acidic pH at 1 mg/mL is stable for only 2 days at 37° C.

TABLE 2

Physical stability at 37° C. of compositions comprising B1, B2 or B3 in cartridge.

| Compositions | Co-polyamino acid | Concentrations in co-polyamino acid (mg/mL) | Additive | Stability (week) |
|---|---|---|---|---|
| CA2 | B3 | 4.02 |  | >2<br>>5 |
| CA3 |  | 3.61 | 10 mM citrate | >2<br>>4 |
| CA4 |  | 4.13 | 10 mM citrate | >2<br>>20 |

TABLE 2-continued

Physical stability at 37° C. of compositions comprising B1, B2 or B3 in cartridge.

| Compositions | Co-polyamino acid | Concentrations in co-polyamino acid (mg/mL) | Additive | Stability (week) |
|---|---|---|---|---|
| CA5 | B2 | 6.95 | 10 mM citrate | >2 |
| CA6 |  | 7.75 | 10 mM citrate | >2 |
| CA7 |  | 7.75 |  | >2 |
| CA8 |  | 8.55 |  | >2 |
| CA9 |  | 9.62 |  | >2 |
| CA11E | B1 | 3.8 | 10 mM citrate | >10 |

The composition CA11 was transferred to a 3 mL vial (Adelphi—ref: VCDIN2RDLS1) at a rate of 1 mL per vial and placed in static conditions at 37° C. The results of the visual inspections are recorded in the following table.

TABLE 3

Physical stability at 37° C. of composition B1 in vial.

| Compositions | Co-polyamino acid | Concentrations in co-polyamino acid (mg/mL) | Additive | Stability at 37° C. (week) |
|---|---|---|---|---|
| CA11 | B1 | 7.2 | 27 mM-cresol | >2 >6 |

Solutions according to the invention present a physical stability at 37° C. in static conditions in cartridge superior to two weeks at 37° C. The addition of co-polyamino acid B1 makes it possible to solubilize and stabilize the glucagon at neutral pH while the glucagon in solution at acidic pH is only stable for a few days at 37° C. (2 days).

Results of Visual Observations of the Mixture and of the Fibrillation Measurements.

The above-prepared compositions were aliquoted into a 96 well tray in triplicate (3*150 μL) and placed under static conditions at 37° C.

Principle

The poor stability of a peptide may lead to the formation of amyloid fibrils defined as ordered, macromolecular structures. These may possibly result in the formation of a gel within the sample.

The follow-up test of fluorescence of Thioflavin T (ThT) is used to analyze the physical stability of solutions. Thioflavin is a small probe molecule with a characteristic fluorescence signature when it bonds to amyloid type fibrils (Naiki et al. (1989) Anal. BioChem. 177, 244-249; LeVine (1999) Methods. Enzymol. 309, 274-284).

This method makes it possible to monitor the formation of fibrils for low concentrations of ThT within undiluted solutions. This monitoring is carried out under accelerated, stable conditions: while stirring and at 37° C.

Experimental Conditions

The samples are prepared just before the beginning of measurement. The preparation of each composition is described in the related example. Thioflavin T was added to the composition from a parent solution concentrated in order to induce negligible dilution of the composition. The concentration of Thioflavin T in the composition is 40 M.

A volume of 150 μL of the composition was introduced into one of the well of a 96 well tray, then 2.7 μL of concentrated solution of ThT was introduced. Each composition was analyzed using three tests (triplicate) in the same tray. The tray was sealed by a transparent film in order to prevent evaporation of the composition.

Each tray was then placed inside a tray reader (Xenius XC, SAFAS). The temperature was set at 37° C., and lateral stirring of 960 rpm with 1 mm of amplitude was started.

A reading of the intensity of fluorescence in each well was carried out with an excitation wave length of 442 nm, and an emission wave length of 482 nm, over time.

The fibrillation process is manifested by a strong increase in fluorescence after a period called the latency time.

The lag time is determined by graph, using the time at which the tangent of the linear growth phase crosses the abscissa axis.

The value of the recorded latency time corresponds to the average of measurements of latency time taken on three wells.

An example of a graphic determination is represented in FIG. 1.

This FIGURE graphically represents the determination of the latency time or "lag time" (LT) by fluorescent monitoring of Thioflavin T, on a curve with the value of the fluorescence on the ordinate axis (in u.a., arbitrary units) and the time in minutes on the abscissa.

The lag time results obtained are presented in the table below. By comparison, glucagon alone is insoluble in solution at physiological pH and the solution of glucagon at acidic pH at 1 mg/mL shows a fibrillation time of about 0.5 hours.

TABLE 4

Measurement of latency time of compositions CA11D to CA32.

| Compositions | Co-polyamino acid | Concentrations in co-polyamino acid (mg/mL) | Additive | Fibrillation time (h) |
|---|---|---|---|---|
| CA11D |  | 2.87 | 10 mM citrate | >10 |
| CA11G |  | 2.87 | — | 2 < t < 4 |
| CA12 | B3 | 2.58 | — | >60 |
| CA13 |  | 3.09 | — | >90 |
| CA14 |  | 2.58 | 10 mM citrate | >60* |
| CA15 |  | 3.09 | 10 mM citrate | >60* |
| CA16 | B2 | 2.67 | 10 mM citrate | >10* |
| CA17 |  | 3.20 | 10 mM citrate | >20 |
| CA18 |  | 2.14 | — | >9 |
| CA19 |  | 2.67 | — | >10 |
| CA20 |  | 3.20 | — | >10 |
| CA21 | B5 | 6.28 | 10 mM citrate | >50 |
| CA22 |  | 7.13 | 10 mM citrate | >70 |
| CA23 | B20 | 4.27 | 10 mM citrate | >60 |
| CA24 |  | 5.70 | 10 mM citrate | >70 |
| CA26 | B14 | 4.06 | 10 mM citrate | >10 |
| CA28 | B19 | 3.64 | 10 mM citrate | >15 |
| CA30 | B17 | 2.37 | 10 mM citrate | >15 |

TABLE 4-continued

Measurement of latency time of compositions CA11D to CA32.

| Compositions | Co-polyamino acid | Concentrations in co-polyamino acid (mg/mL) | Additive | Fibrillation time (h) |
|---|---|---|---|---|
| CA31 | B18 | 3.46 | 10 mM citrate | >10 |
| CA32 | | 4.03 | 10 mM citrate | >20 |

*The trials were halted before fibrillation.

Compositions containing co-polyamino acids make it possible to considerably increase the lag time in relation to the glucagon solution at acidic pH alone, which is stable for only a few minutes under these measurement conditions.

The invention claimed is:

1. A composition in the form of an injectable aqueous solution, for which the pH is comprised from 6.0 to 8.0, comprising at least:
   a) human glucagon;
   b) a co-polyamino acid bearing carboxylate charges and hydrophobic radicals Hy, said co-polyamino acid being constituted of glutamic or aspartic units and said hydrophobic radicals Hy chosen according to formula X as defined below:

$$*-(GpR)_r-(GpG)_g-(GpA)_a-[(GpL)_l-[(GpH)_h-GpC]_{l'}]_{a'} \quad \text{Formula X}$$

in which

GpR is chosen among the radicals according to formulas according to formulas VII, VII' or VII'':

$$*-\overset{H}{N}-R-\overset{H}{N}-* \quad \text{Formula VII}$$

or $$*-\overset{O}{\overset{\|}{C}}-R-\overset{H}{N}-* \quad \text{Formula VII'}$$

or $$*-\overset{O}{\overset{\|}{C}}-R-\overset{O}{\overset{\|}{C}}-* \quad \text{Formula VII''}$$

Identical or different GpG and GpH are chosen among the radicals according to formulas XI or XI';

$$*-\overset{O}{\overset{\|}{C}}-G-\overset{H}{N}-* \quad \text{Formula XI}$$

$$*-NH-G-NH-* \quad \text{Formula XI'}$$

GpA is chosen among the radicals according to formula VIII $$*-NH-A'-[NH-]_{s'}* \quad \text{Formula VIII}$$

In which A' is chosen among the radicals according to formulas VIII', VIII'' or VIII'''

$$\overset{A_1}{\underset{*}{\diagdown}}CO \qquad A_1-\overset{|}{\underset{*}{N}}-A_2 \qquad A_1-\overset{|}{\underset{*}{N}}-A_2-\overset{|}{\underset{*}{N}}-A_3$$

Formula VIII' or Formula VIII'' or Formula VIII'''

-GpL is chosen among the radicals according to formula XII $$*-\overset{O}{\overset{\|}{C}}-A\overset{HN-*}{\diagdown}_{HN-*} \quad \text{Formula XII}$$

GpC is a radical according to formula IX:

Formula IX

* indicate the attachment sites of the different groups bound by amide functions;

a is an integer equal to 0 or to 1 and a'=1 if a=0 and a'=1, 2 or 3 if a=1;

a' is an integer equal to 1, to 2 or to 3;

b is an integer equal to 0 or to 1;

c is an integer equal to 0 or to 1, and if c is equal to 0, then d is equal to 1 or to 2;

d is an integer equal to 0, to 1 or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6;

l is an integer equal to 0 or to 1 and l'=1 if l=0 and l'=2 if l=1;

r is an integer equal to 0, 1 or to 2;

s' is an integer equal to 0 or to 1;

And if e is different from 0, then at least one of g, h or l is different from 0;

And if a=0, then l=0;

A, $A_1$, $A_2$ and $A_3$ identical or different, are linear or branched alkyl radicals comprising from 1 to 8 carbon atoms and/or, substituted by a radical from a saturated, unsaturated or aromatic ring;

B is a radical ether or polyether, unsubstituted, comprising from 4 to 14 carbon atoms and from 1 to 5 oxygen atoms, or a linear or branched alkyl radical, and/or comprising an aromatic ring, comprising from 1 to 9 carbon atoms;

$C_x$ is a linear or branched, monovalent alkyl radical and/or comprising a cyclic part, in which x indicates the number of carbon atoms, and:

When the hydrophobic radical -Hy bears 1 -GpC, then $9 \leq x \leq 25$,

When the hydrophobic radical -Hy bears 2 -GpC, then $9 \leq x \leq 15$,

When the hydrophobic radical -Hy bears 3 -GpC, then $7 \leq x \leq 13$,

When the hydrophobic radical -Hy bears 4 -GpC, then $7 \leq x \leq 11$,

When the hydrophobic radical -Hy bears at least 5 -GpC; $6 \leq x \leq 11$;

G is a branched alkyl radical of 1 to 8 carbon atoms, said alkyl radical bears one or more free carboxylic acid functions, R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and from 1 to 5 oxygen atoms, the hydrophobic radical(s) -Hy according to formula X being bound to the PLG:

via a covalent bond between a carbonyl of hydrophobic radical -Hy and a nitrogen atom borne by the PLG, thus forming an amide function resulting from the reaction of an amine function borne by the PLG and an acid function borne by the precursor Hy' of the hydrophobic radical -Hy, and via a covalent bond between a nitrogen atom of the hydrophobic radical -Hy and a carbonyl borne by the PLG; thus forming an amide function resulting from the reaction of an amine function of the precursor -Hy' of the hydrophobic radical -Hy and an acid function borne by the PLG, The ratio M between the number of hydrophobic radicals and the number of glutamic or aspartic unites being between $0 < M \leq 0.5$;

when several hydrophobic radicals are borne by a co-polyamino acid, then they are identical or different, The degree of polymerization DP in glutamic or aspartic units for the PLG chains is comprised from 5 to 250;

Free carboxylic acids being in the form of an alkaline cation salt chosen from the group consisting of $Na^+$ and $K^+$.

2. The composition according to claim 1, wherein the co-polyamino acid bearing carboxylate charges and hydrophobic radicals is chosen among the co-polyamino acids according to formula XXX below:

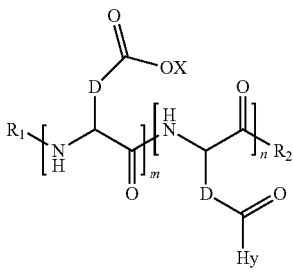

Formula XXX in which,

D represents, independently, either a —$CH_2$— group (aspartic unit) of a —$CH_2$—$CH_2$— group (glutamic unit), Hy is a hydrophobic radical chosen among the hydrophobic radicals according to formula X, in which r=1 and GpR is a radical according to formula VII, $R_1$ is a hydrophobic radical chosen among the hydrophobic radicals according to formula X in which r=0 or r=1 and GpR is a radical according to formula VII', or a radical chosen from the group consisting of an H, a linear acyl group in C2 to C10, a branched acyl group in C3 to C10, a benzyl, an end "amino acid" unit and a pyroglutamate, $R_2$ is a hydrophobic radical chosen among the hydrophobic radicals according to formula X in which r=1 and GpR is a radical according to formula VII or an —NR'R", R' and R" radical, identical or different, being chosen from the group consisting of H, the linear, branched or cyclic alkyls in C2 to C10, benzyl and said R' and R" alkyls being able to together form one or more saturated, unsaturated and/or aromatic rings and/or being able to comprise heteroatoms, chosen from the group consisting of O, N and S, X represents a H or a cationic entity chosen from the group comprising the metallic cations;

n+m represents the degree of polymerization DP of the co-polyamino acid, that is the average number of monomeric units per co-polyamino acid chain and $5 \leq n+m \leq 250$.

3. The composition according to claim 2, wherein the co-polyamino acid bearing carboxylate charges and hydrophobic radicals is chosen among the co-polyamino acids according to formula XXX, in which n=0 according to formula XXXb below:

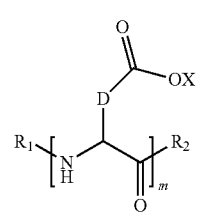

Formula XXXb in which m, X, D, $R_1$ and $R_2$ have the definitions given above and at least $R_1$ or $R_2$ is a hydrophobic radical according to formula X.

4. The composition according to claim 3, wherein the co-polyamino acid bearing carboxylate charges and hydrophobic radicals is chosen among the co-polyamino acids according to formula XXXb, in which $R_2$ is a hydrophobic radical according to formula X in which r=1 and GpR is according to formula VII'.

5. The composition according to claim 1, wherein the co-polyamino acid bearing carboxylate charges and hydrophobic radicals is chosen among the co-polyamino acids according to formula XXX, XXXb, XXXa:

Formula XXX

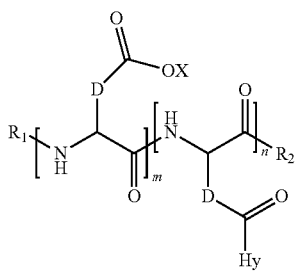

Formula XXXb

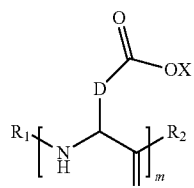

Formula XXXa

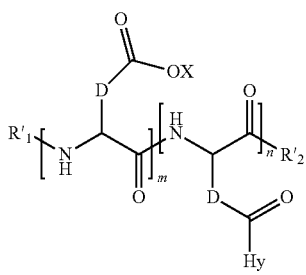

in which at least one co-polyamino acid is chosen among the co-polyamino acids in which the D group is a —CH$_2$— group (aspartic unit).

6. The composition according to claim 1, wherein the co-polyamino acid bearing carboxylate charges and hydrophobic radicals is chosen among the co-polyamino acids according to formula XXX, XXXb, XXXa:

Formula XXX

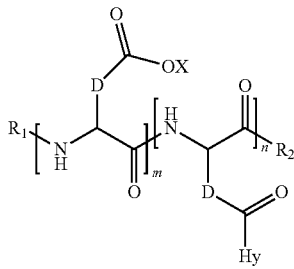

Formula XXXb

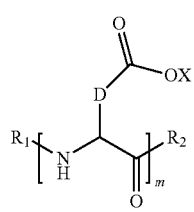

Formula XXXa

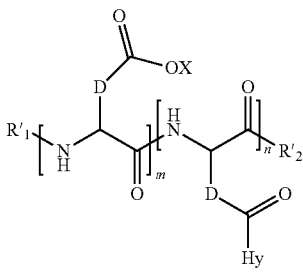

in which at least one co-polyamino acid is chosen among the co-polyamino acids in which the D group is a —CH$_2$—CH$_2$— group (glutamic unit).

7. The composition according to claim 1, wherein the concentration of co-polyamino acid bearing carboxylate charges and hydrophobic radicals is at most of 40 mg/mL.

8. The composition according to claim 1, wherein the concentration of human glucagon is comprised from 0.25 to 5 mg/mL.

9. The composition according to claim 1, wherein the [hydrophobic radical]/[human glucagon] molar ratio is greater than or equal to 15.

10. The composition according to claim 1, wherein it also comprises a polyanionic compound.

11. The composition according to claim 1, wherein it also comprises a zinc salt.

12. The composition according to claim 1, wherein it also comprises a gastro-intestinal hormone.

13. The composition according to claim 12, wherein the gastro-intestinal hormone is chosen from the group consisting of exanatide, liraglutide, lixisenatide, albiglutide and dulaglutide, their analogues or derivatives and their pharmaceutically acceptable salts.

14. The composition according to claim 12, wherein the concentration of gastro-intestinal hormone is comprised in an interval from 0.01 to 10 mg/mL, Co-polyamino acid bearing carboxylate charges and hydrophobic radicals Hy, chosen among the radicals according to formula X as defined below:

Formula X

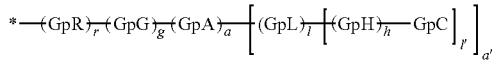

in which
GpR is chosen among the radicals according to formulas VII, VII' or VII":

Formula VII

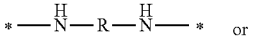 or

Formula VII'

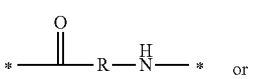 or

Formula VII"

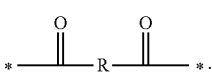 ;

Identical or different GpG and GpH are chosen among the radicals according to formulas XI or XI';

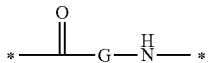

Formula XI

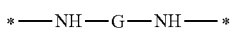

Formula XI'

GpA is chosen among the radicals according to formulas VIII

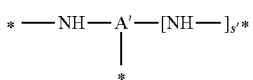

Formula VIII

In which A' is chosen among the radicals according to formulas VIII', VIII" or VIII'"

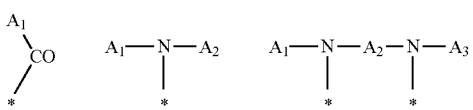

Formula VIII' or Formula VIII" or Formula VIII'"
GpL is chosen among the radicals according to formula XII

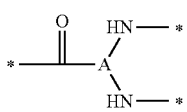

Formula XII

GpC is a radical according to formula IX:

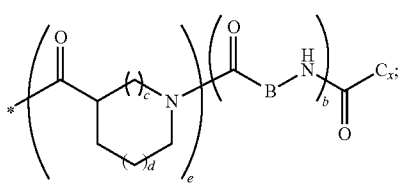

Formula IX

* indicate the attachment sites of the different groups bound by amide functions;
a is an integer equal to 0 or to 1 and a'=1 if a=0 and a'=1, 2 or 3 if a=1;
a' is an integer equal to 1, to 2 or to 3;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6;
l is an integer equal to 0 or to 1 and l'=1 if l=0 and l'=2 if l=1;
r is an integer equal to 0, 1 or to 2;
s' is an integer equal to 0 or to 1;
And if e is different from 0, then at least one of g, h or l is different from 0;
And if a=0, then l=0;
A, $A_1$, $A_2$ and $A_3$ identical or different, are linear or branched alkyl radicals comprising from 1 to 8 carbon atoms and/or, substituted by a radical from a saturated, unsaturated or aromatic ring;
B is a radical ether or polyether, unsubstituted, comprising from 4 to 14 carbon atoms and from 1 to 5 oxygen atoms, or a linear or branched alkyl radical, and/or comprising an aromatic ring, comprising from 1 to 9 carbon atoms;
$C_x$ is a linear or branched, monovalent alkyl radical and/or comprising a cyclic part, in which x indicates the number of carbon atoms, and:
When the hydrophobic radical -Hy bears 1 -GpC, then $9 \leq x \leq 25$,
When the hydrophobic radical -Hy bears 2 -GpC, then $9 \leq x \leq 15$,
When the hydrophobic radical -Hy bears 3 -GpC, then $7 \leq x \leq 13$,
When the hydrophobic radical -Hy bears 4 -GpC, then $7 \leq x \leq 11$,
When the hydrophobic radical -Hy bears at least 5 -GpC; $6 \leq x \leq 11$;
G is a branched alkyl radical of 1 to 8 carbon atoms, said alkyl radical bears one or more free carboxylic acid functions,
R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and from 1 to 5 oxygen atoms,
the hydrophobic radical(s) -Hy according to formula X being bound to the PLG:
via a covalent bond between a carbonyl of hydrophobic radical -Hy and a nitrogen atom borne by the PLG, thus forming an amide function resulting from the reaction of an amine function borne by the PLG and an acid function borne by the precursor Hy' of the hydrophobic radical -Hy, and
via a covalent bond between a nitrogen atom of the hydrophobic radical -Hy and a carbonyl borne by the PLG; thus forming an amide function resulting from the reaction of an amine function of the precursor -Hy' of the hydrophobic radical -Hy and an acid function borne by the PLG,
The ratio M between the number of hydrophobic radicals and the number of glutamic or aspartic unites being between $0<M \leq 0.5$;
when several hydrophobic radicals are borne by a co-polyamino acid, then they are identical or different,
The degree of polymerization DP in glutamic or aspartic units for the PLG chains is comprised from 5 to 250;
Free carboxylic acids being in the form of an alkaline cation salt chosen from the group consisting of $Na^+$ and $K^+$.
15. A hydrophobic radical precursor Hy' of the hydrophobic radical-Hy according to formula X':

Formula X'

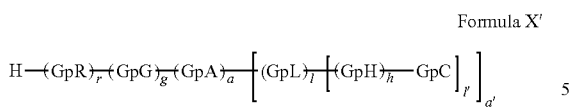

in which

GpR is chosen among the radicals according to formulas VII, VII' or VII":

Formula VII

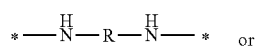 or

Formula VII'

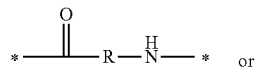 or

Formula VII"

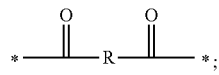;

Identical or different GpG and GpH are chosen among the radicals according to formulas XI or XI';

Formula XI

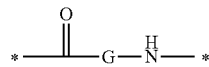

Formula XI'

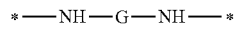

GpA is chosen among the radicals according to formulas VIII

Formula VIII

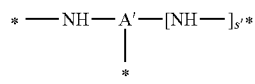

In which A' is chosen among the radicals according to formulas VIII', VIII" or VIII'"

Formula VIII'

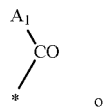 or

Formula VIII"

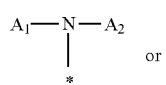 or

Formula VIII'"

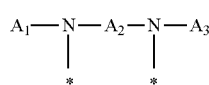

GpL is chosen among the radicals according to formulas XII

Formula XII

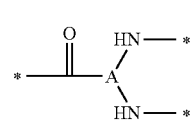

GpC is a radical according to formula IX:

Formula IX

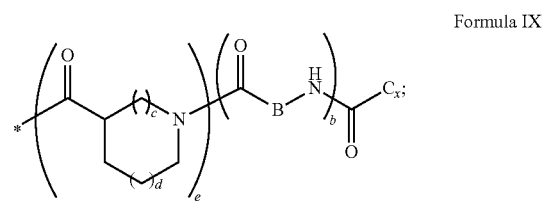

* indicate the attachment sites of the different groups linked by amide functions;

a is an integer equal to 0 or to 1 and a'=1 if a=0 and a'=1, 2 or 3 if a=1;

a' is an integer equal to 1, to 2 or to 3;

b is an integer equal to 0 or to 1;

c is an integer equal to 0 or to 1, and if c is equal to 0, then d is equal to 1 or to 2;

d is an integer equal to 0, to 1 or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6;

l is an integer equal to 0 or to 1 and l'=1 if l=0 and l'=2 if l=1;

r is an integer equal to 0, 1 or to 2;

s' is an integer equal to 0 or to 1;

And if e is different from 0, then at least one of g, h or l is different from 0;

And if a=0, then l=0;

A, $A_1$, $A_2$ and $A_3$ identical or different, are linear or branched alkyl radicals comprising from 1 to 8 carbon atoms and/or, substituted by a radical from a saturated, unsaturated or aromatic ring;

B is a radical ether or polyether, unsubstituted, comprising from 4 to 14 carbon atoms and from 1 to 5 oxygen atoms, or a linear or branched alkyl radical, and/or comprising an aromatic ring, comprising from 1 to 9 carbon atoms.;

$C_x$ is a linear or branched, monovalent alkyl radical and/or comprising a cyclic part, in which x indicates the number of carbon atoms, and:

When the hydrophobic radical -Hy bears 1 -GpC, then $9 \leq x \leq 25$,

When the hydrophobic radical -Hy bears 2 -GpC, then $9 \leq x \leq 15$,

When the hydrophobic radical -Hy bears 3 -GpC, then $7 \leq x \leq 13$,

When the hydrophobic radical -Hy bears 4 -GpC, then $7 \leq x \leq 11$,

When the hydrophobic radical -Hy bears at least 5 -GpC; $6 \leq x \leq 11$;

G is a branched alkyl radical of 1 to 8 carbon atoms, said alkyl radical bears one or more free carboxylic acid functions, R is a radical chosen from the group consisting of a divalent, linear or branched alkyl radical comprising from 1 to 12 carbon atoms, a divalent, linear or branched alkyl radical comprising 1 to 12 carbon atoms bearing one or more —$CONH_2$ functions or an unsubstituted ether or polyether radical comprising from 4 to 14 carbon atoms and from 1 to 5 oxygen atoms, the hydrophobic radical(s) -Hy according to formula X being bound- to the PLG:
  via a covalent bond between a carbonyl of hydrophobic radical -Hy and a nitrogen atom borne by the PLG, thus forming an amide function resulting from the reaction of an amine function borne by the PLG and an acid function borne by the precursor Hy' of the hydrophobic radical -Hy, and
  via a covalent bond between a nitrogen atom of the hydrophobic radical -Hy and a carbonyl borne by the PLG; thus forming an amide function resulting from the reaction of an amine function of the precursor -Hy' of the hydrophobic radical -Hy and an acid function borne by the PLG, The ratio M between the number of hydrophobic radicals and the number of glutamic or aspartic unites being comprised from 0<M≤0.5;

when several hydrophobic radicals are borne by a co-polyamino acid, then they are identical or different, The degree of polymerization DP in glutamic or aspartic units for the PLG chains is comprised from 5 to 250;

Free carboxylic acids being in the form of an alkaline cation salt chosen from the group consisting of $Na^+$ and $K^+$.

16. A method for improving the physical chemical stability of a composition according to claim 1 by adding ionic species chosen from the group of anions, cations and/or zwitterions.

17. The composition according to claim 2, wherein the co-polyamino acid bearing carboxylate charges and hydrophobic radicals is chosen among the co-polyamino acids according to formula XXX, in which in which R1=R'1 and R2=R'2, according to formula XXXa below:

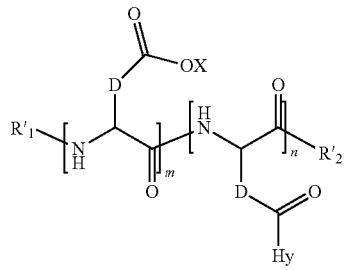

Formula XXXa in which, m, n, X, D and Hy as defined in claim 2, $R'_1$ is a radical chosen from the group consisting of a H, a linear acyl group in C2 to C10, a branched acyl group in C3 to C10, a benzyl, a terminal "amino acid" unit and a pyroglutamate, $R'_2$ is a hydrophobic radical chosen from the group consisting of H, the linear or branched or cyclic alkyls in C2 to C10, the benzyl and said R' and R" alkyls may form together one or more saturated, unsaturated and/or aromatic rings and/or may comprise heteroatoms, chosen from the group consisting of O, N and S.

* * * * *